US012115101B2

(12) United States Patent
Dabrowiak et al.

(10) Patent No.: US 12,115,101 B2
(45) Date of Patent: Oct. 15, 2024

(54) USER INTERFACE AND DATA MANAGEMENT FOR TEMPERATURE MANAGEMENT SYSTEM

(71) Applicant: Zoll Circulation, Inc., San Jose, CA (US)

(72) Inventors: Jeremy Thomas Dabrowiak, Santa Clara, CA (US); Sean W. Yip, San Jose, CA (US); George L. Walls, San Jose, CA (US); Neil Jacobson, Los Altos, CA (US); David M. Braunstein, Mountain View, CA (US)

(73) Assignee: Zoll Circulation, Inc., San Jose, CA (US)

( * ) Notice: Subject to any disclaimer, the term of this patent is extended or adjusted under 35 U.S.C. 154(b) by 0 days.

(21) Appl. No.: 17/561,487

(22) Filed: Dec. 23, 2021

(65) Prior Publication Data

US 2022/0313481 A1    Oct. 6, 2022

Related U.S. Application Data

(60) Provisional application No. 63/169,150, filed on Mar. 31, 2021.

(51) Int. Cl.
| | |
|---|---|
| *A61F 7/12* | (2006.01) |
| *A61F 7/08* | (2006.01) |
| *G06T 11/20* | (2006.01) |
| *A61F 7/00* | (2006.01) |

(52) U.S. Cl.
CPC .............. *A61F 7/12* (2013.01); *A61F 7/08* (2013.01); *G06T 11/203* (2013.01); *A61F 2007/0056* (2013.01); *A61F 2007/126* (2013.01); *G06T 2200/24* (2013.01); *G06T 2210/41* (2013.01)

(58) Field of Classification Search
CPC ...... A61F 7/12; A61F 7/08; A61F 2007/0056; A61F 2007/126; A61F 7/00; A61F 2007/0093; G06T 11/203; G06T 2200/24; G06T 2210/41
See application file for complete search history.

(56) References Cited

U.S. PATENT DOCUMENTS

| | | |
|---|---|---|
| 9,241,827 B2 | 1/2016 | Lim et al. |
| 9,314,370 B2 | 4/2016 | Dabrowiak et al. |
| 9,433,526 B2 | 9/2016 | Protasiewicz et al. |
| 9,492,633 B2 | 11/2016 | Dabrowiak et al. |
| 9,662,243 B2 | 5/2017 | Dabrowiak |
| 9,717,625 B2 | 8/2017 | Lim et al. |
| 10,045,881 B2 | 8/2018 | Helkowski et al. |

(Continued)

OTHER PUBLICATIONS

PCT International Search Report and Written Opinion in International Appln. No. PCT/US2021/065153, dated Mar. 17, 2022, 21 pages.

*Primary Examiner* — Adam Z Minchella
(74) *Attorney, Agent, or Firm* — Fish & Richardson P.C.

(57) ABSTRACT

A temperature management system is configured to control a temperature of a patient's body using a heat exchange device. The temperature management system is configured to deliver temperature management treatment or therapy to a patient. A user interface of the system is configured to display operational data and patient data on the user interface in a configuration that allows a user to determine or review one or more periods of the performed temperature management treatment.

21 Claims, 21 Drawing Sheets

(56) References Cited

U.S. PATENT DOCUMENTS

| | | | |
|---|---|---|---|
| 2004/0267340 A1* | 12/2004 | Cioanta | A61F 7/123 607/113 |
| 2009/0099629 A1* | 4/2009 | Carson | A61F 7/0085 607/96 |
| 2013/0090708 A1 | 4/2013 | Dabrowiak et al. | |
| 2018/0018519 A1 | 1/2018 | O'Brien et al. | |
| 2018/0185193 A1 | 7/2018 | Mazzone et al. | |
| 2018/0207024 A1 | 7/2018 | Dabrowiak et al. | |
| 2018/0325725 A1* | 11/2018 | Dabrowiak | A61F 7/12 |
| 2019/0201236 A1 | 7/2019 | Scott et al. | |
| 2020/0405529 A1 | 12/2020 | Taylor et al. | |

* cited by examiner

USER INTERFACE AND DATA MANAGEMENT FOR TEMPERATURE MANAGEMENT SYSTEM

CLAIM OF PRIORITY

This application claims priority under 35 U.S.C. § 119(e) to U.S. Patent Application Ser. No. 63/169,150, filed on Mar. 31, 2021, the entire contents of which are hereby incorporated by reference.

TECHNICAL FIELD

The present disclosure relates generally to the fields of medicine and engineering and more particularly to improved devices, systems and methods for controlling a patient's body temperature.

BACKGROUND

In various clinical situations, it is desirable to warm, cool or otherwise control the body temperature of a subject. For example, hypothermia can be induced in humans and some animals for the purpose of protecting various organs and tissues (e.g., heart, brain, kidneys) against the effects of ischemic, anoxic or toxic insult. For example, animal studies and/or clinical trials suggest that mild hypothermia can have neuroprotective and/or cardioprotective effects in animals or humans who suffer from ischemic cardiac events (e.g., myocardial infarction, acute coronary syndromes, etc.), postanoxic coma after cardiopulmonary resuscitation, traumatic brain injury, stroke, subarachnoid hemorrhage, fever and neurological injury.

One method for inducing hypothermia is by intravascular or endovascular temperature management wherein a heat exchange catheter is inserted into a blood vessel and a thermal exchange fluid is circulated through a heat exchanger positioned on the portion of the catheter that is inserted in the blood vessel. As the thermal exchange fluid circulates through the catheter's heat exchanger, it exchanges heat with blood flowing past the heat exchanger in the blood vessel. Such technique can be used to cool the subject's flowing blood thereby resulting in a lowering of the subject's core body temperature to some desired target temperature. Endovascular temperature management is also capable of warming the body and/or of controlling body temperature to maintain a monitored body temperature at some selected temperature. If a controlled rate of re-warming or re-cooling from the selected target temperature is desired, that too can be accomplished by carefully controlling the amount of heat added or removed from the body and thereby controlling the temperature change of the patient.

SUMMARY

This document describes a temperature management system configured to control a temperature of a patient's body using a heat exchange device. The temperature management system is configured to deliver temperature management treatment or therapy to a patient. The temperature management system is configured to monitor how a heat exchange device (such as a catheter, pad, etc.) is operating to control the temperature of the patient's body (also called treatment or heat exchange treatment). The temperature management system is configured to measure operational data representing operation of one or more hardware aspects of the temperature management system. The temperature management system is configured to measure patient data representing one or more physiological aspects of the patient during treatment of the patient e.g., patient temperature. The operational data and the patient data that are measured during treatment of the patient may be referred to as treatment data and the temperature management system is configured to control the temperature of the patient's body based on the operational and/or patient data. The temperature management system is configured to display, by a user interface, operational data of the temperature management system and patient data during treatment.

The user interface is configured to display operational data and patient data on the user interface in a configuration that allows a user to determine a stage or period of a temperature management treatment (e.g., a treatment cycle) being performed for the temperature management treatment of a patient. The user interface may show a present treatment period as well as one or more past treatment periods. Each stage or treatment period of the temperature management treatment may be associated with a target patient temperature and/or a rate of cooling or heating the patient to control the patient temperature to the target temperature.

A cooling or heating power exerted or delivered by the temperature management system to cool or warm the patient may be displayed on the user interface. The cooling or warming power (also called "effort" or simply "power" or "power value") represents how hard the temperature management system is working to heat or cool the patient. The power value referred to herein may also be considered to be a warming or cooling potential value. In certain implementations, the actual value of the power may be a fraction or percentage of a maximum possible cooling or heating rate or capacity or cooling or warming power capability of the of the temperature management system to cool or warm the patient based on a difference between a bath temperature of the temperature management system and the patient's current temperature. The temperature may be measured in any convenient units, such as Kelvin, Centigrade/Celsius or Fahrenheit.

The temperature management system is configured to generate log entries for the operational data and/or the patient data (e.g., treatment data). In some implementations, a data message (also called a log message) represents an instant snapshot of the operational data and the patient data. For example, a data message can include a current patient temperature and a current power or heat exchange effort value at a given time (e.g., associated with a time stamp). In some implementations, a data message can include data representing a stage or treatment period or a system mode during a treatment period of the heat exchange treatment for the patient in a log entry. The data messages are stored in a digital format that enables streaming of the data messages to a remote system. The remote system is configured to quickly extract the values representing the patient data and the operational data of the temperature management system and display a representation of these data on a remote user interface. For example, data messages can be formatted for streaming to a nurse station from a hospital room. In some implementations, data messages can include warnings or alerts that prompt intervention from a user of the remote system. In some implementations, the data messages can be stored in a structured format that facilitates searching and retrieving of treatment data for the patient for one or more instances of treatment by the temperature management system.

The implementations described herein can provide one or more advantages. The temperature management system can send treatment data to a remote device or system as a data stream with minimal data overhead. The data stream has a relatively low bandwidth as the data of the data stream are configured for a minimal data footprint. The treatment data can be quickly ingested by the remote device and displayed to users of the remote device, such as in combination from other instances of the temperature management system.

The temperature management system may determine a power value representing cooling or warming power delivered to the patient during a given stage of a heat exchange treatment. The representation of power simultaneously with the current stage of the heat exchange treatment can inform a user whether the treatment is proceeding as expected. For example, if the temperature management system is delivering a relatively high percentage of the maximum cooling power capability of the system e.g., at a current or measured patient temperature, to maintain the temperature of the patient at a target temperature, it can be determined that a thermoregulatory response of the patient is strong, and that the patient may be in a febrile state.

The temperature management system can display past and current stages or treatment periods of temperature management treatment. A user can determine exactly how treatment is currently proceeding (and has proceeded) by observing the values (e.g., time periods, patient temperatures, etc.) associated with each executed stage treatment period of the treatment. Each of the treatment periods can be associated with a log entry of a treatment log detailing the treatment for the patient, which can include a summary of treatment that occurs for a particular treatment period. The log entries can be stored in a database in a structured format that relates the messages for a particular treatment of a particular patient together in the database. For example, by searching a key value representing a patient identifier or a treatment instance, the treatment data for each stage or treatment period of the treatment can be returned to the user. The treatment periods may be visualized or displayed in the form of a treatment log or sequence of treatment periods showing one or more of the most recent past treatment periods and the current treatment period.

The temperature management system may generate an alert that informs a health care provider locally or in a remote location of a transition from a first treatment period to a second treatment period, a patient's temperature, a fraction or percentage of the maximum cooling or warming power capability of the temperature management system being delivered to the patient, a cooling or warming power exerted by the temperature management system or a value indicative of a patient's thermoregulatory activity and/or send the alert to another device to quickly induce a response by the health care provider. For example, the alert can be streamed to a remote device for presentation along with the treatment data of the patient. A user (e.g., a medical service provider) can quickly review the treatment data and the alert to determine whether intervention is required.

The implementations described herein can include one or more of the following embodiments.

In a first aspect, a temperature management system for controlling a temperature of a body of a patient, the system comprising: a heat exchange device configured to deliver a temperature management treatment to the patient, the temperature management treatment based on circulation of a coolant; an extracorporeal control console coupled to the heat exchange device and configured to circulate coolant and generate coolant temperature data representing a temperature of the coolant during the temperature management treatment; optionally at least one sensor coupled to the extracorporeal control console and configured to generate a patient temperature data indicative of a temperature of the body of the patient; a processor, a memory storing instructions, and associated circuitry communicatively coupled to the sensor, wherein the processor is configured to: receive the patient temperature data from the sensor; receive the coolant temperature data from the extracorporeal control console; determine a power value representing cooling or warming power delivered to the patient based on a relationship between the patient temperature data and the coolant temperature data, wherein the relationship comprises a ratio representing a fraction of the maximum cooling or warming power capability of the temperature management system to cool or warm the patient; and generate and display the power value as a percentage of the maximum cooling or warming power capability of the temperature management system to cool or warm the patient.

A temperature management system such as that of the first aspect may be configured to perform a method comprising: receiving patient temperature data; receiving coolant temperature data; determining a value representing cooling or warming delivered to the patient based on a relationship between the patient temperature data and the coolant temperature data, and displaying the value. The relationship may comprise a ratio representing a fraction of the maximum cooling or warming capability of the temperature management system to cool or warm the patient.

In some implementations, the ratio is defined as:

$$\text{Power value} = \left| \frac{T_{patient} - T_{bath}}{T_{patient} - T_{bath\_max}} \right|$$

where Power value is the power value as a percentage, $T_{patient}$ is the patient's current temperature, $T_{bath}$ is the current bath temperature, and $T_{bath}$ max is the maximum bath temperature representing a highest bath temperature possible when raising the patient's temperature or heating the patient or a lowest bath temperature possible when lowering the patient's temperature or cooling the patient.

In some implementations, determining the ratio representing a fraction of the maximum cooling or warming power capability of the temperature management system to cool or warm the patient comprises: determining, from the coolant temperature, a bath temperature of a cooling or warming bath of the heat exchange device; determining a first value representing a difference between the bath temperature and the patient temperature; and determining a second value representing a difference between a maximum bath temperature and the patient temperature; and taking the ratio of the first value and the second value.

In some implementations, determining the power value based on a relationship that includes patient temperature allows the processor to dynamically adjust the power value in relation to the maximum cooling or warming power that the system can deliver to the patient at the measured patient temperature.

In some implementations, a value of the ratio is zero if a working fluid pump of the extracorporeal control console is off.

In some implementations, when a working fluid pump of the extracorporeal control console is on, a value of the ratio is based solely on the coolant temperature and the patient temperature.

In some implementations, the ratio is further based on a speed of a working fluid pump of the extracorporeal control console.

In some implementations, the ratio is not based on a speed of a working fluid pump of the extracorporeal control console.

In some implementations, the ratio is further based on a power consumption of the extracorporeal control console.

In some implementations, the system further comprising a user interface configured to display a visual representation of the data representing the percentage of the maximum cooling or warming power capability of the temperature management system to cool or warm the patient. In some implementations, visual representation comprises an arcuate meter.

In some implementations, the visual representation comprises a linear meter.

In some implementations, the user interface is further configured to display a representation of operational data for one or more periods of the temperature management treatment of the patient, the operational data representing operation of at least a portion of the heat exchange device or the extracorporeal control console.

In some implementations, the representation of operational data for one or more periods of the temperature management treatment of the patient comprises a treatment log representing operational data for multiple periods of the temperature management treatment of the patient.

In some implementations, the representation of operational data for one or more periods of the temperature management treatment of the patient comprises a list of log entries.

In some implementations, the representation of operational data for one or more periods of the temperature management treatment of the patient comprises a sequence of symbols, each representing a log entry.

In some implementations, the representation of operational data for one or more periods of the temperature management treatment of the patient comprises a sequence of symbols, each symbol of the sequence representing a log entry.

In some implementations, the symbol is a mark, character, line, letter, graphical symbol, icon, or picture.

In some implementations, a log entry of the one or more log entries includes data representing one or more of a cooling or warming rate applied during a treatment period, a target patient temperature value, a patient temperature value, a system mode during a treatment period, a time period associated with a treatment period, whether the system is operating to lower, raise or maintain the patient's temperature during a treatment period, and a position of a treatment period relative to one or more other treatment periods for the temperature management treatment of the patient.

In some implementations, the heat exchange device is a catheter or surface pad. In some implementations, the patient temperature data is the patient's measured or current temperature, and the power value is the percentage of the maximum cooling or warming power capability of the temperature management system at the measured or current temperature.

In some implementations, the temperature management system is further configured to determine whether the system changes to a new system state from a current system state before updating the visual representation of the treatment log to display additional operational data. In some implementations, the temperature management system is further configured to execute a sampling algorithm over a fixed period of time (e.g., a debounce time) or grace period to determine whether the system changes to a new system state from a current system state before updating the visual representation of the treatment log to display additional operational data.

In some implementations, the temperature management system is further configured to update the visual representation of the treatment log. A furthest left section of the sequence of sections of the visual representation of the treatment log that is not already populated may be configured to populate with at least the operational data for the current treatment period. When the visual representation of the treatment log is fully populated and additional operational data is being added, contents of each section may shift one section left to empty a right most section for display of the additional operational data.

In some implementations, the temperature management system is further configured to display a symbol representing operation of the temperature management system to maintain the temperature of the body of the patient in the form of horizontal line segment. The temperature management system may display a symbol representing operation of the temperature management system to lower the temperature of the body of the patient by using a downward sloping line segment. The temperature management system may display a symbol representing operation of the temperature management system to raise the temperature of the body of the patient by using an upward sloping line segment.

In some implementations, a vertical position of the horizontal line segment, the downward sloping line segment, or the upward sloping line segment is based on a target temperature value for the respective treatment period.

In some implementations, the vertical position is a high position when the target temperature is above a first threshold value, a low position when the target temperature is below a second threshold value, or a middle position when the target temperature is between the first threshold value and the second threshold value.

In a second aspect, a temperature management system for controlling a temperature of a body of a patient comprises a heat exchange device configured to deliver a temperature management treatment to the patient, the temperature management treatment based on circulation of a coolant; an extracorporeal control console coupled to the heat exchange device and configured to generate operational data, the operational data comprising coolant temperature data representing a coolant temperature of the coolant during the temperature management treatment; optionally one or more sensors coupled to the extracorporeal control console and configured to generate patient temperature data indicative of a temperature of the body of the patient; a user interface that is coupled to the extracorporeal control console; and a processor, a memory storing instructions, and associated circuitry communicatively coupled to the user interface and the one or more sensors, wherein the processor is configured to: receive the patient temperature data from the one or more sensors; receive coolant temperature data representing a coolant temperature; determine a power value representing cooling or warming power delivered to the patient based on a relationship between the patient temperature data and the coolant temperature data, wherein the relationship comprises a ratio representing a fraction of the maximum cooling or warming power capability of the temperature management system to cool or warm the patient; generate at least one treatment log based on the operational data and the patient temperature data; wherein the treatment log includes multiple log entries associated with respective periods of the temperature management treatment; and cause the user interface to simultaneously present the power value and the treatment log.

A temperature management system such as that of the second aspect may be configured to perform a method comprising: receiving patient temperature data; receiving coolant temperature data representing a coolant temperature; determining a value representing cooling or warming delivered to the patient based on a relationship between the patient temperature data and the coolant temperature data; generating at least one treatment log based on operational data and the patient temperature data; and causing the user interface to simultaneously present the value and the treatment log. The relationship may comprise a ratio representing a fraction of the maximum cooling or warming capability of the temperature management system to cool or warm the patient. The treatment log may include multiple log entries associated with respective periods of the temperature management treatment.

In some implementations, the power value is displayed as a percentage of the maximum cooling or warming power capability of the temperature management system to cool or warm the patient.

In some implementations, the operational data comprises one or more of a target patient temperature, a system mode, a pump speed, and a cooling or warming rate.

In some implementations, the user interface is configured to display a visual representation of the power value.

In some implementations, the visual representation comprises an arcuate meter.

In some implementations, the log entries comprise a sequence of symbols each representing a cooling or warming period of a temperature management cycle of the temperature management treatment.

In some implementations, the symbol is a mark, character, line, letter, graphical symbol, icon, or picture.

In some implementations, each log entry corresponds to a period where the system is operating to lower the patient temperature, cooling period, a maintenance period, a period where the system is operating to raise the patient temperature, or a warming period of a temperature management treatment.

In some implementations, a log entry includes one or more of a temperature raising status, a warming status, a maintenance status, a temperature lowering status, a cooling status, a target temperature, and a time period associated with the warming or cooling period.

In some implementations, the log entries or treatment periods of the treatment log are ranked in order of occurrence.

In some implementations, the processor is further configured to generate digital output data including a predefined format that enables the digital output data to be streamed to a remote device.

In some implementations, the system further comprises a transmitter configured to transmit the digital output data to the remote device.

In some implementations, the processor is configured to cause the digital output data to be streamed to the remote device in real time or in near real time during the temperature management treatment.

In some implementations, the predefined format is configured to enable the remote device to parse the digital output data for displaying the patient data and/or the operational data upon receiving the digital output data.

In some implementations, the processor is configured to stream the digital output data over a Wi-Fi communications link.

In some implementations, the heat exchange device is a catheter or surface pad. In some implementations, the patient temperature data is the patient's measured or current temperature, and the power value is the fraction of the maximum cooling or warming power capability of the temperature management system at the measured or current temperature.

In a third aspect, a temperature management system for controlling a temperature of a body of a patient, the system comprising: a heat exchange device configured to deliver a temperature management treatment to the patient, the temperature management treatment based on circulation of a coolant; an extracorporeal control console coupled to the heat exchange device and configured to generate operational data, the operational data comprising coolant temperature data representing a coolant temperature of the coolant during the temperature management treatment; optionally one or more sensors coupled to the extracorporeal control console and configured to generate patient temperature data indicative of a temperature of the body of the patient; a user interface that is coupled to the extracorporeal control console; and a processor, a memory storing instructions, and associated circuitry communicatively coupled to the user interface and the one or more sensors, wherein the processor is configured to: receive the coolant temperature data and the patient temperature data from the temperature management system; determine a power value representing cooling or warming power delivered to the patient based on a relationship between the patient temperature data and the coolant temperature data, wherein the relationship comprises a ratio representing a fraction of the maximum cooling or warming power capability of the temperature management system to cool or warm the patient; generate and display the power value as a percentage of the maximum cooling or warming power capability of the temperature management system to cool or warm the patient; and cause the user interface to simultaneously present the power value and the coolant temperature for the coolant during the temperature management treatment.

A temperature management system such as that of the third aspect may be configured to perform a method comprising: receiving the coolant temperature data and the patient temperature data; determining a value representing cooling or warming delivered to the patient based on a relationship between the patient temperature data and the coolant temperature data; displaying the power value; and simultaneously displaying the value and the coolant temperature for the coolant during the temperature management treatment. The relationship may comprise a ratio representing a fraction of the maximum cooling or warming power capability of the temperature management system to cool or warm the patient. The value may be displayed as a percentage.

In some implementations, the coolant temperature is a heat exchange bath temperature.

In some implementations, the heat exchange device is a catheter or surface pad.

The first to third aspects relate in a general sense to a temperature management system for controlling a temperature of a body of a patient in which the system is configured to determine a value representing a cooling or warming delivered to the patient based on a relationship between the patient temperature data and the coolant temperature data, wherein the relationship comprises a ratio representing a fraction of a maximum cooling or warming capability of the temperature management system to cool or warm the patient. The determined value relates to an internal state prevailing in the system and may assist the user to properly operate the system as described in detail below with relation to the specific description. The apparatus of the temperature management system may include a heat exchange device. The heat exchange device may be configured to deliver a temperature management treatment to the patient. The temperature management treatment may be based on circulation of a coolant. The apparatus of the temperature management system may include an extracorporeal control console coupled to the heat exchange device. The extracorporeal control console may be configured to circulate coolant and generate coolant temperature data representing a temperature of the coolant during the temperature management treatment. The extracorporeal control console may be configured to generate operational data. The operational data may comprise coolant temperature data representing a coolant temperature of the coolant during the temperature management treatment. The apparatus of the temperature management system may include at least one sensor. The at least one sensor may be coupled to the extracorporeal control console. The at least one sensor may be configured to generate patient temperature data indicative of a temperature of the body of the patient. The apparatus of the temperature management system may include a processor, a memory storing instructions, and associated circuitry communicatively coupled to the sensor.

In a fourth aspect, a temperature management system for controlling a temperature of a body of a patient, comprises a heat exchange device configured to deliver a temperature management treatment to the patient; an extracorporeal control console coupled to the heat exchange device and configured to generate operational data representing operation of the temperature management system during the temperature management treatment; at least one sensor coupled to the extracorporeal control console and configured to generate a patient temperature data indicative of a temperature of the body of the patient; a processor, a memory storing instructions, and associated circuitry communicatively coupled to the sensor, wherein the processor is configured to: receive the patient temperature data from the sensor and the operational data from the extracorporeal control console; control, based on the patient temperature, the temperature management system to cool or warm the body of the patient; generate log entries for one or more treatment periods, a log entry for a treatment period indicating at least the operational data associated with that treatment period; generate a treatment log that specifies multiple treatment periods of the temperature management treatment of the patient; and generate a visual representation of the treatment log, the visual representation comprising a sequence of sections, each section corresponding to a treatment period of the temperature management treatment of the patient, each section comprising: a symbol representing operation of the temperature management system to lower, raise or maintain the temperature of a body of a patient, wherein each symbol is distinguished from each other symbol in the sequence of sections.

A temperature management system such as that of the fourth aspect may be configured to perform a method comprising: receiving patient temperature data and operational data; controlling, based on the patient temperature, the temperature management system to cool or warm the body of the patient; generating log entries for one or more treatment periods, a log entry for a treatment period indicating at least the operational data associated with that treatment period; generating a treatment log that specifies multiple treatment periods of the temperature management treatment of the patient; and generating a visual representation of the treatment log, the visual representation comprising a sequence of sections, each section corresponding to a treatment period of the temperature management treatment of the patient, each section comprising: a symbol representing operation of the temperature management system to lower, raise or maintain the temperature of a body of a patient, wherein each symbol is distinguished from each other symbol in the sequence of sections.

In some implementations, a log entry includes operational data representing one or more of a cooling or warming rate applied during the treatment period, a target patient temperature value, a name of the treatment period, a time period associated with the treatment period, and a position of the treatment period relative to one or more other treatment periods for the temperature management treatment of the patient.

In some implementations, the user interface is further configured to display a representation of the log entries including the operational data and the temperature data associated with that treatment period.

In some implementations, the representation of the log entries includes a list of the log entries.

In some implementations, the representation of the log entries includes a sequence of symbols, each symbol of the sequence representing a log entry.

In some implementations, each symbol of the sequence includes a line segment that is separated from other symbols of the sequence.

In some implementations, the positioning of a line segment may be determined by one or more of the following rules: if the system is operating to raise a patient's temperature, a sloped line segment starts in the bottom left corner a section; if the system is operating to lower a patient's temperature, a sloped line segment starts in the upper left corner of a section; if the system is operating to maintain a patient's temperature, the horizontal line segment starts in a middle left portion of a section.

In some implementations, four consecutive line segments appearing in adjacent sections, each subsequent line segment starts where the previous line ended in a Y axis or vertical direction in the section.

In some implementations, each symbol represents the system operating in a manner to raise, lower or maintain the temperature of a body of a patient temperature.

In some implementations, an alert associated with a log entry is generated, the alert indicating that a first treatment period has ended and a second treatment period has commenced.

In some implementations, the log entry for a treatment period indicates the operational data and the patient temperature data associated with that treatment period.

In some implementations, the one or more sections do not comprise a graph.

In some implementations, the heat exchange device is a catheter or surface pad. In some implementations, the patient temperature data is the patient's measured or current temperature, and the power value is the percentage of the maximum cooling or warming power capability of the temperature management system at the measured or current temperature.

In a fifth aspect, a temperature management system for controlling a temperature of a body of a patient, comprises a heat exchange device configured to deliver a temperature management treatment to the patient; an extracorporeal control console coupled to the heat exchange device and configured to generate operational data representing operation of the temperature management system during the temperature management treatment; at least one sensor coupled to the extracorporeal control console and configured to generate a patient temperature data indicative of a temperature of the body of the patient; a processor, a memory storing instructions, and associated circuitry communicatively coupled to the sensor, wherein the processor is configured to: receive the patient temperature data and the operational data; generate at least one treatment log based on the operational data and the patient temperature data; generate a visual representation of the treatment log, the visual representation comprising: a sequence of sections, each section corresponding to a treatment period of the temperature management treatment of the patient, each section comprising: a symbol representing operation of the temperature management system to lower, raise or maintain the temperature of a body of a patient; and a representation of a duration for the treatment period; wherein each symbol is distinguished from each other symbol in the sequence of sections.

A temperature management system such as that of the fifth aspect may be configured to perform a method comprising: receiving the patient temperature data and the operational data; generating at least one treatment log based on the operational data and the patient temperature data; generating a visual representation of the treatment log. The visual representation may comprise: a sequence of sections, each section corresponding to a treatment period of the temperature management treatment of the patient, each section comprising: a symbol representing operation of the temperature management system to lower, raise or maintain the temperature of a body of a patient; and a representation of a duration for the treatment period; wherein each symbol is distinguished from each other symbol in the sequence of sections.

In some implementations, at least one symbol is a different color than one or more other symbols of a sequence of symbols.

In some implementations, at least one symbol is separated from at least one other symbol by one of a gap or symbol.

In some implementations, each symbol appears discontinuous from each other symbol.

In some implementations, each symbol appears continuous with each other symbol, and wherein each symbol is distinguished using a color, pattern, or fill.

In some implementations, each symbol appears at a relative height within a corresponding section of the sequence to the other symbols, wherein a relative height of a given symbol corresponds to a patient temperature or target temperature for the treatment period represented by that section.

In some implementations, a section representing an ongoing treatment period of the temperature management treatment includes a highlighted symbol.

In some implementations, a section includes a text identifier indicating the system mode corresponding to the treatment period of that section.

In some implementations, one or more of the sections include a numerical representation of a target patient temperature, an initial patient temperature, an ending patient temperature or any combination thereof for the treatment period of a section.

In some implementations, the sequence of one or more sections includes at least four sections, and wherein each section is populated with a symbol once a corresponding treatment period is performed by the extracorporeal control console and heat exchange device.

In some implementations, the symbol comprises a line segment.

In some implementations, the symbol is an upward sloping line segment from left to right in a section to represent the system is warming the patient temperature or operating in a manner to raise the patient's temperature over that treatment period.

In some implementations, the symbol is a downward sloping line segment from left to right in a section to represent the system is cooling the patient temperature or operating in a manner to lower the patient's temperature over that treatment period.

In some implementations, the symbol is a horizontal line segment in a section to represent the system is maintaining the patient temperature or operating in a manner to maintain the patient's temperature over that treatment period.

In some implementations, at least one line segment is a different color than one or more other line segments of a sequence of line segments.

In some implementations, at least one line segment is separated from at least one other line segment by one of a gap or a symbol.

In some implementations, each line segment appears discontinuous from each other line segment.

In some implementations, a line segment representing a currently performed treatment period of the temperature management treatment includes an arrowhead.

In some implementations, each line segment appears continuous with each other line segment, and wherein each line segment is distinguished using a color, pattern, or fill.

In some implementations, each line segment appears at a relative height within a corresponding section of a sequence to the other line segments, wherein a relative height of a given line segment corresponds to a patient temperature or target temperature for the treatment period represented by that section.

In some implementations, a sloping line segment is positioned in a given section at one of two possible relative heights, and wherein a horizontal line segment is positioned in the given section at one of three relative heights.

In some implementations, the positioning of a line segment may be determined by one or more of the following rules: if the system is operating to raise a patient's temperature, a sloped line segment starts in the bottom left corner a section; if the system is operating to lower a patient's temperature, a sloped line segment starts in the upper left corner of a section; if the system is operating to maintain a patient's temperature, the horizontal line segment starts in a middle left portion of a section.

In some implementations, four consecutive line segments appearing in adjacent sections, each subsequent line segment starts where the previous line ended in a Y axis or vertical direction in the section.

In some implementations, the heat exchange device is a catheter or surface pad.

In some implementations, the one or more sections do not comprise a graph.

In a sixth aspect, a temperature management system for controlling a temperature of a body of a patient comprises a heat exchange device configured to deliver a temperature management treatment to the patient; an extracorporeal control console coupled to the heat exchange device and configured to generate operational data representing operation of the temperature management system during the temperature management treatment; optionally one or more sensors coupled to the extracorporeal control console and configured to generate patient data representing a status of the patient; a user interface that is coupled to the extracorporeal control console, the user interface being configured to display a plurality of regions, the plurality of regions comprising: a first window configured to display a current patient temperature based on data received from the one or more sensors; a second window configured to display a power meter representing a cooling or warming power value as a percentage of the maximum cooling or warming power capability of the temperature management system to cool or warm the patient; a third window configured to display a treatment log comprising a plurality of entries, each entry corresponding to a treatment period of the temperature management treatment, each entry including a representation of at least a portion of the operational data for the respective treatment period; and a fourth window configured to display the operational data comprising at least a coolant temperature of coolant circulated by the extracorporeal control console.

A temperature management system such as that of the sixth aspect may be configured to perform a method comprising displaying a plurality of regions. The plurality of regions comprising: a first window configured to display a current patient temperature based on data received from the one or more sensors; a second window configured to display a power meter representing a cooling or warming power value as a percentage of the maximum cooling or warming power capability of the temperature management system to cool or warm the patient; a third window configured to display a treatment log comprising a plurality of entries, each entry corresponding to a treatment period of the temperature management treatment, each entry including a representation of at least a portion of the operational data for the respective treatment period; and a fourth window configured to display the operational data comprising at least a coolant temperature of coolant circulated by the extracorporeal control console.

A temperature management system such as that of the sixth aspect may be configured to determine whether the system changes to a new system state from a current system state before updating the visual representation of the treatment log to display additional operational data. In some implementations, the temperature management system is configured to update the visual representation of the treatment log, wherein a furthest left section of the sequence of sections of the visual representation of the treatment log that is not already populated is configured to populate with at least the operational data for the current treatment period, wherein, when the visual representation of the treatment log is fully populated and additional operational data is being added, contents of each section shift one section left to empty a right most section for display of the additional operational data.

In some implementations, the temperature management of the sixth aspect is further configured to display a symbol representing operation of the temperature management system to maintain the temperature of the body of the patient in the form of horizontal line segment; display a symbol representing operation of the temperature management system to lower the temperature of the body of the patient by using a downward sloping line segment; and display a symbol representing operation of the temperature management system to raise the temperature of the body of the patient by using an upward sloping line segment.

In some implementations, a vertical position of the horizontal line segment, the downward sloping line segment, or the upward sloping line segment is based on a target temperature value for the respective treatment period.

In some implementations, the vertical position is a high position when the target temperature is above a first threshold value, a low position when the target temperature is below a second threshold value, or a middle position when the target temperature is between the first threshold value and the second threshold value.

In some implementations, generating the visual representation of the treatment log comprises: receiving input data indicating either a change to a target temperature or a new target temperature; and in response to receiving the input, generating a section of the visual representation of the treatment log.

In some implementations, generating the visual representation of the treatment log comprises: determining that the temperature of the body of the patient is within a threshold distance of a target patient temperature; and in response determining that the temperature of the body of the patient is within a threshold distance of a target patient temperature, generating a section of the visual representation of the treatment log which displays a symbol that represents operation of the temperature management system to maintain the temperature of the body of the patient.

In some implementations, none of the sections of the visual representation of the treatment log comprise a graph.

In a seventh aspect, a temperature management system for controlling a temperature of a body of a patient comprises a heat exchange catheter configured to deliver a temperature management treatment to the patient; an extracorporeal control console coupled to the heat exchange catheter and configured to generate operational data representing operation of the temperature management system during the temperature management treatment; optionally at least one sensor coupled to the extracorporeal control console and configured to generate a patient temperature data indicative of a temperature of the body of the patient; a processor, a memory storing instructions, and associated circuitry communicatively coupled to the sensor, wherein the processor is configured to: receive the patient temperature data from the sensor; control, based on the patient temperature data, the temperature management system to maintain the temperature of the body of the patient within a target temperature range; generate digital output data comprising treatment logs comprised of the patient temperature data and the operational data; store the digital output data; detect that a trigger condition of the temperature management treatment is satisfied, wherein the trigger condition is completion of all or a portion of the temperature management treatment; and in response to detecting the trigger condition is satisfied, transmit the digital output data to a remote device in real time or in near real time during or after the temperature management treatment of the patient.

A temperature management system such as that of the seventh aspect may be configured to perform a method comprising receiving patient temperature data; controlling, based on the patient temperature data, the temperature management system to maintain the temperature of the body of the patient within a target temperature range; generating digital output data comprising treatment logs comprised of the patient temperature data and the operational data; storing the digital output data; detecting that a trigger condition of the temperature management treatment is satisfied, wherein the trigger condition is completion of all or a portion of the temperature management treatment; and in response to detecting the trigger condition is satisfied, transmitting the digital output data to a remote device in real time or in near real time during or after the temperature management treatment of the patient.

In some implementations, the trigger condition is the completion of a treatment period.

In some implementations, the trigger condition is a powering off of the temperature management system.

In some implementations, the digital output data includes a predefined format that enables the digital output data to be streamed to a remote device.

In some implementations, the system comprises a transmitter configured to transmit the digital output data to the remote device.

In some implementations, the predefined format is configured to enable the remote device to parse the digital output data for displaying the temperature data and/or the operational data upon receiving the digital output data.

In some implementations, the processor is configured to stream the digital output data over a Wi-Fi communications link.

In some implementations, the operational data comprises one or more of a target patient temperature, a coolant temperature, a system mode, a pump speed, a cooling or warming rate, and % cooling or warming power.

In some implementations, the digital output data associates the operational data and/or the temperature data with one or more of a timestamp, an event type, an event code, an alarm limit, or a calibration coefficient.

In some implementations, the digital output data comprises a structured treatment log including one or more log entries.

In some implementations, a log entry of the one or more log entries includes data representing one or more of a cooling or warming rate applied during a treatment period, a target patient temperature value, a patient temperature value, a system mode during a treatment period, a time period associated with a treatment period, whether the system is operating to lower, raise or maintain the patient's temperature during a treatment period, and a position of a treatment period relative to one or more other treatment periods for the temperature management treatment of the patient.

In some implementations, the processor is configured to stream the digital output data to a remote server.

In some implementations, the processor is configured to stream the digital output data to an EMR data hub or hospital hub.

In some implementations, the power value is an indicator regarding the underlying condition of a patient.

In some implementations, processor is configured to provide an alert or prompt in response to the system exceeding a power value threshold.

Computer program code may be provided to implement any of the aspects. For example, there may be provided a non-transitory computer readable medium comprising computer program code that is configured to cause at least one processor to perform any of the method steps described with respect to the different aspects. It will be appreciated that an implementation described with respect to one aspect may be combined with a different aspect. In general it will be appreciated that the at least one sensor may be provided separately from a system of an aspect and the system may instead be configured to receive data from the sensor. This is particularly applicable in the case that the at least one sensor is a consumable item that may be provided separately to the remainder of the system.

The details of one or more embodiments are set forth in the accompanying drawings and the description below. Other features and advantages will be apparent from the description and drawings, and from the claims.

DETAILED DESCRIPTION

Figure 1:
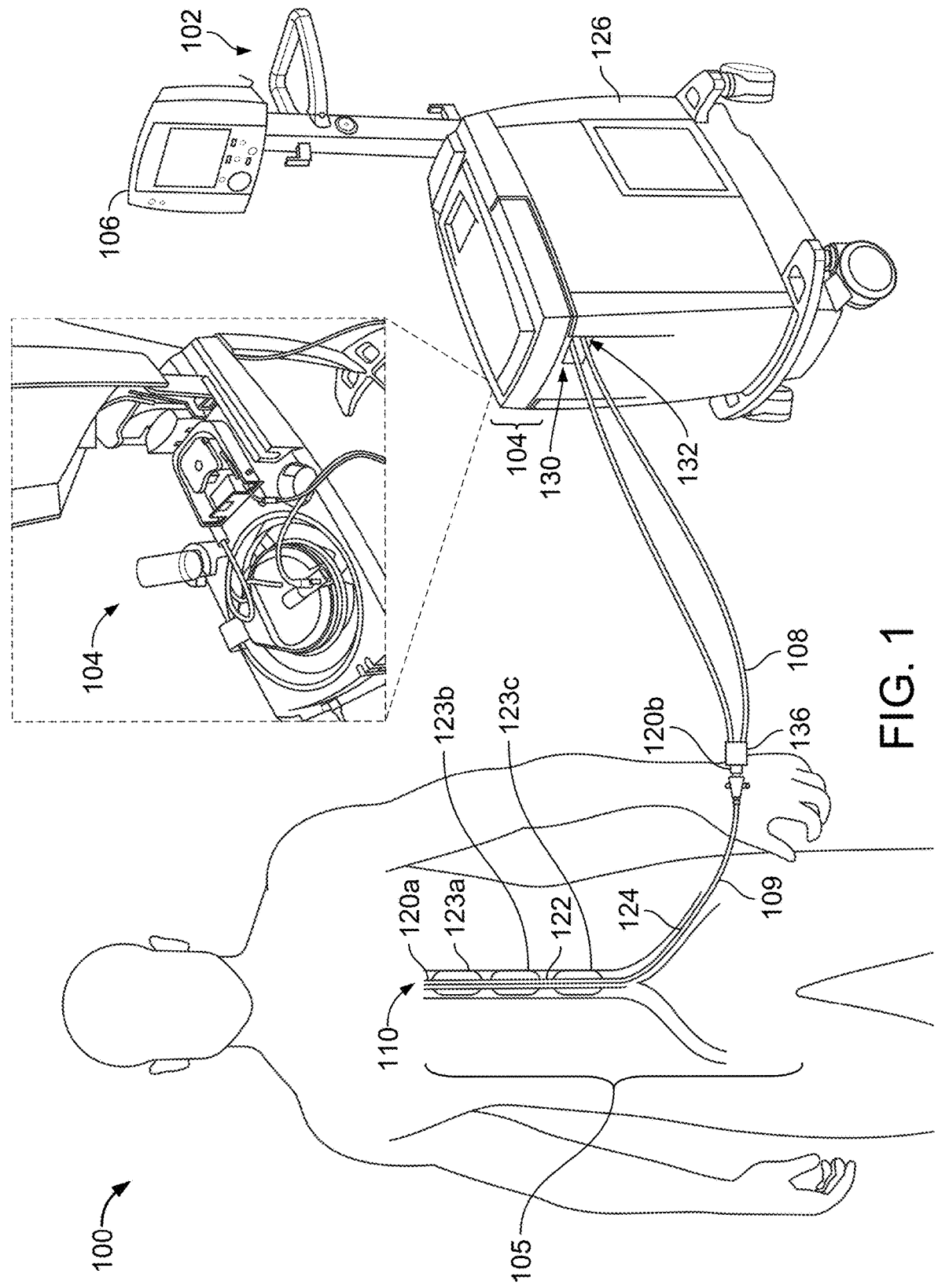
FIG. 1 shows one embodiment of a temperature management system.

Described herein are several temperature management systems for controlling a patient's temperature and providing temperature management treatment or therapy to a patient. The temperature management systems include several advantages and provide several benefits. For example, the system may generate and display a power value. The power value may represent the % power (the percentage of the maximum cooling or warming power capability of the temperature management system for cooling or warming the patient) that the system is delivering to the patient, which tells the caregiver how hard the system is working relative to its total capability at a given patient temperature. The power value may be based on a relationship between the patient temperature and the bath or coolant temperature. Factoring in the patient temperature allows the system to dynamically adjust the calculation of the % power delivered to the patient in relation to the maximum cooling or warming power that the system could possibly deliver to the patient at that particular patient temperature.

In certain implementations, this easy to understand power value may also be an indicator to the caregiver regarding the underlying condition of a patient. For example, a higher % power value may be indicative of a patient experiencing a febrile state or a lower % power value may be indicative of a patient who is not neurologically intact. The system may provide an alert or prompt in response to the system exceeding a % power threshold, which notifies the caregiver of the state of the patient. This allows the caregiver to provide optimal care and treat the patient as needed depending on their status.

In certain implementations, the system may provide a non-graphical visual representation of a patient's treatment history in the form of a treatment log that has several advantages. For example, the visual representation may display multiple symbols (e.g., a mark, character, line, letter, graphical symbol, icon, picture), each representing a different treatment period, on the screen at the same time and also show relative positions of line segments representing the manner in which the system was or is operating, e.g., lowering, raising or maintaining the patient's temperature during various treatment periods. This allows a user to determine how a patient has been treated and where the patient is in the treatment. The treatment log can thus display a representation of any combination of treatment periods. The representation is advantageous because it enables a user to instantly recognize the overall progression of treatment. For example, after a shift change, a new caregiver can arrive in the hospital room, and quickly see the patient's temperature management treatment history on the display screen. Additionally, the treatment log can be represented symbolically as described herein, such that it is clear to the user that the treatment log is not a graph, but rather a series of distinct or segmented icons or symbols representing the manner in which the system has been or is operating, e.g., lowering, raising or maintaining the patient's temperature, over a series of treatment periods, e.g., the four most recent treatment periods in time. This format provides a significant advantage over a graphical representation in that it is simpler and quicker to interpret than a graph. This is important for clinicians who are busy or otherwise experiencing "information overload". It provides an "at a glance" visual which does not include visual distractions present on a graph, e.g. temperature probe shifts due to patient movement. The entries of the treatment log may also be represented using less processing power than that required for rendering a graph.

FIG. 1 shows a temperature management system 100. The temperature management system 100 is configured to control a temperature of a patient's body using a heat exchange device 110. The temperature management system 100 is configured to heat or cool the patient (or both) to manage the temperature of the patient. Managing the temperature of the patient may be referred to as heat exchange treatment of the patient, or heating/warming or cooling treatment of the patient. The temperature management system 100 includes a heat exchange device 1100, e.g., an intravascular heat exchange catheter (e.g., catheters 110a-d of FIG. 3) configured to be inserted into a vasculature 105 of a patient, or a heat exchanger applied to the surface of a patient, such as a heat exchange pad (e.g., pads 110e of FIG. 3). The temperature management system 100 can include other hardware configured for heating or cooling the patient, such as heat exchange fluid loops, heating or cooling plates, heating or cooling cassettes, heat exchange baths, and so forth as subsequently described for heating or cooling the patient (or both). Some of said examples are subsequently described in relation to FIG. 2.

The temperature management system 100 includes an extracorporeal control console with an interface 104, subsequently described. The interface 104 allows the heat exchange device 110 to be coupled to the control console 102 by interfacing with a heat exchange fluid loop that includes the heat exchange device and a tubing assembly as subsequently described. The control console 102 includes a controller and/or processor for controlling the heat exchange device 110. The control console includes a user interface 106 for allowing a user to input data or control signals to the temperature management system 100 and to present information, such as treatment data, indicative of treatment of the patient using the temperature management system 100.

The temperature management system 100 is configured to measure operational data representing operation of one or more hardware aspects of the temperature management system 100 and patient data. The operational data and the patient data that are measured during treatment of the patient may be referred to as treatment data. The temperature management system 100 is configured to measure patient data representing one or more physiological parameters of the patient, e.g., patient temperature, during treatment of the patient. The temperature management system is configured to control the temperature of the patient's body based on the operational data (e.g., pump speed, coolant temperature, and power), and/or patient data, (e.g., patient temperature feedback received from temperature sensors located in or on the patient). The temperature management system 100 is configured to display, by a user interface, an operational status of the temperature management system 100 and a physiological status of the patient during treatment. The operational status can include whether the temperature management system 100 is working at a maximum cooling or heating power (e.g., effort) or a percentage of the maximum heating or cooling power, such as subsequently described in relation to FIGS. 4-7B.

The user interface 106 is configured to display operational data and patient data on the user interface in a configuration that allows a user to determine a stage of a heat exchange treatment (e.g., a treatment cycle or treatment process) being performed on the patient. The user interface 106 shows a current operational treatment period (also called stage). Each treatment period of the heat exchange treatment may be associated with a target patient temperature, a rate of cooling or heating the patient to control the patient temperature to the target temperature, one or more system modes, and/or the system operating to lower, raise or maintain the patient's temperature, e.g., by cooling or warming the patient. The user interface may include a visual representation of the treatment log, the visual representation including one or more sections, where each section corresponds to a treatment period and includes operational and/or patient data for a particular treatment period.

A power value representing the cooling or warming power delivered by the temperature management system 100 to cool or heat the patient is displayed on the user interface 106, as subsequently described in relation to FIGS. 4-7B. The cooling or warming power (also called "effort" or simply "power") represents how hard the temperature management system 100 is working to raise, lower or maintain the patient's temperature, e.g., by cooling or warming. The actual value of the power represents a percentage or fraction of a maximum possible cooling or warming power capability of the system to cool or warm the patient based on a relationship between a bath or coolant temperature of the temperature management system 100 and the patient's current temperature.

The temperature management system 100 is configured to generate log entries for the operational data and the patient data (e.g., treatment data). The log entries may be displayed on the user interface 106. In some implementations, a data message (also called a log message) represents an instant snapshot of the operational data and the patient data. For example, a data message can include a current patient temperature and a current power or heat exchange effort value at a given time (e.g., associated with a time stamp). In some implementations, a data message can include data representing a treatment period or system mode of the heat exchange treatment for the patient in a structured log entry. The data messages are stored in a digital format that enables streaming of the data messages to a remote system. The remote system is configured to quickly extract the values representing the patient data and the operational data of the temperature management system 100 and display a representation of these data on a local or remote user interface. For example, data messages can be formatted for streaming to a nurse's station from a hospital room. In some implementations, data messages can include warnings or alerts that prompt intervention from a user of the remote system. In some implementations, the data messages can be stored in a structured format that facilitates searching and retrieving of treatment data for the patient for one or more instances of treatment by the temperature management system 100.

The processor of the temperature management system 100 is configured to determine, based on the operational data and patient data, e.g., current or measured patient temperature, how hard the temperature management system 100 is working or what fraction or percentage of the maximum cooling or warming power (also called effort) capability of the temperature management system the temperature management system 100 is exerting or delivering to maintain a patient's body temperature at a given value. The values of the operational data provide insight regarding how the temperature management system 100 is operating. The operation of the temperature management system 100, including the heat exchange device of the temperature management system 100, can provide an indication of the patient's thermoregulatory activity. For example, if the heat exchange device is delivering a high level or percentage of cooling power to maintain the patient at normothermia, this may indicate high thermoregulatory activity. In this case, the high thermoregulatory activity, when a high level of cooling power is being delivered to the patient may be indicative of a febrile state (e.g., the patient would have a raised body temperature if the heat exchange device were not cooling the patient's body). Values of the operational data may be indicative of whether the temperature management system 100 is operating at a maximum cooling or warming power or less than a maximum cooling or warming power.

The temperature management system 100 generally comprises an extracorporeal control console 104 and additional hardware for managing the patient temperature. The temperature management system 100 includes, for example, a fluid loop including a heat exchange device 110 (e.g., a catheter and/or other heat exchange devices as subsequently described in relation to FIG. 3), and a tubing assembly 108 which facilitates connection of the device 110 to the control console 102. One or more temperature sensors 120*a*, 120*b* may be located on or in the heat exchange device, and/or may be located on a separate device or probe positioned elsewhere in the body, e.g., in the esophagus or rectum In some implementations, the heat exchange device 1100, and tubing assembly 108 of the fluid loop and/or the temperature sensors 120*a-b* may be disposable items intended for a single use, while the control console 104 may be a non-disposable device intended for multiple uses.

In the embodiment shown, an intravascular heat exchange catheter comprises an elongate catheter body 122 and a heat exchanger 123*a-c* positioned on a distal portion of the catheter body 122. The heat exchanger may be e.g., an inflatable cylindrical balloon, as shown in FIG. 1, or a serpentine or helical balloon or tubing, through which a thermal exchange fluid circulates. Inflow and outflow lumens (not shown) are present within the catheter body 122 to facilitate circulation of the thermal exchange fluid (e.g., sterile 0.9% sodium chloride solution or other suitable thermal exchange fluid) through the elongate catheter body 122. Optionally, the catheter body 122 may also include one or more working lumens 124 which extend through the catheter body 122 and terminate distally at one or more openings in the distal end of the catheter body. Such working lumens may serve as a guidewire lumen to facilitate insertion and position of the catheter and/or may be used after insertion of the catheter for delivery of fluids, medicaments or other devices. For example, as shown in FIG. 1, in some embodiments, the temperature sensors 120a-b may be inserted through the working lumen of the catheter and advanced out of the distal end opening to a location beyond the distal end of the catheter body 122. Alternatively, in other embodiments, the temperature sensors 120a-b may be positioned at various other locations, using a separate device, catheter or probe, on or in the subject's body to sense the desired body temperature(s). Various heat exchange catheters may be used in the embodiments described herein.

Non-limiting examples of other heat exchange devices, heat exchange catheters and/or heat exchange pads or body surface heat exchangers that may be used are described in U.S. Pat. No. 9,492,633, titled Heat exchange catheter and their methods of manufacture and use and issued on Nov. 15, 2016, and U.S. Application Pub. No. 2013/0090708, titled Endovascular Cooling Catheter System Which Employs Phase-Changing Heat Exchange Media and filed on Sep. 28, 2012, U.S. Pat. No. 9,662,243, titled Heat Exchange Catheters with Bi-Directional Fluid Flow and Their Methods of Manufacture and Use and issued on May 30, 2017, U.S. Pat. No. 10,045,881, titled Patient Temperature Control Catheter with Helical Heat Exchange Paths and issued on Aug. 14, 2018, U.S. Pat. No. 9,314,370 titled Self-Centering Patient Temperature Control Catheter and issued on Apr. 19, 2016, U.S. Pat. No. 9,241,827 titled Intravascular Heat Exchange Catheter with Multiple Spaced Apart Discrete Coolant Loops and issued on Jan. 26, 2016, U.S. Pat. No. 9,717,625 titled Intravascular Heat Exchange Catheter with Non-Round Coiled Coolant Path and issued on Aug. 1, 2017, U.S. Pat. No. 9,433,526 titled Intravascular Heat Exchange Catheter With Rib Cage-Like Coolant Path and issued on Sep. 6, 2016, 2018/0185193, titled High Efficiency Heat Exchange Catheters For Control Of Patient Body Temperature and filed on Dec. 30, 2016, U.S. Pat. App. 2018/018519, filed on Dec. 30, 2016, titled Fluid-Circulating Catheters Useable for Endovascular Heat Exchange, U.S. Pat. Application 2018/0325725 entitled Advanced Systems and Methods for Patient Body Temperature Control, filed on May 12, 2017 and 2018/0207024, titled Managing Patient Body Temperature Using Endovascular Heat Exchange in Combination with Body Surface Heat Exchange and filed on Jan. 23, 2017, the entire disclosure of each such patent and application being expressly incorporated herein by reference. Other examples of catheters that may be used include those commercially available from ZOLL Circulation, Inc., San Jose, Calif., such as the Cool Line® Catheter, Icy® Catheter, Quattro® Catheter, and Solex 7® Catheter.

The extracorporeal control console 102 generally comprises a main housing and a console head having a user interface 106. The main housing 126 contains various apparatuses and circuitry for warming/cooling thermal exchange fluid, e.g., coolant, refrigerant, saline, to controlled temperature(s) and for pumping such warmed or cooled thermal exchange fluid through the heat exchange device 110 to effectively modify and/or control the subject's body temperature. The console head includes a display device or user interface 106, such as a touch screen system, whereby certain information may be input by, and certain information may be displayed to, users of the system 100. On the housing 126, there are provided connection ports 130, 132 for connection of additional or alternative types of temperature sensors and/or other apparatuses. A connector 136 can connect the tubing 109 of the tubing assembly 108 from the console 102 to the inflow and outflow tubes of the heat exchange device 110.

Figure 2:
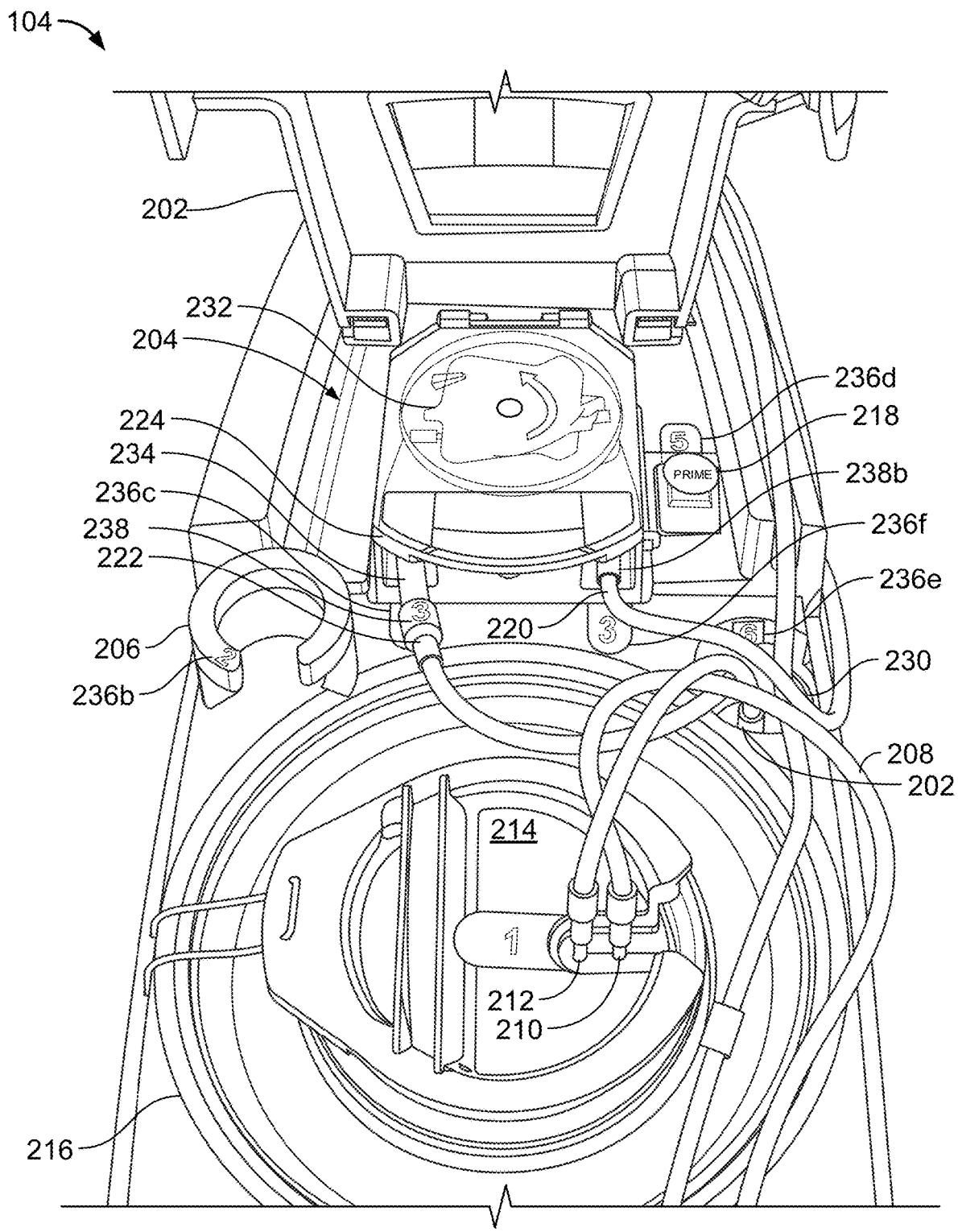
FIG. 2 shows a perspective view of an interface between extracorporeal control console and a heat exchange fluid loop of the temperature management system of FIG. 1.

FIG. 2 shows further detail of the of the console 102, the components of the console that make up the console interface 106 and the manner in which the tubing assembly 108 is inserted in and connected to the control console interface 104. The control console 102 has an openable/closable access cover 202 that enables access to hardware elements of the interface 104. The console interface 104 includes a heat exchange bath 216, an air trap receptacle 230, air trap stand 206, and a pump 204, e.g., a peristaltic pump 204. One or more of the console interface 104 components are configured to engage or couple with one or more components of a heat exchange fluid loop 201 as described in further detail below.

The heat exchange bath 216 is filled with a coolant and is configured to receive a coil (not shown) that is fluidly coupled to the heat exchange fluid loop 201. Working fluid (e.g., saline) is pumped through heat exchange fluid loop 201 and through the coil, which is immersed in the coolant within the heat exchange bath. As the working fluid flows through the coil it is in thermal contact with the coolant and exchanges heat with the coolant, resulting in a cooling or warming of the working fluid to a desired temperature. The temperature of the coolant in the heat exchange bath is controlled by the console, e.g., by exchanging heat with a refrigerant flowing through a refrigerant loop within the console. The coil increases a surface area of the fluid loop 201 that is exposed to the coolant in the heat exchange bath 216 such that the working fluid may be quickly cooled or warmed. A bath cap 214 covers the heat exchange bath 216 to ensure that a desired temperature is maintained in the heat exchange bath. The cap 214 has one or more openings through which an input port 212 and output port 210 of the coil may extend for connecting the coil with tubing 209 of tubing assembly 208.

The heat exchange fluid loop 201 includes an air trap chamber, e.g., an air trap cylinder, which is configured for trapping and removing air from the fluid loop 201 when configuring the temperature management system 100 for heating or cooling the patient. When the fluid loop 201 is primed, the air trap chamber is overturned and positioned in the air trap chamber holder 206. In certain implementations, the air trap holder may be a stand, clip, bracket or other structure configured to hold or secure the air trap chamber. The heat exchange fluid loop 201, including the air trap chamber, is primed prior to operation of the temperature management system by actuating the priming button 218. During operation of the temperature management system, the air trap chamber is positioned in the air trap receptacle right side up.

A pump 204 is configured to pump the working fluid through the fluid loop 201. The pump can be a peristaltic pump that engages a pump tube 234 of the fluid loop 201 and compresses the pump tube 234 to pump the fluid through the fluid loop 201. The pump 204 can be accessed by opening a pump cover 224. The pump cover 224 can be lifted and a pump knob 232 can be turned to advance or load the pump tube 234 onto the pump 204 and/or help unload or remove of the pump tube 234 from the pump 204. The pump tube 234 is connected to the tubing 209 by inlet port 220 and outlet port 222. The pump tube 234 can be a different diameter and made of a different material than the tubing 209. The pump tube 234 is configured for compression and expansion in response to contact by rollers (not shown) of the pump 204. The pump tube 234 is attached to the tubing 209 and is aligned in a raceway of the pump 204 when the fluid loop 201 is installed on the console interface 104. The pump 204 drives fluid flow through the tubing 208, through the air trap chamber, through the coil, and to the heat exchange device 110. The pump 204 is controlled by a controller (not shown) that is configured to control a speed of the pump and thus a rate of the fluid flow through the fluid loop 201. The controller can control a heating or cooling rate of the patient by controlling the temperature of the working fluid and/or a rate of the working fluid flow through the fluid loop 201.

A priming button 218 is provided to prime the fluid loop 201 prior to heating or cooling of the patient. Priming the fluid loop 201 includes removing air from the fluid loop 201 and filling the fluid loop 201 with working fluid. To prime the fluid loop 201, the air trap cylinder is positioned in a first inverted orientation in the air trap holder 206. The priming button is pressed and released to cause the pump 204 to pump working fluid through the fluid loop 201 for a set amount of time (e.g., a minute, two minutes, etc.) to ensure that all air has been removed from the fluid loop 201. The inverted orientation of the air trap chamber causes air bubbles in the fluid loop 201 to be collected in the bottom portion of the air trap chamber (which is now on the top due to the inversion), and eventually forced to a heat exchange fluid source, e.g., saline bag, when the pump is running.

As shown in FIG. 2, markings are provided to assist a user in configuring or initializing the heat exchange fluid loop 201 with the console. The markings (e.g., markings 236a-f) on the console interface 104 can correspond to instructions (not shown) provided to the user for configuring the fluid loop 201. The markings can be color coordinated. For example, the marking 236f of the input port 220 can be a different color than a marking 236c for the output port 224, and these markings 236c can correspond to markings 238 on the tubing 208. This can assist with placement of the pump tube 234 in the pump 204 in the correct orientation. In another example, the marking 236b of air trap stand 206 can be colored to match an end of the air trap chamber to assist with placement of the air trap chamber in the air trap stand in the correct orientation. The markings 236a-f can be numbered (e.g., sequentially) to assist with configuring the fluid loop 201 with the console in the proper orientation for priming of the fluid loop 201 or for operation during heating and cooling treatment.

Figure 3:
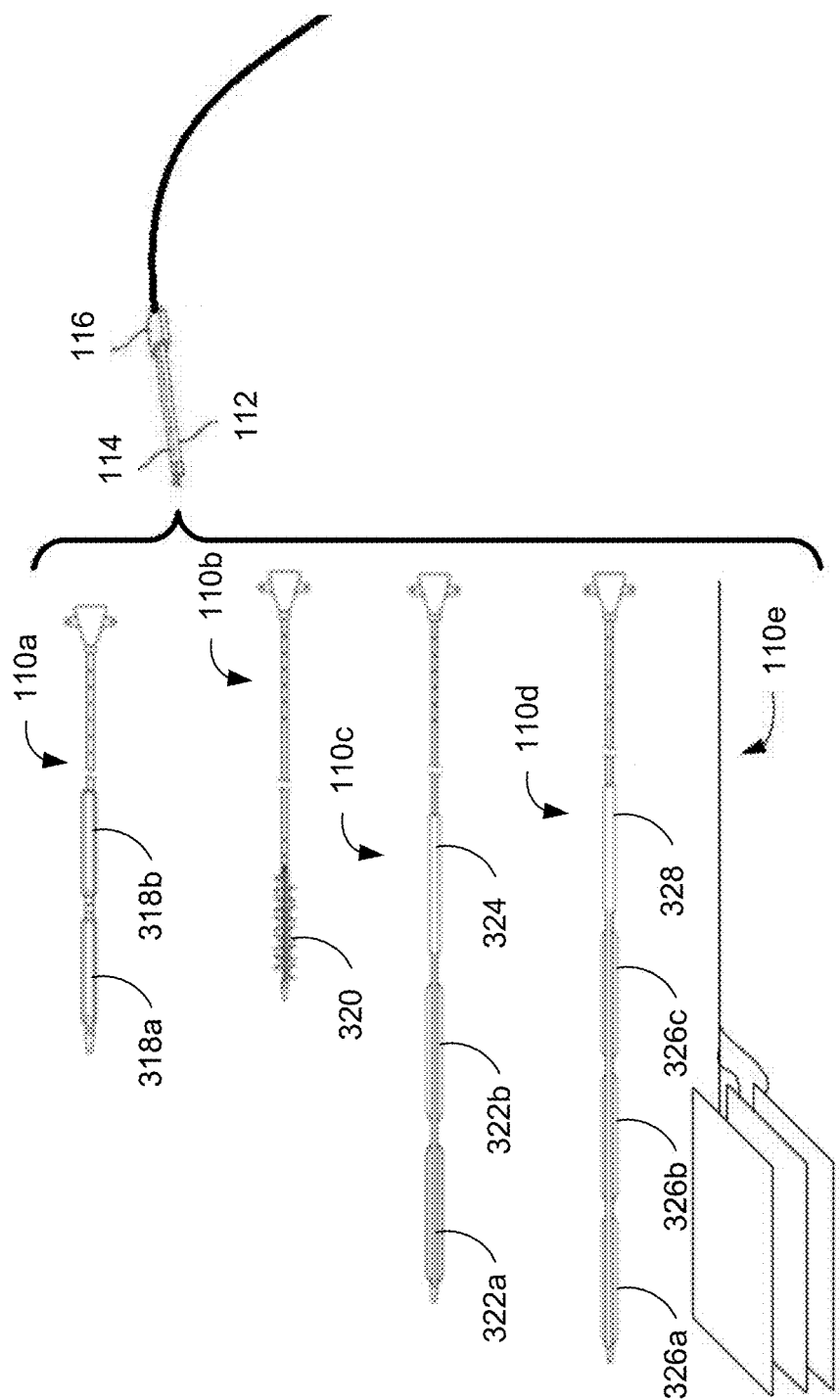
FIG. 3 shows partial views of a plurality of heat exchange catheters or surface pads, any of which may be connected to and used in conjunction with the temperature management system.

Turning to FIG. 3, the console 102 of the temperature management system 100 may be useable or approved for use with a plurality of different types of heat exchange devices 110a-e, such as heat exchange catheters 110a-d or body surface heat exchangers 110e. Body surface heat exchangers 110e can refer to heat exchanging blankets, pads or garments.

The tubing assembly 208 may be connectable to and useable with a plurality of different types of approved heat exchange catheters 110a, 110b, 110c, and 110d, and one or more cooling or heating surface pads 110e. In this particular example, the first approved heat exchange catheter 110a shown in FIG. 3 is commercially available as the Cool Line® Catheter (ZOLL Circulation, Inc., San Jose, Calif.). Catheter 110a includes heat exchange cylindrical balloons 318a, 318b, which can be positioned in the vasculature of the patient, and through which working fluid e.g., saline, circulates to exchange heat with the patient's blood flowing past the balloons in the vasculature of the patient to cool or warm the patient. The second approved heat exchange catheter 110b is commercially available as the Solex 7® Catheter (ZOLL Circulation, Inc., San Jose, Calif.). Catheter 110b includes a serpentine balloon 320 for cooling or warming the patient. The third approved heat exchange catheter 110c is commercially available as the Icy® Catheter (ZOLL Circulation, Inc., San Jose, Calif.). Catheter 110c includes heat exchange cylindrical balloons 322a-b and 324 which can be positioned in the vasculature of the patient, and through which working fluid e.g., saline, circulates to exchange heat with the patient's blood flowing past the balloons in the vasculature of the patient to cool or warm the patient. The fourth approved heat exchange catheter 110d is commercially available as the Quattro® Catheter (ZOLL Circulation, Inc., San Jose, Calif). Catheter 110d includes heat exchange cylindrical balloons 326a, 326b, and 326c and 328, which can be positioned in the vasculature of the patient, and through which working fluid e.g., saline, circulates to exchange heat with the patient's blood flowing past the balloons in the vasculature of the patient to cool or warm the patient. The cooling pads 110e are available as the ZOLL® STx™ Surface Pads (ZOLL Circulation, Inc., San Jose, Calif.). Although these different types of heat exchange devices may have different types of operational data (e.g., different maximum fluid pressure or flow ratings) they may be used with the tubing assembly 208 and form part of the fluid loop 201

In certain implementations, a heat exchange device may be encoded with or may be coupled to a sensing module 116 that is encoded with device identifying information that transmits a signal to or is read by the console processor, and causes the processor to use algorithms and/or operational settings/variables that are specific to the particular heat exchange device 110a-e, e.g., catheter type, or body surface device (e.g., pad or garment). For example, the encoded information may include, or cause the console processor to select and use, algorithms and/or operational settings or data that are suitable for any of the heat exchange catheters 110a-110d and the one or more cooling or heating surface pads 110e. Specifically, the encoded information may include the particular algorithms and/or operational settings or data to be used, or alternatively the console processor may be pre-programmed with a number of different algorithms and/or operational settings or data and may be further programmed to select and implement, on the basis of the encoded data, the algorithm and/or operational settings or data suitable for the heat exchange devices that are useable or approved for use with tubing assembly and/or the console 102. For example, in certain embodiments, each of the plurality of approved heat exchange devices 110a-e, may have a recommended pressure limit and the encoded information may include, or cause the processor to select and use, a control algorithm, operational setting or data that limits the speed of the pump 204 such that heat exchange fluid pressure within the heat exchange device 110a-e connected to the tubing assembly 208 will not exceed a maximum pressure limit for that heat exchange device, irrespective of which of the plurality of heat exchange device types is connected to the tubing assembly 208.

A temperature management system with extracorporeal control console 102 configured to interface with fluid loop 201 includes one example of a temperature management system 100 having a processor or controller configured to carry out the processes described herein. ZOLL's Thermogard XP® intravascular temperature management system is another example. Other temperature management systems, e.g., other intravascular heat exchange systems and/or heat exchange systems that provide surface cooling and/or warming may also be configured to carry out the processes described herein.

The temperature management system 100 is configured to control the body temperature of the patient, as previously described. The processor (e.g., a system controller) of the console of the temperature management system 100 receives values of one or more patient data and/or operational data from one or more sensors of the temperature management system 100 as the patient's body temperature is changed by the heat exchange device.

The one or more sensors for measuring patient data may include a temperature sensor, e.g., a thermistor or thermocouple or temperature probe, positioned on or in the patient. The one or more sensors for measuring the operational data of the temperature management system 100 can vary depending on the hardware configuration of the temperature management system 100 and depending on the operational data being measured. For example, the sensors can include one or more temperature sensors (e.g., thermistors), a fluid flow rate sensor or flow meter, a pressure sensor, e.g., pressure transducer or monometer, an ammeter or other sensor for measuring power consumed by one or more components of the temperature management system 100, a tachometer or other sensor for measuring pump rotations per minute (RPM) or pump impeller speed, and so forth for measuring the values of the operational data. Some operational data can be determined indirectly, such as determining cooling energy or power delivered by the heat exchange device by measuring patient and heat exchange bath temperatures using temperature sensors, or by measuring a change in working fluid temperature $T_{in}$-$T_{out}$ (where $T_{in}$ is the temperature of working fluid flowing into a heat exchange catheter and $T_{out}$ is the temperature of the working fluid flowing out of the catheter) during operation of the temperature management system 100 via temperature sensors located in the catheter inflow and outflow lumens or in inflow and outflow lumens of the tubing assembly.

The temperature management system may include a processor, a memory, and associated circuitry coupled to the one or more sensors for detecting operational or patient data. The operational and patient data are collected and/or stored in the system for retrospective, current or other review. For example, the operational and patient data can be stored as log entries. In certain implementations, the log entries can each be structured messages that include particular values associated with the heat exchange treatment, generated from data messages. For example, the data messages can indicate a current snapshot of the operation of the temperature management system 100. In this case, the values of the data message include a list of operational values (and in some implementations, patient temperature data). The operational values can be parsed from the data messages (e.g., by a remote device) and used to populate a screen or display of a remote computing system. For example, the temperature management system 100 can transmit a stream of data including the data messages to a remote system for remote monitoring of the operation of the temperature management system 100. In some implementations, the processor is configured to stream digital output data having the patient temperature data and the operational data to a remote server. In some implementations, operational and patient data may be transmitted or streamed in real time or near real time via a wired, RS-232 streaming output on the system console to a remote processor or computer, e.g., to an EMR data hub or hospital hub. In some implementations, operational and patient data may be transmitted or streamed in real time or near real time over a WiFi communications, Bluetooth, cellular, USB or other wireless connection or link.

The data messages can include summary data (also called log entries). A log entry can include data representing a summary of temperature management treatment performed during a treatment period. Each log entry may form all or a portion of a treatment log, which provides an overall summary of the temperature management treatment of a patient. The treatment log allows a medical service provider to quickly review the summary of the temperature management treatment. The operational and patient data, e.g., data messages, log entries, treatment log and/or other data, stored by the system processor or an accessary to the system e.g., a HMIA (Hospital Monitor Interface Accessory) or data module, coupled to the system console, may be stored on volatile or non-volatile memory. The log entries can be visually represented on the user interface 106, as subsequently described.

Data messages may provide instant values of operational data of the temperature management system 100 and the patient data. Log entries may represent data gathered over time and can be part of a patient profile. For example, the treatment log and the log entries can be stored in electronic medical records (EMR).

For example, a log entry of the one or more log entries may include data representing one or more of a cooling or warming rate applied during a treatment period, a target patient temperature value, a name of the treatment period, a time period associated with the treatment period, a patient temperature at the start, end or during the treatment period, and a position of the treatment period relative to one or more other treatment periods for the temperature management treatment of the patient. The log entry for each treatment period can include a system mode identifier, a time for which the treatment period was active, and other data (such as a patient temperature, maximum patient temperature, minimum patient temperature, change in patient temperature, target temperature, cooling or warming rate, etc.) associated with the treatment period. In some implementations, the log entry can include a total heating or cooling energy or power associated with the treatment period. Display of the log entries is described in relation to FIGS. 4-6.

In some implementations, the log entries of the treatment log are transmitted to a remote device (such as a data hub in a hospital). The temperature management system 100 sends the data including the log entries to the remote device in one or more different ways. The temperature management system 100 sends the log entries data to a remote device in response to a trigger. For example, the temperature management system 100 can send the log entries to the remote device once a treatment period is completed, even if treatment is still ongoing in a different treatment period. In some implementations, the temperature management system 100 sends the treatment log data once all temperature management treatment is completed. For example, when the heat exchange device of the temperature management system 100 is deactivated or powered off, a controller can determine that treatment is completed and send the log entry data to the remote device. In another example, the temperature management system 100 sends the treatment log (or one or more entries of the treatment log) to a remote device upon detecting a change in a system mode (e.g., the cooling or warming of a patient in MAX mode, the cooling or warming of a patient in RATE mode, the maintaining of a patient's temperature in MAINT (MAINTAIN) mode, etc.).

In some implementations, the temperature management system 100 sends the treatment log data to the remote device upon detecting a fault, such as an air trap fault, a heat exchange device fault, a patient temperature exceeding a threshold value, etc. The treatment log data can be analyzed (e.g., by a user) to determine why the fault occurred and/or to determine whether treatment is adversely impacted by the fault. This enables the user to take corrective measures immediately (e.g., replacing an air trap, fixing a fluid leak, etc.) to ensure that the temperature management treatment of the patient is not compromised.

In some implementations, the temperature management system 100 sends the treatment log data without a trigger. For example, the temperature management system 100 can send the log entry data to the remote device periodically (e.g., once per hour, once per day, etc.).

In an aspect, the temperature management system 100 links the log entries related to a given treatment together in a structured format. For example, a key value can be stored with each log entry. The entire log of the treatment of the patient can be retrieved by referencing the key value.

The temperature management system 100 can generate one or more alerts to indicate a status of the patient, a status of one or more components of the temperature management system 100, or a combination thereof. The alerts can be generated based on the treatment log data or data of the data messages. The alert can be generated for presentation on a user interface of the temperature management system 100. The processor may send the alert to one or more other computing devices, such as computing devices associated with a health care provider of the patient. In an aspect, a user interface is configured to communicate with the processor, wherein the data representing the alert indicating whether a fault has occurred, a stage of treatment has initiated/completed, or any other relevant aspect of the treatment of the patient that satisfies a notification rule causes a notification to be displayed on a user interface. The user interface may be coupled to the console via a wire or wirelessly (e.g., the user interface may be a portable tablet or remote computing device)

The alert may indicate that there is a fault or error in operation of the temperature management system 100. The alert provides an indicator for a health care provider to investigate the operation of the temperature management system, such as to investigate whether any faults have occurred. The alerts may indicate that treatment has completed, that a first treatment period has ended and a second treatment period has commenced, that there has been a change in mode, e.g. from MAX to MAINT, or that operation of the temperature management system 100, e.g., the percentage or fraction of the maximum cooling or warming power capability of the temperature management system at a patient's measured or current temperature being exerted or delivered by the temperature management system, is indicative of a clinical state or underling condition of the patient, e.g., a febrile state.

In some implementations, the processor generates the alert to cause one or more devices to perform an action. For example, feedback can be presented to a healthcare provider, such as an audio cue, visual presentation, and so forth. The alert can cause a device to contact a healthcare provider (e.g., place a phone call or page to a physician, nurse, etc.). The alert can cause a device to display particular data about the patient, such as a presentation of the patient's temperature over a given treatment period. The alert can cause a device to update a health record associated with the patient or cause the device to retrieve a health record associated with the patient for further analysis. In certain implementations, the processor of the system may be configured to determine if the alert is a real time alert or recorded for retrospective review. If it is a real time, the processor determines whether to display the alert on the user interface, transmit the alert in an information chain, or send the alert data to a third-party monitor. An example route is to send the alert to a physician or nurse's cell phone.

The alert may open a cell phone-based application or open an Internet-based application. From either application the physician or nurse could see the alert plus other relevant data that may have been transmitted. The alert may include a hospital specific patient identifier, but otherwise be invisible as to the identity of the patient, unless the physician or the hospital has added the patient name to either the application on their phone or to the Internet. The alert may include a non-patient specific identifier such as a bed number. Additionally, the physician would have the opportunity to take actions in response to receiving the alert. This might include triggering a phone call to the ICU desk, adjusting the temperature change range or duration of the change on the alert (in the application or remote to the temperature management system) or marking that the physician has seen the alert. Changing the duration or range would allow the user to set a duration so that a transient spike would not trigger the alert. For example, a deviation of 0.4 C sustained for five minutes might trigger an alert, while a pause in therapy would disable this alert—but could trigger a different alert. In the case of adjusting the time and/or duration of the alert, such an adjustment may only affect the notification to that specific person. For example, adjusting the temperature change alert range from a 0.4 C temperature change to a 0.5 C temperature change, but leaving the duration the same may affect whether the application sounds a tone/alert on that physician's specific application or web-based program.

A dual alert to a nurse or physician might have different alert ranges and actions. The described features may put the user, e.g., physician in complete control. For example, the first point of control may be at the bedside, where the alert ranges may be set. The second point of control may be at the receiving application or website where the user may adjust nominal settings, e.g., for "tones". As such, two or more triggers may be established: the first is to "send" the alert from the machine into the network to the receiving device; and the second is the action that the receiving device takes upon receiving the alert. A scheduling feature may also be provided that allows for the transfer data from one physician going off shift to another coming on shift. A response tree may be provided that requires an acknowledgement that the alert has been seen or transferred from one physician to another. For example, a first doctor is given 5 minutes to acknowledge receipt of the alert, and if no acknowledgment is made, the alert is sent to another physician or nurse. In certain implementations, one or more of the various alerts or alert parameters described herein may be customized by the user. Multiple options for alert delivery, e.g., device display, nurse's station, EMR, cell phone, etc. may be set. An alert for thermoregulatory activity of a patient may include other forms. For example, a color scale or audible alert may be output via the user interface to provide a value indicative of thermoregulatory activity.

Figure 4A:
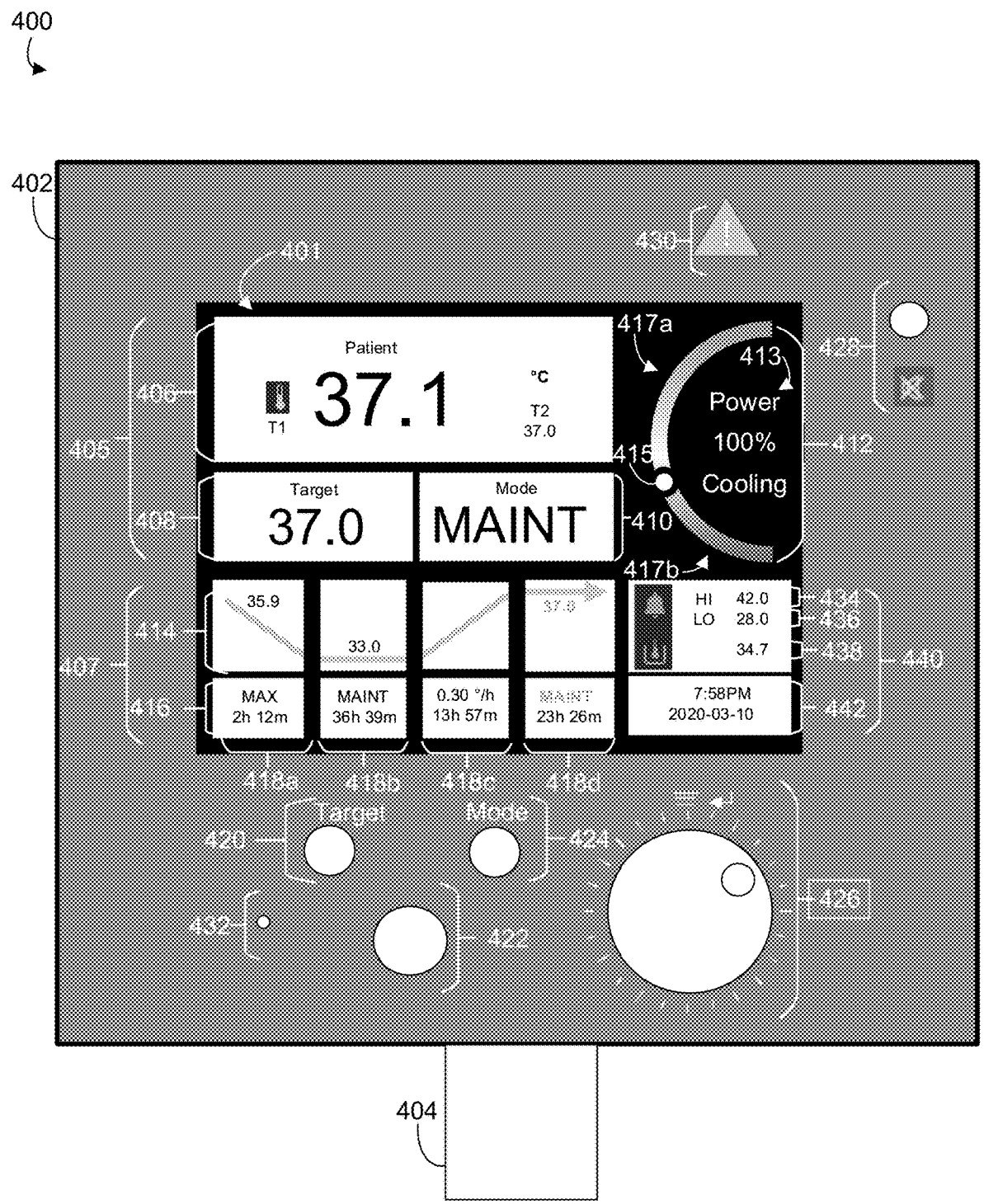
FIG. 4A is an example of a user interface showing data presented during or after operation of a temperature management system such as the systems of FIG. 1, FIG. 2, and FIG. 3.

FIG. 4A shows an example illustration of a user interface 400 (like user interface 106 in FIG. 1). The user interface 400 includes a housing 402 and a mount 404. The housing includes hardware for enabling operation of the display 401 and one or more hardware controls 420, 422, 424, 426, and 428, subsequently described. The housing 402 includes hardware for one or more indicators, such as indicators 430 and 432, which are configured to activate to provide signals to a user. The user interface includes a display 401 configured to show visual representations of treatment data generated during treatment by the temperature management system 100. The mount 404 allows the user interface to be moved or pivoted in relation to the rest of the temperature management system 100. For example, the mount 404 can include a telescoping system for moving the user interface 400 up and down. In certain implementations, the user interface may be detachable from the console or portable. For example, the user interface may be in the form of a tablet, phone or other portable device that may communicate with the console via wireless connection.

The display 401 is configured to show a representation of the treatment data in one or more graphical configurations. The screen 401 includes a region 405 that shows treatment data relating to the active or current treatment of a patient by the temperature management system. For example, the region 405 includes patient data, such as temperature data 406.

The patient temperature data 406 includes the body temperature of the patient in the present time (e.g., the instant patient temperature, the current patient temperature, etc.). The temperature data 406 is measured by a temperature sensor in or on the patient. The temperature sensor can be a part of a heat exchange device, such as a catheter, or be positioned on separate probe or catheter. The patient temperature data 406 may include temperature measurements from two distinct temperature probes, T1 and T2. In FIG. 4A, T1 is measuring 37.1° C., and T2 is measuring 37.0° C. The probes T1 and T2 may be located in different positions in the patient. The second probe T2 is included to increase robustness of the temperature measurement of the temperature management system 100. For example, if probe T1 fails, then probe T2 ensures that the patient is not warmed or cooled based on wrong temperature data. For example, if a difference between the values shown by T1 and T2 exceeds a threshold difference, an alert is generated to prompt intervention from a user and/or safely cease temperature treatment of the patient.

The display 401 is configured to show a representation of a target temperature 408 for the patient in the current treatment data region 405. The target temperature 408 represents a temperature that the temperature management system 100 is configured to cause the patient to have either by warming the patient or cooling the patient using the temperature management system 100. The target patient temperature 408 can include a point temperature (e.g., 37° C.). In some implementations, the target patient temperature 408 includes a temperature range (e.g., 36.8° C.-37.2° C.). The target temperature 408 is displayed as a point temperature or a temperature range. The temperature management system 100 may warm or cool the patient above or below the target temperature or maintain the patient temperature 406 within a range of the target temperature 408.

The display 401 is configured to display a current system mode identifier 410 of the temperature management treatment that is being currently applied to the patient. The mode identifier 410 identifies how the temperature management system 100 is operating for treating the patient. For example, each mode can have a different goal or purpose for treatment.

A "MAX" mode or MAX power mode of the temperature management system 100 is configured to cause a heat exchange device 110 to warm or cool the patient as fast as possible given the hardware of the temperature management system 100. The power of the temperature management system 100 is generally 100% during a maximum power mode. This includes the fastest rate of heating or cooling by operating the hardware of the temperature management system 100 at capacity. For example, a pump that pumps heat exchange fluid can be set to a fastest pump setting to circulate as much fluid as possible, as permitted by safety constraints. In another example, a heat exchange bath temperature (e.g., a coldwell temperature) can be reduced to a coldest temperature available for the temperature management system 100. In another example, heating or cooling elements (such as heat exchange plates) can be set to maximum allowable temperatures or minimum allowable temperatures. In another example, backup heating or cooling elements (e.g., fans, electric heaters, etc.) can be activated to supplement a main heating or cooling element. Other such examples are possible. The temperature management system 100 thus heats or cools the patient as fast as possible until a threshold temperature or some offset from a threshold temperature (e.g., 0.5 degrees) is reached. This threshold temperature can be indicated by the target temperature 408, or can be a different value from the target temperature to prevent overshooting (e.g., heating or cooling too much) the desired final temperature of the patient. In certain implementations, once the threshold or threshold offset temperature is reached, the system may automatically transition into "MAINT" mode (described in more detail below) and the user interface would display MAINT.

A "MAINT" or maintain mode of the temperature management system 100 is configured to cause the temperature management system 100 to maintain the patient temperature 406 at a steady value (e.g., the target temperature 408) or within a threshold amount of the steady value. In the maintain mode, the temperature management system 100 can be configured to use any power percentage available to heat or cool the patient to maintain the target temperature. For example, the temperature management system 100 can control the heat exchange device 110 to heat the patient with increased power when the difference between the target temperature and the patient temperature is increased. When the difference between the patient temperature and the target temperature is relatively small (e.g., decreased), the temperature management system 100 controls the heat exchange device 110 to heat or cool the patient at a relatively decreased power (or zero power).

A controlled RATE or set RATE mode of the temperature management system 100 is configured to cause the heat exchange device 110 to heat or cool the patient at a specified rate. This rate may be input by the user. The rate can be designated in degrees per unit time, such as ° C./hour. In this example, the temperature management system 100 raises or lowers the patient temperature 406 at a rate that is as close to the specified rate as possible. In some implementations, the rate of cooling or heating is applied to the patient for a specified amount of time. In some implementations, the rate of cooling or heating the patient is applied until a target or threshold patient temperature is reached or some offset from a target or threshold temperature (e.g., 0.5 degrees) is reached. In certain implementations, once the threshold or threshold offset temperature is reached, the system may automatically transition into "MAINT" mode and the user interface would display MAINT.

A "FEVER" mode of the temperature management system is configured to set the heat exchange bath temperature to a coldest temperature available (e.g., 0.5 degrees C.) to cause a heat exchange device 110 to cool the patient as fast as possible given the hardware of the temperature management system 100. Once the patient reaches the target or threshold temperature, or some offset from a target or threshold temperature (e.g., 0.5 degrees) is reached, the pump shuts off. The temperature management system waits to see what the patient's temperature does. If the patient temperature rises above some preset threshold (0.01-0.05 degrees C.), the pump turns back on and the system continues to operate in FEVER mode. In some implementations, in FEVER mode, the system will only operate to reduce the patient's temperature or cool the patient, and will never operate to raise the patient's temperature or warm the patient.

While several modes have been described, other modes are possible. For example, the temperature management system 100 can apply heating cycles, preprogrammed heating and/or cooling regimes with respect to time, and so forth independent of the above described modes.

Continuing with FIG. 4A, a region 407 represents a treatment log. The region 407 includes historical data related to the treatment of the patient by the temperature management system 100. For example, the region 407 can display a representation of the treatment previously administered and/or currently administered to a patient, where the treatment is broken down into a series of treatment periods 418a-418d, where each treatment period is displayed in a separate section or tile in region 407 of the display or screen. One or more treatment periods may include one or more previous modes of treatment that were applied to the patient during that period, the current mode being applied to the patient, and/or future modes of treatment to be applied to the patient. In certain implementations, one or more target temperatures, patient temperature at the start, during, or at the end of a treatment period, heating or cooling rates applied to the patient, time durations associated with each mode or treatment period, time stamps associated with each mode or treatment period, a treatment schedule, or any combination thereof may be displayed. In certain implementations, each treatment period or section may be associated with a target temperature. Region 407 in FIG. 4 shows various treatment symbols 414, e.g., a sequence of symbols (e.g., a mark, character, line, letter, graphical symbol, icon, picture), which provide a symbolic representation of the intended direction or direction of the patient's temperature, or the manner in which the system was or is operating, e.g., operating to lower, raise or maintain the patient's temperature, during a particular treatment period, e.g., by cooling, warming or heating the patient. For example, a symbol 414 may represent the intended direction of the patient's temperature during each treatment period 418a, 418b, 418c, and 418d. In certain implementations, the symbols 414 may represent how the temperature management system 100 was operating, is operating, or will operate during the treatment of the patient, e.g., lowering, raising or maintaining the patient's temperature. In certain implementations, the symbols 414 may represent how the temperature management system 100 was operating, is operating, or will operate during the treatment of the patient, e.g., cooling or warming the patient's temperature.

The treatment periods 418a-d may include text data 416 that indicates the system mode identifiers, e.g. MAX, and/or time periods associated with each treatment periods. For example, the data 416 shows how long each of the modes was applied to the patient or is scheduled to be applied to the patient, or how long the patient's temperature was cooled, warmed, maintained or driven in a particular direction e.g., toward a higher or lower temperature, as indicated by the symbols 414. In this example, the lighter text used in treatment period 418d indicates that this treatment period is currently being executed by the temperature management system 100 to treat the patient, and corresponds to data in the current treatment region 405.

During the first treatment period 418a the temperature management system was operating in a MAX cooling mode, to reduce the patient's temperature, and so a downward sloping or angled line is presented to represent that the system was lowering the patient temperature or was operating in a manner to lower the patient's temperature over that treatment period. The number shown near the line indicates the patient's temperature when the treatment period was initiated. Here, that value was 35.9° C. The text data 416 below the symbol indicates that the cooling or system operating in a manner to lower the patient's temperature lasted for 2 hours and 12 minutes (2 h, 12 m). In certain implementation, the patient's temperature at the beginning, during or end of a treatment period and/or a target temperature may be shown for any of the treatment periods in one or more of the display sections or tiles.

During the second treatment period 418b the temperature management system was operating in a MAINT mode (or maintain temperature mode). A flat line symbol is presented to represents that the system was maintaining the patient temperature or operating in a manner to maintain the patient's temperature at 33.0° C., over that treatment period. The text data 416 indicates that the maintaining or system operating in a manner to maintain the patient's temperature lasted for 36 hours and 39 minutes. The MAINT mode does may not show the specifics of how the patient was heated or cooled during that time period. The temperature management system 100 may cool or heat the patient at a low power during the MAINT mode, depending on whether the patient temperature is being elevated or lowered from the natural body temperature for treatment.

During the third treatment period 418c the temperature management system was operating in a RATE mode. An upward sloping or angled line is presented to represent that that the system was raising the patient temperature or operating in a manner to raise the patient's temperature over the treatment period. In this example, the system was operating at a controlled rate to raise, e.g., by heating or warming, the patient's temperature to a target temperature of 37.0° C. from 33.0° C. The text data 416 indicates that the rate was 0.30° C./hour and the raising or system operating at a controlled rate of 0.30° C./hour to raise the patient's temperature lasted 13 hours and 57 minutes.

During the fourth treatment period 418d the temperature management system was operating in a MAINT mode. A flat line symbol is presented to represent that the system was maintaining the patient temperature or operating in a manner to maintain the patient's temperature at 37.0° C., over that treatment period. The text data 416 indicates that the maintaining or system operating in a manner to maintain the patient's temperature has lasted for 23 hours and 26 minutes, so far. The lighter text, which corresponds to the text of the current treatment region 405, indicates that the treatment period is active and ongoing. The time period of the text data 416 shows the elapsed time for this current treatment period.

The display 401 shows a power meter 412. The power meter 412 is configured to show a warming or cooling power value 413 representing how hard the temperature management system 100 is working to cool or heat the patient during treatment. The power value 413 is a function of one or more operational parameter values of the temperature management system 100 and one or more values of patient data (such as patient temperature). For example, the function relates the current values of the one or more operational parameters to maximum values possible for the respective one or more operational parameters. For example, power value 413 can be based on a ratio between a first value representing a difference between a patient temperature (at present) and a bath or coolant temperature and a second value representing a difference between the patient temperature and a maximum bath or coolant temperature value.

The function can be shown as Equation (1):

$$\text{Power value} = \left| \frac{T_{patient} - T_{bath}}{T_{patient} - T_{bath\_max}} \right| \qquad (1)$$

where Power value is the power value 413 as a percentage, $T_{patient}$ is the patient's current temperature, $T_{bath}$ is the current bath or coolant temperature, and $T_{bath}$ max is the maximum bath or coolant temperature (which can be a proxy for the heat exchange fluid temperature). The maximum bath or coolant temperature is the highest bath or coolant temperature possible when heating the patient and the lowest bath or coolant temperature possible when cooling the patient. When the denominator of Equation (1) approaches zero, the power value is set to 100%.

Generating and displaying a power value or value as a percentage of the maximum cooling or warming power capability of the temperature management system to cool or warm the patient, where the power value is based on a relationship between the patient temperature data and the coolant temperature data as described herein has many advantages. The power value lets the caregiver know how hard the system is working to raise, lower or maintain the patient's temperature. In certain implementations, the power value may represent % of the cooling or warming power (the percentage of the maximum cooling or warming power capability of the temperature management system for cooling or warming the patient) that the system is delivering to the patient, which tells the caregiver how hard the system is working relative to its total capability at a given patient temperature. The percent cooling or warming power or effort value is a ratio that communicates how hard the system is working relative to its full capability. The power value or effort value represents a percentage of the system's max cooling or warming capability to cool or warm a patient. The power value or effort value may be a unitless value. As described supra, the power value may be based on a relationship between the patient temperature and the bath or coolant temperature. Factoring in the patient temperature allows the system to dynamically adjust the calculation of the % power delivered to the patient in relation to the maximum cooling or warming power that the system could possibly deliver to the patient at that particular, current or measured patient temperature. Factoring in the patient temperature as shown in the above calculation is important because without the patient temperature, the system's cooling or warming power capability relative to the state of the patient cannot be determined. The difference between the patient temperature and the bath temperature provides the temperature gradient between the patient and the bath. The higher the gradient the higher the power transfer or rate of energy transfer between the patient and the bath. If the patient temperature is not taken into account, only the % power that the system is capable of delivering under pre-defined fixed conditions, having nothing to do with the patient being treated, would be known, rather than calculating the % power the system could actually transfer to the patient in practice. Without the patient temperature, the equation is not adjusted to account for the current condition of the patient, and the % power that can actually be transferred to the patient at the actual measured current patient temperature would not be determined. In the above power calculation, the numerator represents how hard the system is working, while the denominator represents how hard the system could possibly work. The calculated value tells the caregiver how hard the system is working relative to its total capability.

In some implementations, this easy to understand power value may also be an indicator to the caregiver regarding the underlying condition of a patient. For example, a higher % power value may be indicative of a patient experiencing a febrile state or a lower % power value may be indicative of a patient who is not neurologically intact. The system may provide an alert or prompt in response to the system exceeding a % power threshold, which notifies the caregiver of the state of the patient. This allows the caregiver to provide optimal care and treat the patient as needed depending on their status.

Figure 4B:
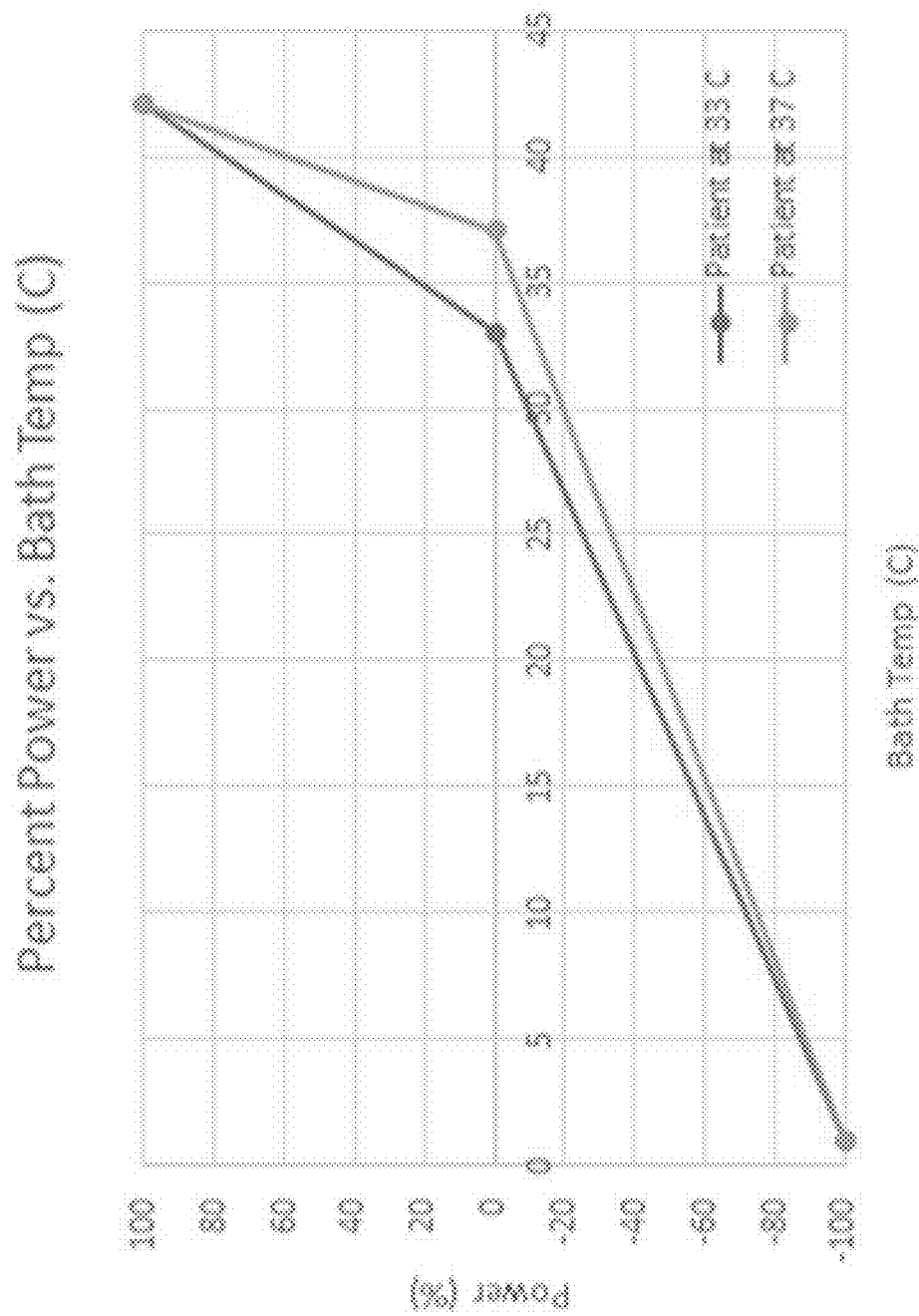
FIG. 4B is a graph showing power output for bath temperatures.

FIG. 4B shows a graph 450 below includes two examples of patients: one at 33 C, another at 37 C. If the patient is at 33 C, and the bath or coolant is 35 C, the system is warming at 20% of its max capability. If the patient is at 37 C, and the bath or coolant is 35 C, the system is cooling at 8% of its max capability. In some implementations, a value of the ratio is zero if a working fluid pump of the temperature management system 100 is turned off. In some implementations, when a working fluid pump of the temperature management system 100 is on, a value of the ratio is based solely on the bath temperature (e.g., coolant temperature) and the patient temperature. In some implementations, the power value 413 ratio is further based on a speed of a working fluid pump of the temperature management system. In some implementations, the ratio is not based on a speed of a working fluid pump of the temperature management system but is calculated independent of a pump speed of the fluid pump and based solely on the patient and bath or coolant temperatures as described supra. For example, in certain examples, a variable pump speed is not factored into the above referenced calculation. In some implementations, the ratio is based on a power (e.g., energy over time) consumption of the temperature management system. This can be measured in Watts. In some implementations, the value indicative of cooling or warming power 413 of the temperature management system and the coolant temperature for the one or more periods of a heat exchange treatment are displayed simultaneously on a single screen 401 of the user interface 400.

Returning to FIG. 4A, the power value 413 can be displayed on the display 401 along with a text indicator of a cooling or warming state of the temperature management system 100. For example, when the temperature management system 100 is cooling, the word "Cooling" is shown. For example, when the temperature management system 100 is warming, the word "Warming" is shown.

The power value 413 can be displayed as a single number. The number can include a percentage, a fraction, a number on a meter, or any similar format. In some implementations, the power is represented by a contextual phrase, such as "maximum power," "low power," "high power," and so forth.

The power value 413 can be displayed near the power meter 412. The power meter 412 includes a visual representation of the warming or cooling power of the temperature management system 100 at present. The power meter 412 can include an arcuate meter. The power meter 412 can be divided into two regions: a warming region 417a and a cooling region 417b. The regions 417a-b can be different colors (e.g., red for warming and blue for cooling). The warming region 417a can be above the cooling region 417b on the display 401. The regions 417a-b can meet near a center representing 0% power for the temperature management system or a state of the temperature management system 100 wherein the temperature management system is not heating or cooling the patient. The end at the top of the warming region 417*a* represents 100% warming power. The end at the bottom of the cooling region 417*b* represents 100% cooling power. In this way, the warming region 417*a* represents 0-100% warming power for the temperature management system. In this way, the cooling region 417*b* represents 0-100% cooling power for the temperature management system. In some implementations, the center region represents an OFF state for the pump of the temperature management system 100 or one or more other components. In some implementations, the center region represents a situation in which the patient temperature and bath temperature (e.g., coolant temperature) have equalized to a same temperature, and the power value 413 is zero. An indicator 415 is configured to slide around the power meter in real time as the percentage or fraction of the maximum cooling or warming power capability of the temperature management system, e.g., at the current or measured patient temperature, exerted or delivered by the temperature management system to cool or warm the patient changes and/or as the patient temperature 406 and/or bath temperature changes.

The user interface 400 includes indicators for treatment parameters in a region 440. The treatment parameters can include threshold values such as a high temperature threshold 434 and a low temperature threshold 436. The threshold values 434 indicate patient temperatures for which an alert is generated. The alert may be sent to a remote computing device (e.g., to a mobile computing device of a doctor or nurse or to a nurse station). The alert can indicate that the patient temperature is too high or too low for the treatment. In some implementations, when the patient temperature passes one of the threshold values 434, 436, an alarm is sounded directly from the temperature management system 100 or an alert, e.g., a light, is displayed on the user interface. In this example, the low threshold value is 28.0° C. and the high threshold value is 42.0° C. A bell (or other symbol) indicates that these are alarm or alert thresholds.

The treatment parameters of region 440 can include a representation of a bath temperature 438. The bath temperature 438 represents the current temperature of a heat exchange fluid (e.g., a coolant or heating fluid) circulating through the heat exchange device to cool or warm the patient. A thermometer in a container (or other symbol) indicates that this is the bath temperature value. The bath temperature value is measured by a temperature sensor (e.g., thermocouple or thermistor) placed in the bath reservoir of the fluid loop of the temperature management system 100. In this example, the bath temperature value is 34.7° C. The bath temperature and the patient temperature can be displayed simultaneously on the screen 401 during treatment in addition to the power value 413.

The region 442 displays the present date and time values. The date and time are used to determine the time periods associated with the treatment periods 418*a-d*. The date and time values can help a user determine what mode of treatment the patient should be experiencing or how the patient's temperature should be affected by the system. The date and time values are used in the log messages to timestamp the log messages. In certain implementations, the total elapsed time of temperature management treatment may be displayed.

The user interface 400 includes one or more hardware controls. The controls can include target temperature control 420 for setting the target temperature. The controls can include a pause or proceed control 422 for stopping or resuming temperature treatment of the patient by the temperature management system 100. The controls can include a mode control 424 for setting the treatment mode of the temperature management system 100. The controls can include a control 426 for navigating menus (e.g., selecting data, entering data, changing units of the display, etc.) or other information displayed on the screen 401. A mute control 428 can be toggled to silence audio feedback or alerts generated by the temperature management system 100. The controls 420, 422, 424, 426, and 428 can include buttons, dials, switches, softkeys, keypads, and so forth.

The interface 400 includes hardware indicators 430, 432 configured to present data to the user using lights or other hardware indicators. A power indicator 432 indicates an OFF/ON status of the temperature management system 100. An alert indicator 430 visually indicates alerts for the user (e.g., when either of temperature thresholds 434, 436 is exceeded).

Figure 5A:
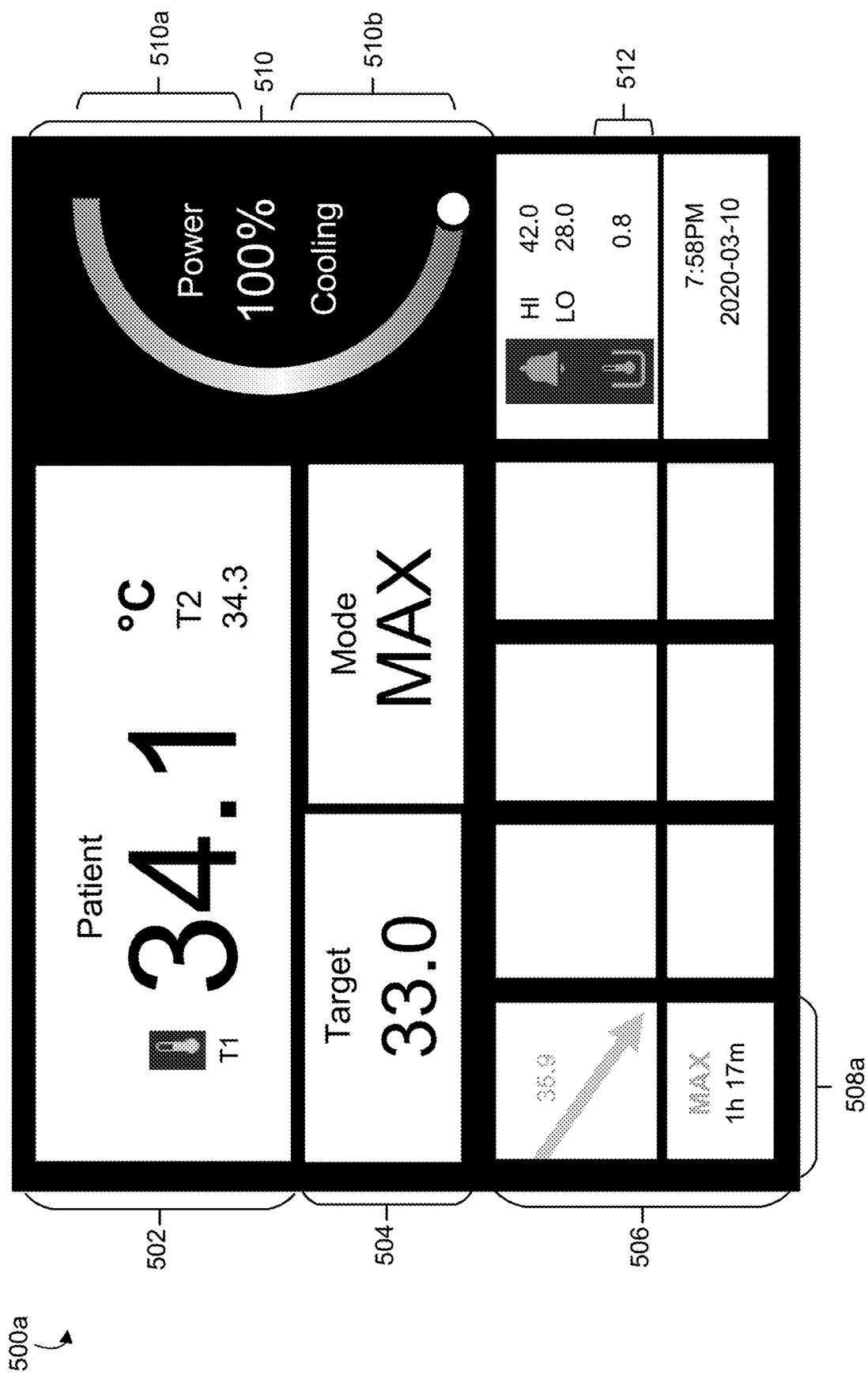
FIG. 5A is an example of a user interface showing data presented during or after operation of a temperature management system such as the systems of FIG. 1, FIG. 2, and FIG. 3.

FIGS. 5A-5D show example screens 500*a*-500*d* of the user interface 400 for different portions of a treatment of the patient. FIG. 5A shows a screen 500*a* that indicates an initial treatment period 508*a* of the treatment. Screen 500*a* shows that a patient temperature 502 is 34.1° C. from a primary temperature reading $T_1$. A secondary temperature reading T2 indicates a temperature of 34.3° C. The target temperature 504 is 33.0° C. The mode is a MAX mode, as previously described. Therefore, the temperature management system 100 is cooling the patient or reducing the patient's temperature as quickly as possible. The symbol in region 506 indicates a downward sloping line to represent that the system is cooling the patient temperature or operating in a manner to lower the patient's temperature over that treatment period. The power meter 510 indicates that the temperature management system 100 is 100% cooling the patient. The bath temperature is set to 0.8° C. These values 502, 504, 506, 5100, and 512 together show how the temperature management system 100 is rapidly cooling the patient. Furthermore, in the region 506, the patient temperature when the treatment period 508*a* was initiated is displayed as 35.9° C., and that the current treatment period (with light text reading MAX) has 1 hour and 17 minutes of elapsed time. This presents a medical service provider with a quick snapshot of how the temperature management system 100 is operating. The user can determine that the temperature management system 100 is cooling the patient or reducing the patient's temperature as rapidly as possible in the initial treatment period of the treatment.

Figure 5B:
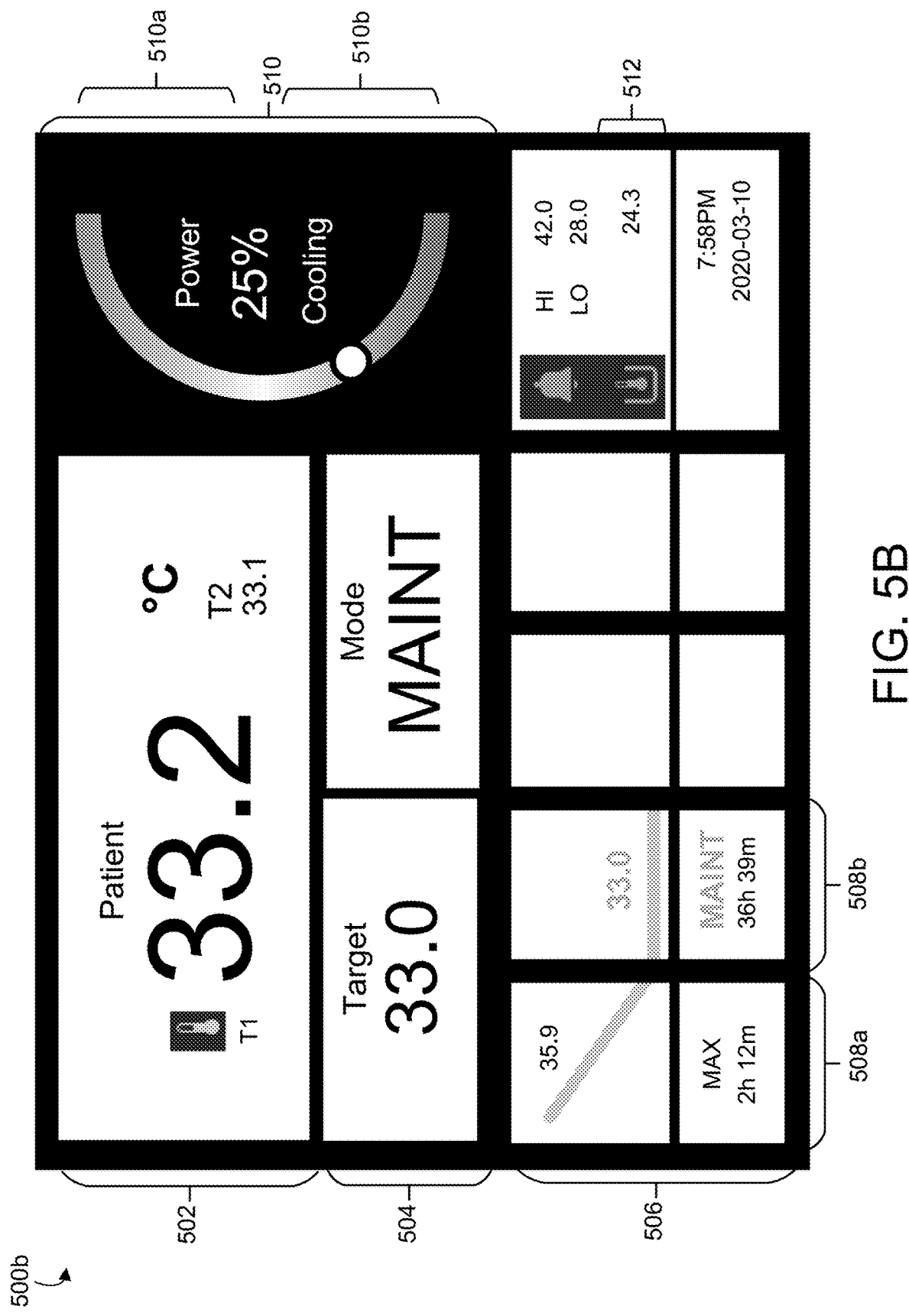
FIG. 5B is an example of a user interface showing data presented during or after operation of a temperature management system such as the systems of FIG. 1, FIG. 2, and FIG. 3.

FIG. 5B shows a screen 500*b* showing a second treatment period 508*b* of a treatment of the patient following the initial treatment period 508*a*. The screen 500*b* shows that the patient temperature is decreased from 35.9° C. to 33.2° C., which is within a threshold tolerance of the target temperature 504 of 33.0° C. The mode is now "MAINT" or maintain temperature. The second symbol of region 506 shows a flat line representing that the system is maintaining the patient temperature or is operating in a manner to maintain the patient's temperature over that treatment period, with the target temperature included. The target temperature is currently being maintained, as indicated by the lighter MAINT text and temperature value 33.0° C. in treatment period 508*b* of region 506. The power meter 510 shows a power reading of 25% cooling. This indicates that the patient is slightly warmer than the target temperature (33.2° C. while the target is 33.0° C.). The bath temperature is higher than it was in the initial treatment period. The bath temperature 512 is now 24.3° C., rather than 0.8° C., and so the power value is decreased from 100% to 25%. The second treatment period 508*b* has been active for 36 hours and 39 minutes.

Figure 5C:
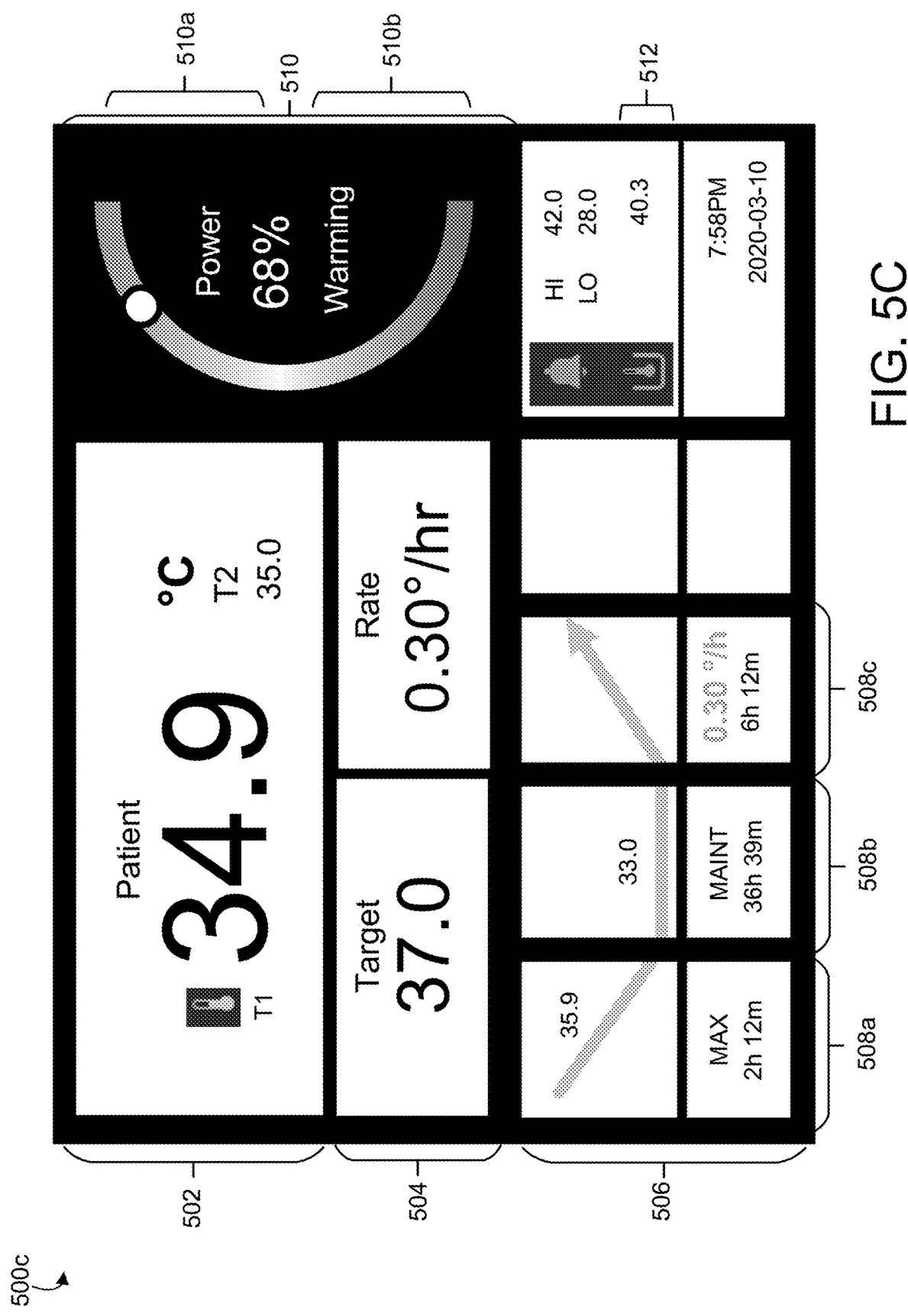
FIG. 5C is an example of a user interface showing data presented during or after operation of a temperature management system such as the systems of FIG. 1, FIG. 2, and FIG. 3.

FIG. 5C shows a screen 500*c* showing a third treatment period of a treatment of the patient following the second treatment period. The mode is a RATE mode, or changing of the temperature of the patient at a specified controlled rate. The screen 500*c* shows that the patient temperature has increased from 33.0° C. to 34.9° C. since the second treatment period. The third symbol of region 506 shows an upward sloping line to represent that the system is warming the patient temperature or that the system is operating in a manner to raise the patient's temperature over that treatment period with the rate of 0.30° C./hour included. The power meter 510 shows a power reading of 68% warming. This indicates that the patient is cooler than the target temperature (34.9° C. while the target is 37.0° C.). The bath temperature is higher than it was in the second treatment period. The bath temperature 512 is now 40.3° C., rather than 24.3° C., and so the power value has increased from 25% cooling to 68% warming. The indicator has moved to the upper half of the arcuate meter. The third treatment period 508*b* has been active for 6 hours and 12 minutes.

Figure 5D:
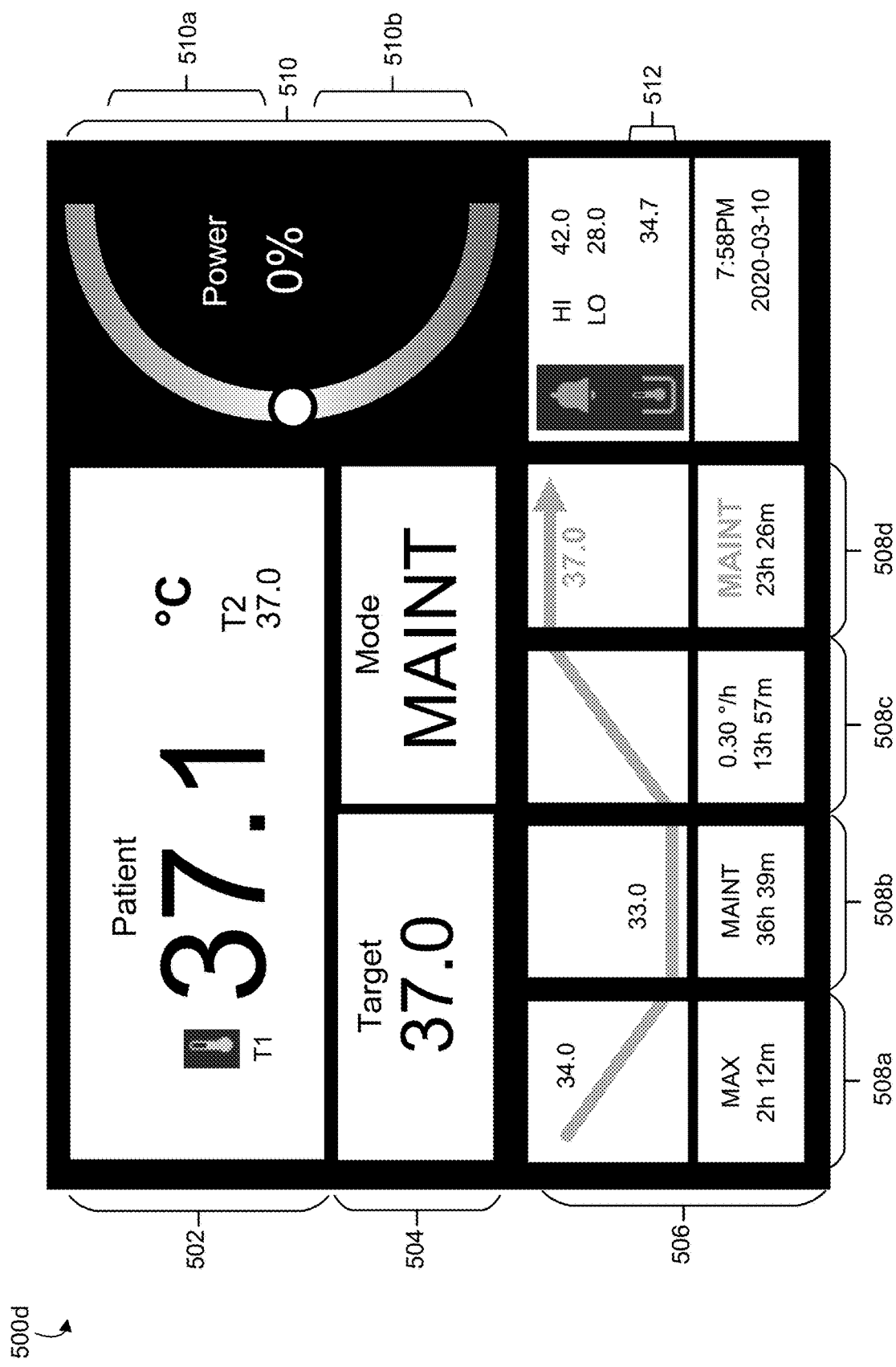
FIG. 5D is an example of a user interface showing data presented during or after operation of a temperature management system such as the systems of FIG. 1, FIG. 2, and FIG. 3.

FIG. 5D shows a screen 500*d* showing a fourth treatment period of a treatment of the patient following the third treatment period. The screen 500*d* shows that the patient temperature is increased from 34.9° C. to 37.1° C., which is within a threshold tolerance of the target temperature 504 of 37.0° C. The mode is now "MAINT" or maintain temperature. The fourth symbol of region 506 shows a flat line representing that the system is maintaining the patient temperature or operating in a manner to maintain the patient's temperature over that treatment period with the target temperature included. The target temperature is currently being maintained, as indicated by the lighter MAINT text and temperature value 37.0° C. in treatment period 508*d* of region 506. The power meter 510 shows a power reading of 0%. This indicates that the patient is no longer being warmed or cooled by the temperature management system 100 (e.g., the pump and other components of the temperature management system are off). The bath temperature is lower than it was in the third treatment period. The bath temperature 512 is now 34.7° C., rather than 40.3° C. However, because the pump of the temperature management system 100 is off, the temperature management system is not heating or cooling the patient, and the power is set to 0%. The fourth treatment period 508*d* has been active for 23 hours and 26 minutes.

In each of FIGS. 5A-5, the meter 510 includes two regions: a warming region 510*a* and a cooling region 510*b*. Warming region 510*a* represents a warming action by the temperature management system. The region begins at approximately a center of the arc of the meter 510. The center of the arc of the meter 510 represents 0% power for the temperature management system in which no cooling or warming may be occurring. The end at the top of the warming region 510*a* represents 100% warming power. The end at the bottom of the cooling region 510*b* represents 100% cooling power. In this way, the warming region 510*a* represents 0-100% warming power for the temperature management system. In this way, the cooling region 510*b* represents 0-100% cooling power for the temperature management system. Each region may be represented by a color gradient. For example, the warming region 510*a* may be white near the center of the arc and orange/red near an end of the arc representing 100% warming power. For example, the cooling region may be white near the center of the arc representing 0% cooling power and blue near an end of the arc representing 100% cooling power.

Figure 6:
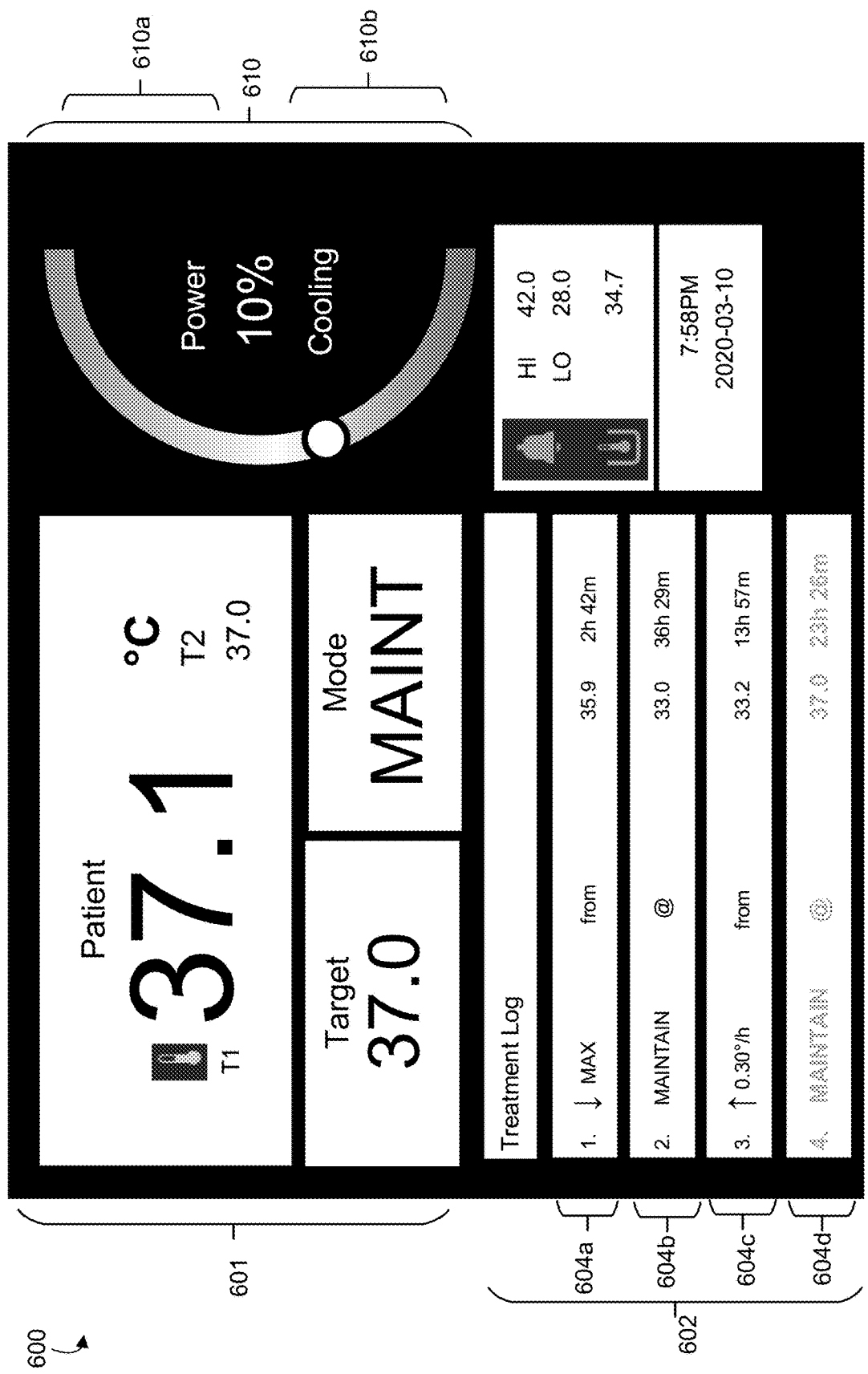
FIG. 6 is an example of a user interface showing data presented during or after operation of a temperature management system such as the systems of FIG. 1, FIG. 2, and FIG. 3.

FIG. 6 shows another example screen 600 of the user interface 400. The screen 600 is an alternative to the screens previously described. Region 602 includes the treatment log of the treatment of the patient as a series of entries rather than as a sequence of symbols as previously described. In region 602, a first treatment period 604*a* is represented by a numerical value of "1" and the mode is MAX. A downward arrow represents that the system is cooling the patient temperature or operating in a manner to lower the patient's temperature over that treatment period. The initial patient temperature is shown as "from 35.9° C.). The time period is 2 hours and 42 m. The data of entry 604*a* can be stored as one or more log messages in the treatment log associated with the patient. In region 602, a second treatment period 604*b* is represented by a numerical value of "2" and the mode is MAINTAIN. A lack of any arrow represents that the system is maintaining the patient temperature or operating in a manner to maintain the patient's temperature over that treatment period. The target temperature is shown as "@ 33.0° C., showing that the system was maintaining the patient temperature or operating to maintain the patient temperature at 33.0° C. The time period is 36 hours and 39 minutes. The data of entry 604*b* can be stored as one or more log messages in the treatment log associated with the patient. In region 602, a third treatment period 604*c* is represented by a numerical value of "3" and the indicator 0.3°/h, indicating a RATE mode. An upward arrow represents that the system is warming the patient temperature or operating in a manner to raise the patient's temperature over that treatment period. The initial patient temperature for the mode is shown as "from 33.2 C). The time period is 13 hours and 57 minutes. The data of entry 604*c* can be stored as one or more log messages in the treatment log associated with the patient. In region 602, a fourth treatment period 604*d* is represented by a numerical value of "4" and the mode is MAINTIAIN. A lack of an arrow represents that the system is maintaining the patient temperature or operating in a manner to maintain the patient's temperature over that treatment period. The target temperature is shown as "@ 37.0° C., showing that the system was operating to maintain the patient temperature at 37.0° C. The elapsed time so far is 23 hours and 26 minutes. The data of entry 604*d* can be stored as one or more log messages in the treatment log associated with the patient. The treatment period 604*d* is shown as active, as the text color is different from other treatment periods 604*a-c*, and also matches the current data of region 601. The power meter 610 is associated with the current, fourth treatment period 604*d* and shows that the temperature management system 100 is cooling the patient at 10% cooling power.

In FIG. 6, the meter 610 includes two regions: a warming region 610*a* and a cooling region 610*b*. Warming region 610*a* represents a warming action by the temperature management system. The region begins at approximately a center of the arc of the meter 610. The center of the arc of the meter 610 represents 0% power for the temperature management system in which no cooling or warming may be occurring. The end at the top of the warming region 610*a* represents 100% warming power. The end at the bottom of the cooling region 610*b* represents 100% cooling. In this way, the warming region 610*a* represents 0-100% warming power for the temperature management system. In this way, the cooling region 610*b* represents 0-100% cooling power for the temperature management system. Each region may be represented by a color gradient. For example, the warming region 610a may be white near the center of the arc and orange/red near an end of the arc representing 100% warming power. For example, the cooling region 610b may be white near the center of the arc representing 0% cooling power and blue near an end of the arc representing 100% cooling power.

Figure 7A:
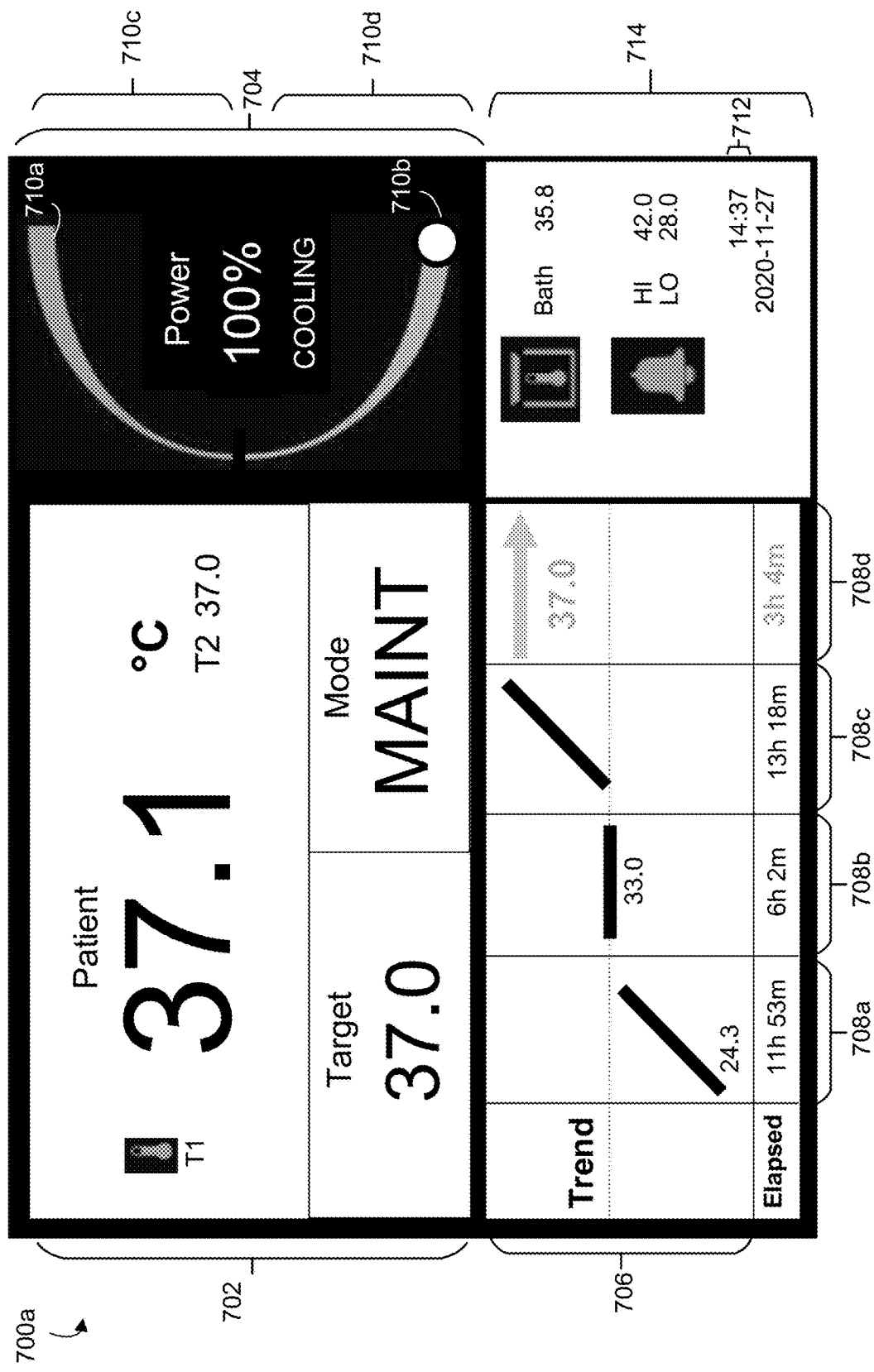
FIG. 7A is an example of a user interface showing data presented during or after operation of a temperature management system such as the systems of FIG. 1, FIG. 2, and FIG. 3.

FIG. 7A show another example screen 700a of the user interface 106, 400. The screen 700a is an alternative to screen 401. The region 702 shows the current treatment data in bright text. The region 706 includes symbols representing operation of the system in a manner to either lower, raise or maintain a patient's temperature over different treatment periods 708a-d. The treatment periods 708a-d are simplified and marked with a "trend" label. The symbols represent similar information as discussed above with respect to the symbols in treatment periods 418a-d of FIG. 4A. In this example, the system was raising the patient temperature or operating in a manner to raise the patient's temperature in treatment period 708a, the system was maintaining the patient temperature or operating in a manner to maintain the patient's temperature at 33.0° C. in treatment period 708b, the system was raising the patient temperature or operating in a manner to raise the patient's temperature in treatment period 708c, and the system was maintaining the patient temperature or operating in a manner to maintain the patient's temperature in treatment period 708d at 37.0° C. The power meter 704 includes flanges at ends 710a and 710b to emphasize the heating and cooling scale.

In any of the example user interfaces 106, 400 (or screens 500a-d, 600, or 700a) described in relation to FIGS. 4-7A, one or more of the following features can be included, either individually or in any combination with the features previously described. The treatment log 407, also represented in regions 506 and 706, shows a non-graphical sequence or series of symbols representing the manner in which the system is operating, e.g., lowering, raising or maintaining the patient's temperature, or the intended direction or direction of the patient's temperature, during a particular treatment period as previously described. Each entry in the log (e.g., entries 418a-d, 508a-d or 708a-d, etc.) can show a symbol including a line or line segment that is sloping, angled or flat, depending on the manner in which the system is operating, e.g., to lower, raise or maintain the patient's temperature, as previously described. Generally, each line segment of the entries 418a-d, 508a-d or 708a-d is distinguishable from the other line segments of the other entries of the treatment log being displayed. In some implementations, the line segments of entries 418a-d, 508a-d or 708a-d are continuous with one another to form a single line, but each entry is distinguished by being a different color than at least one other line segment. In some implementations, the line segments are distinguishable from one another by being spaced apart using a gap, a dot, a vertical line, color change, or other means to separate the line segments from one another. In some implementations, the line segments may have different textures or representations to distinguish each line segment from the other line segments. For example, each line can be solid, dotted, filled with a texture, hollow, and so forth to distinguish the line segment from one or more other line segments of entries 418a-d, 508a-d or 708a-d. In some implementations, the line segments are a solid color, e.g., gray and spaced apart (as shown in entries 708a-d of FIG. 7A). In some implementations, the line segments are only narrowly spaced and are instead framed by narrow borders, as shown for entries 418a-d in FIG. 4A. In some implementations, the line segments are spaced by gaps, as shown for entries 508a-d of FIGS. 5A-5D. In some implementations, each line segment terminates in an arrowhead. In some implementations, only an entry representing a presently executing treatment period (e.g., entry 418d of FIG. 4A) includes an arrowhead. In some implementations, no line segments include an arrowhead. In some implementations, the currently executing treatment period is highlighted in the user interface, as shown in entry 708d of FIG. 7A.

Generally, the line segments of entries 418a-d, 508a-d or 708a-d of the treatment logs are located in particular positions within the respective regions (e.g., regions 506, 706 of the user interfaces 500a-d and 700). For example, based on a relative temperature for beginning treatment for a given treatment period, the line segment can be placed in a low position, a middle position, or a high position within the entry of the region. For example, as shown in FIG. 7A, entry 708a shows a treatment period in which the initial patient temperature was relatively low. The upward sloping line is placed at a low position in the entry 708a. In comparison, the initial patient temperature or starting temperature for the treatment period in shown in entry 708c was relatively higher than for the treatment period in entry 708a. The upward sloping line for the treatment period shown in 708c is thus positioned higher on the screen than the line for the treatment period entry 708a. This immediately presents to a user what the general trend of treatment is for a patient. Further, as shown in FIG. 7A, initial patient temperature values at the start of a treatment period or target temperature values can be included in the entries 708a-d. In certain implementations, patient temperature values during or at the end of a treatment period may be shown in the entries or an average patient temperature during the treatment period may be shown. A horizontal line segment representing maintaining of the patient temperature or the system operating in a manner to maintain the patient's temperature can be shown at low, middle, or high positions in a treatment period section in a visual representation of a treatment log. In certain implementations, there may be two or more, e.g., three, different Y axis positions at which a horizontal line segment can appear in a treatment period section. In certain implementations, the position of the horizontal line segment in a treatment period section may depend on a relative patient temperature or target patient temperature for those respective treatment periods. In FIG. 7A, a middle position is shown for entry 708b and a high position is shown for entry 708d. As shown in FIG. 7A, the target temperature for entry 708b (33.0° C.) is lower than the target temperature for entry 708d (e.g., 37.0° C.). In certain implementations, the positioning of a sloped or horizontal line segment may be determined by one or more rules. For example, if the system is operating to raise a patient's temperature, the sloped line segment starts in the bottom left corner of a treatment period section or tile; if the system is operating to lower a patient's temperature, the sloped line segment starts in the upper left corner of a treatment period section or tile; if the system is operating to maintain a patient's temperature, the horizontal line segment starts in the middle left of a treatment period section or tile. In certain implementations, consecutive line segments appearing in adjacent treatment period sections or tiles follow a rule of continuity, i.e., a new line must start where the previous line ended. In other words, while each line may still be distinguished or separated from an adjacent line, e.g., with a gap or space, each subsequent line must start where the previous line ended in the Y axis or vertical direction in a treatment period section or window (e.g., as shown in the treatment log 706).

The treatment logs 407, 506, 606, and 706 can each have a specific layout or aspect ratio for display on the respective screens or user interfaces 400, 500*a-d*, 600, and 700 of FIGS. 4-7A. For example, each treatment log can be a minimum of four entries or treatment period sections wide. Generally, four entries are shown because, to treat certain conditions, e.g., cardiac arrest, there are four treatment periods for treating a patient suffering from cardiac arrest. For example, these treatment periods can include a period of cooling or lowering of the patient's temperature (e.g., at 33° C.), a period of maintaining the patient's temperature (e.g., at 33° C.), a period of warming or raising of the patient's temperature (e.g., to 36° C.), and another period of maintaining the patient's temperature (e.g., at 36° C.). In an example, a user can see that the patient with cardiac arrest has gone through all 4 treatment periods or see how far along in the treatment the patient is, without having to manipulate the display. In another example, four treatment periods are shown for treating accidental hypothermia. These include a period of warming or raising of the patient's temperature (e.g., at 33° C.), a period of maintaining the patient's temperature (e.g., at 33° C.), another period of warming or raising of the patient's temperature (e.g., to 37° C.), and another period of maintaining the patient's temperature (e.g., at 37° C.). In certain implementations, the aspect ratio for the visual representation or display of the treatment log can be three units or positions tall (Y axis) for each treatment period section and four treatment period sections wide. This ratio was optimized to provide customers with enough information regarding the patient's past and current temperature management treatment, but not too much information. In certain implementations, the aspect ratio for the visual representation or display of the treatment log can be represented as n X (n−1) i.e., the number of Y axis positions for horizontal or sloped line segments is one less than the number of treatment period sections visible on a single visual representation or display screen. For example, a display having such an aspect ratio for it visual representation of the treatment log (e.g., showing at most four treatment periods and having at least three Y axis positions for horizontal or angled line segments) may allow for a visual display of a stairstep treatment (e.g., alternating between lowering a patient's temperature and maintaining a patient's temperature).

The non-graphical configuration of showing symbols representing each treatment period of a treatment log on the screen at the same time and also showing relative positions of line segments representing the manner in which the system was or is operating, e.g., lowering, raising or maintaining the patient's temperature during various treatment periods, allows a user to determine how a patient has been treated and where the patient is in the treatment. The treatment log can thus display a representation of any combination of treatment periods. The representation is advantageous because it enables a user to instantly recognize how treatment is progressing. For example, after a shift change, a new caregiver can arrive in the hospital room, and quickly come see the patient's temperature management treatment history on the display screen. Additionally, the treatment log can be represented symbolically as described herein, such that it is clear to the user that the treatment log is not a graph, but rather a series of distinct or segmented icons or symbols representing the manner in which the system has been or is operating, e.g., lowering, raising or maintaining the patient's temperature, over a series of treatment periods, e.g., the four most recent treatment periods in time. This format provides a significant advantage over a graphical representation in that it is simpler and quicker to interpret than a graph. This is important for clinicians who are busy or otherwise experiencing "information overload". It provides an "at a glance" visual which does not include visual distractions present on a graph, e.g. temperature probe shifts due to patient movement. The entries of the treatment log may also be represented using less processing power than that required for rendering a graph.

In some implementations, at a glance, the sections of the treatment log region show (up to) the four most recent treatment periods. The elapsed time can be shown below each treatment period. In this example, a horizontal line shows a target temperature for the treatment period. The first angled line shows a patient temperature at the start of the treatment period. Each angled line direction represents a direction or intended direction of the patient's temperature (e.g., warming or cooling) of intended treatment for that treatment period. In some implementations, a prescribed trend can be shown, or a prescription for treatment can be shown.

As described above in relation to user interface 400 and screens 500*a-d*, 600, and 700*a*, the user interface or screen can be represented in four windows that are positioned relative to one another on a single display screen. The positioning of the windows facilitates understanding of the treatment process by a user because it provides an amount of information that is neither too simplistic nor overly complex. For example, as seen in FIG. 7A, the current treatment data region 702 is a first window, the power meter 704 region is a second window, the treatment log region 706 is a third window, and an operational parameter region 714 is a fourth window. The region 714 can show a total elapsed treatment time at location 712, rather than a current date and time. This arrangement shows important and critical information regarding temperature management treatment such as patient temperature, target temperature and/or mode, a treatment log showing past and present treatment periods, bath temperatures, and power percentage all on a single screen. This allows the caregiver to see the most important and critical information in simple easy to read format on a single screen, without manipulating or navigating through menus or different screens, thus allowing the caregiver to keep their hands free to care for the patient.

In FIG. 7A, the meter 704 includes two regions: a warming region 710*c* and a cooling region 710*d*. Warming region 710*c* represents a warming action by the temperature management system. The region begins at approximately a center of the arc of the meter 704. The center of the arc of the meter 704 represents 0% power for the temperature management system in which no cooling or warming may be occurring. The end 710*a* at the top of the warming region 710*c* represents 100% warming power. The end 710*b* at the bottom of the cooling region 710*d* represents 100% cooling. In this way, the warming region 710*c* represents 0-100% warming power for the temperature management system. In this way, the cooling region 710*d* represents 0-100% cooling power for the temperature management system. Each region is represented by a color. For example, the warming region 710*c* may be orange/red. For example, the cooling region 710*d* may be blue. The two regions 710*c*, 710*d* can be separated by a gap.

Figure 7B:
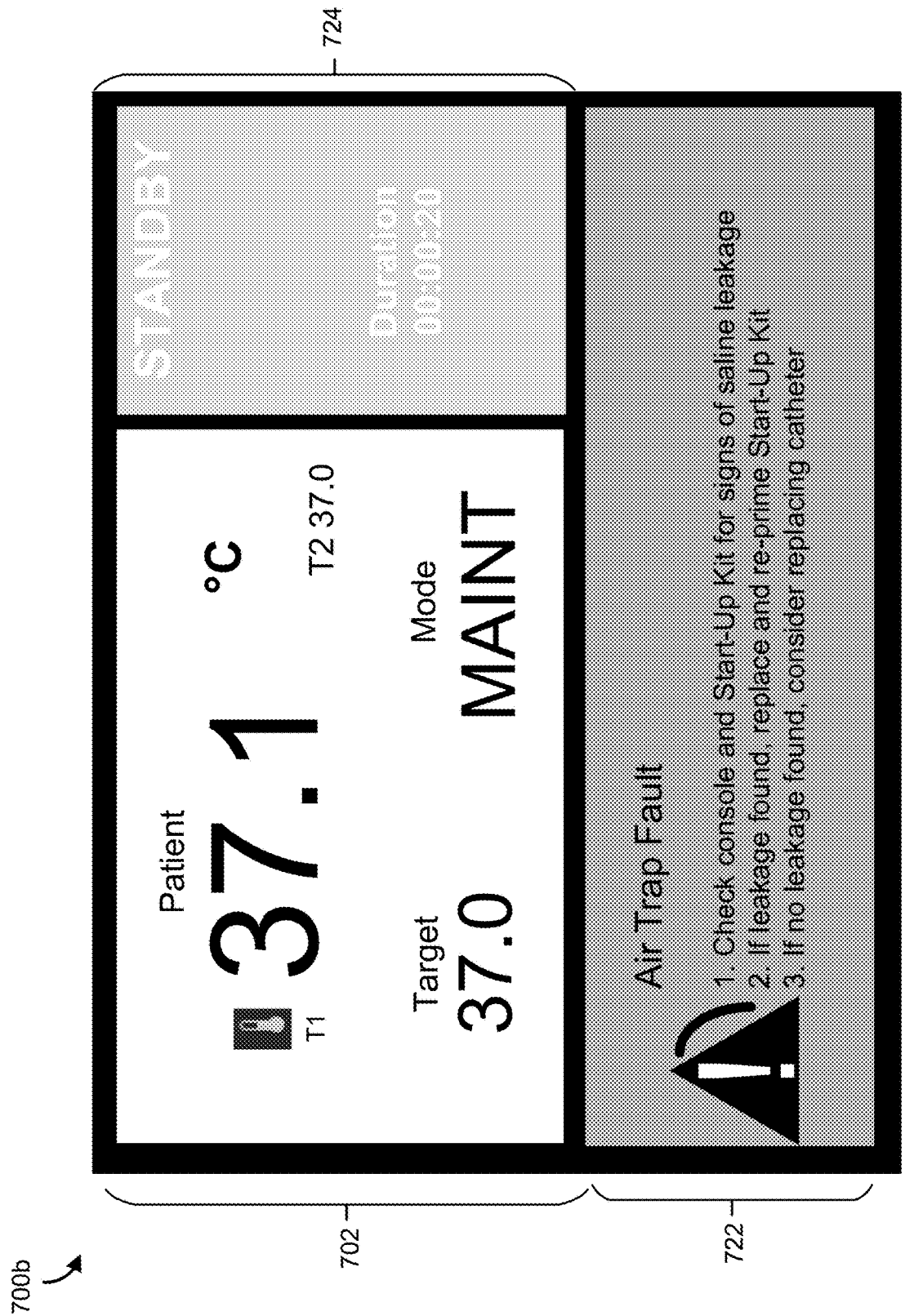
FIG. 7B is an example of a user interface showing data presented during or after operation of a temperature management system such as the systems of FIG. 1, FIG. 2, and FIG. 3.

FIG. 7B shows a screen 700*b* for the user interface 106, 400 of the temperature management system 100. The screen 700*b* includes a fault report 722 near the current treatment data region 702. The fault report 722 reports alerts or errors in the temperature management set up or treatment of the patient. Faults can be caused by any on the components of the temperature management system 100 and reported in the user interface. The fault report 722 in this example shows is an air trap fault. The fault report 722 shows instructions for resolving the fault, such as checking for leakage in the console, replacement of the tubing of the fluid loop and/or air trap, and replacement of the heat exchange device (e.g., a catheter). A region 724 shows a standby time elapsed while treatment has been paused. Here, the time is 20 seconds. Because temperature management treatment is time sensitive, the fault resolution is also time sensitive. The fault screen 700b assists a user in resolving the fault as quickly as possible so that treatment can be resumed. As previously described, an alert can be generated or an alarm can be sounded to encourage resolution of the fault. The alert can be transmitted to a remote computing device or system.

Figure 7C:
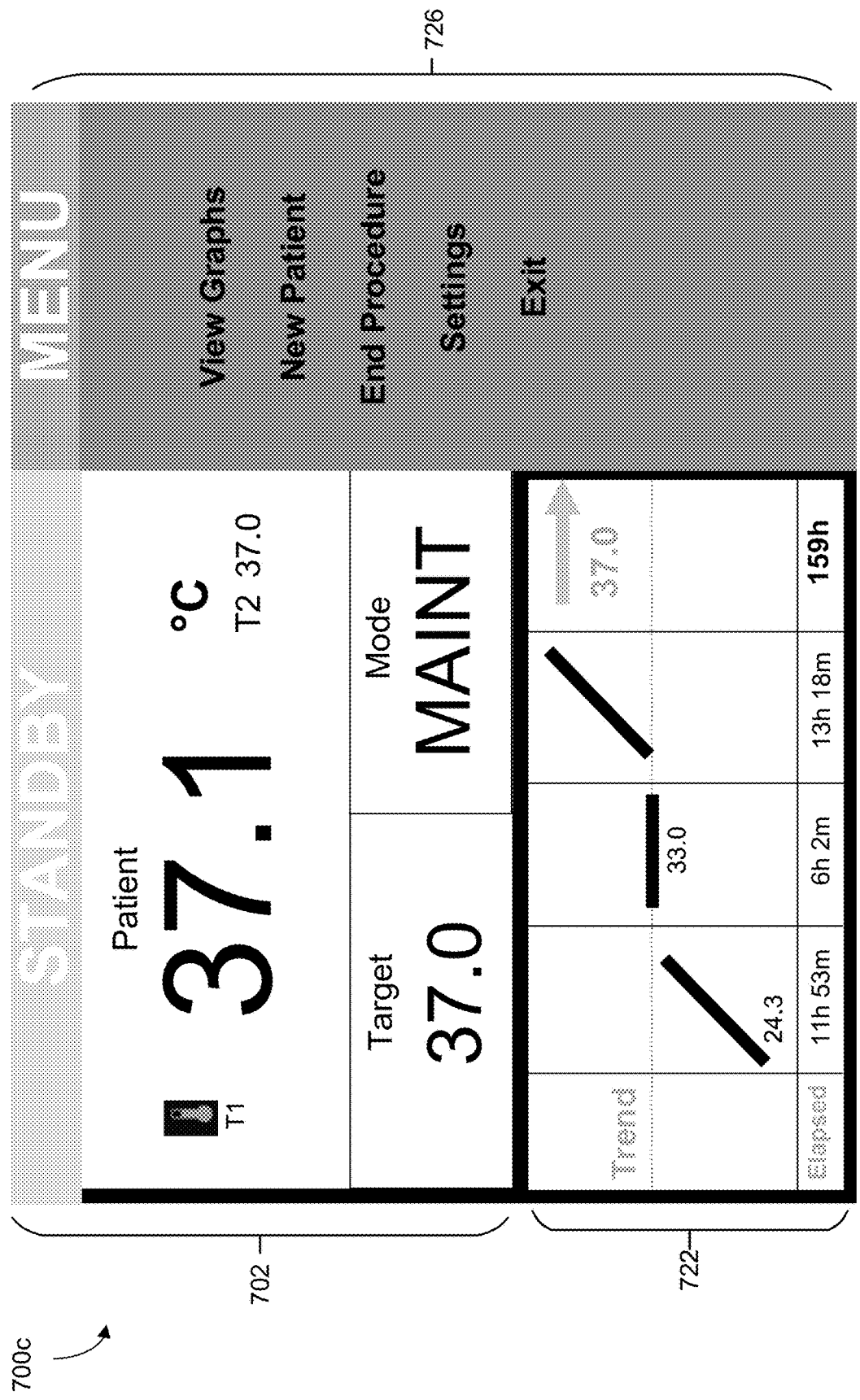
FIG. 7C is an example of a user interface showing data presented during or after operation of a temperature management system such as the systems of FIG. 1, FIG. 2, and FIG. 3.

FIG. 7C shows a screen 700c for the user interface 106, 400 of the temperature management system 100. The screen 700c includes a menu region 726. The treatment log 722 shows at least four sections. The current patient data region 702 is shown.

Figure 7D:
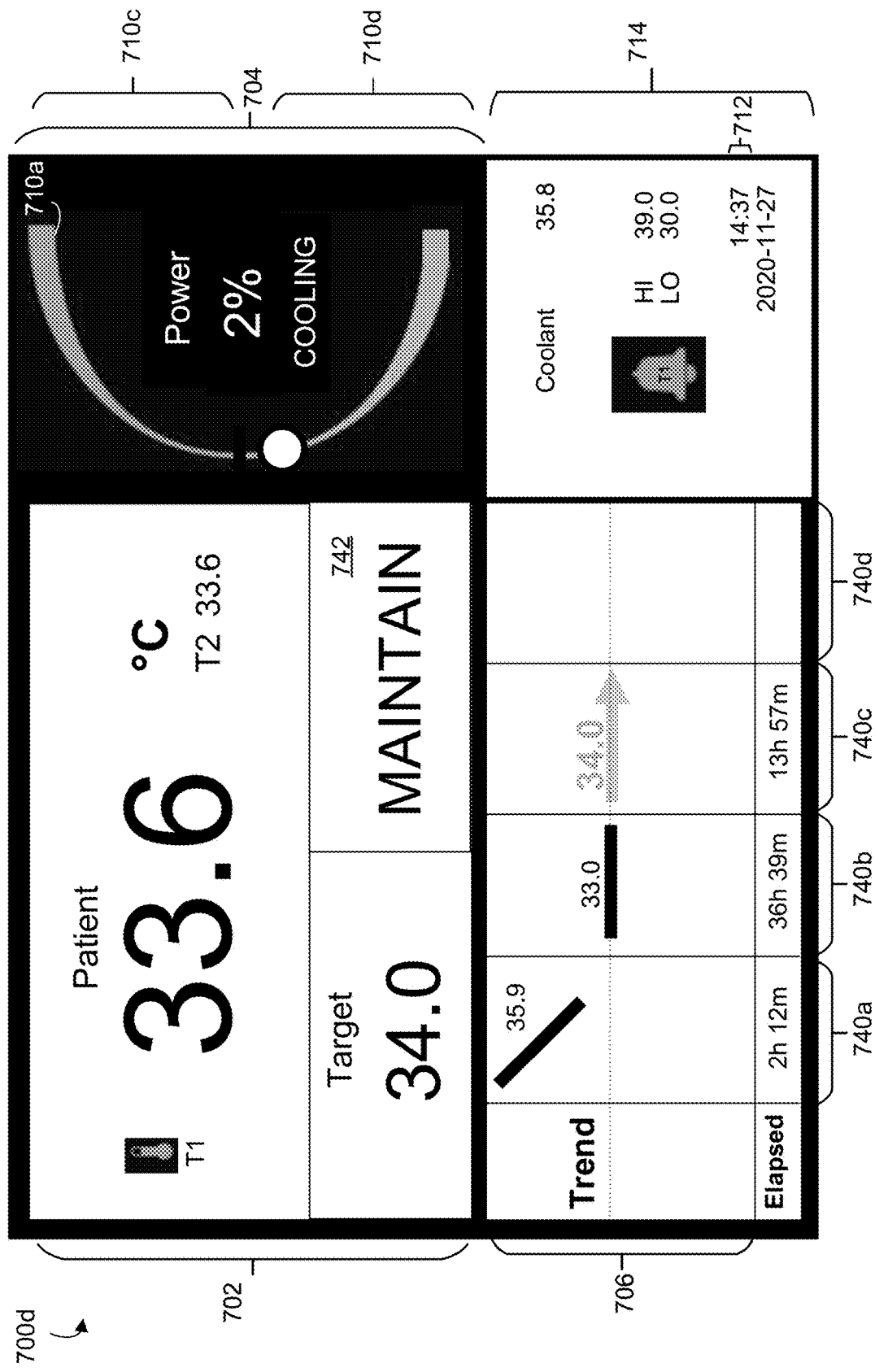
FIG. 7D is an example of a user interface showing data presented during or after operation of a temperature management system such as the systems of FIG. 1, FIG. 2, and FIG. 3.

FIG. 7D shows an example screen 700d for the user interface 106, 400 of the temperature management system 100. The screen 700d includes entries for the treatment log each represented in sections or tiles 740a, 740b, 740c, and 740d for temperature management of a patient. Similar to previously described screens (e.g., 708a-d), the sections or tiles 740a-d include symbols representing operation of the system in a manner to lower, raise or maintain a patient's temperature (cooling, warming or maintaining states) over different treatment periods represented in tiles 740a-d. A downward sloping line segment in tile 740a indicates that the temperature management system 100 is operating in a manner to lower the patient's temperature for the elapsed time of the treatment period 740a. The temperature of 35.9° C. shown near the downward slopping line segment indicates the patient's temperature when the treatment period was initiated. Once the patient reaches the target temperature during the treatment period 740a, the system switches to a maintaining state or is operated in a manner to maintain the patient's temperature at the target temperature of 33.0° C. for treatment period 740b. If the system is operating in a MAINTAIN mode, and the target temperature is adjusted (e.g. to 34 C), and the patient temperature (e.g. 33.6 C) is within the threshold of the maintaining state range (e.g. 0.5 C) of the new target temperature, the system will operate to maintain the patient's temperature at that new target temperature of 34° C., and generate and display a new section or tile as shown in tile 740c. However, because the system remains in a MAINTAIN mode (without an intervening change to a MAX, RATE or FEVER mode), the subsequent tile 740c includes a horizontal line symbol representing that the temperature management system is continuing to operate to maintain the patient's temperature, albeit at the new target temperate which is also shown in tile 740c. Although the horizontal line symbols of tiles 740b-c are co-linear, they do not correspond to the same y axis, because the tiles do not represent a graph. The side-by-side colinear depiction of the two horizontal line symbols indicates that the target temperature was changed, but that the system remained in the MAINTAIN mode. The different target temperatures are also shown in text in each tile.

In the mode/rate region 742, a label representing the mode of the temperature management system 100 is shown, or a heating or cooling rate may be shown. In some implementations, the maintain label is shown in accordance with the following rules. If the active tile (e.g., tile 740c) includes a symbol representing operation of the system in a manner to maintain a patient's temperature or a maintaining state, then the Mode/Rate field on the main screen will read MAINTAIN with the following exceptions. When the target temperature is changed, the mode/rate region 742 updates to indicate the last mode/rate setting selected by the user until the temperature management system 100 establishes whether the system is still in the maintaining state. The resulting system state is determined only after resuming treatment. If the system state is a maintaining state, then the mode/rate region 742 displays MAINTAIN again. Otherwise, the region 742 continues to display the last mode/rate setting selected by the user. In certain implementations, if the system requires pausing to change system parameters, e.g., target temperature, the resulting system state may be determined only after resuming treatment. Determining a system state only after resuming treatment acts as a filter to minimize excess tile generation in the event that a user changes the treatment parameters repeatedly.

When a mode/rate is changed, MAINTAIN is no longer displayed in region 742. The mode/rate region 742 displays the entered mode/rate setting until the temperature management system 100 determines whether it is still in the maintaining state. If the system state is a maintaining state, then the mode/rate region 742 displays MAINTAIN again. Otherwise, region 742 displays the entered mode/rate setting. When the temperature management system 100 is in a FEVER mode, MAINTAIN is never displayed. The mode/rate region 742 may display FEVER CONTROL. In certain implementations, if the system requires pausing to change system parameters, e.g., mode/rate, the resulting system state may be determined only after resuming treatment. Determining a system state only after resuming treatment acts as a filter to minimize excess tile generation in the event that a user changes the treatment parameters repeatedly.

The temperature management system 100 uses a sampling algorithm over a fixed period of time, called a debounce time, to determine whether the system changes to a new system state, and thus whether a new treatment period or tile should be generated and displayed. The treatment log entry drawing rules (e.g., for tiles 508a-d, 708a-d, 740a-d, etc.) and mode/rate display rules (e.g., for region 410, 742) may use a debounce time to ensure that a sufficient sampling of stable data exists to make a determination about a change to system.

Additionally, the temperature management system 100 can uses a state machine to transition between initial or power on, warming states, cooling states, maintaining states, etc. Table 1 shows an example of a state machine for the temperature management system 100.

TABLE 1

Example State Machine for Temperature Management System

| | Start State | Patient/Target Temperature Condition | Duration | Next State |
| --- | --- | --- | --- | --- |
| 1 | Initial (Power On) | PT − TT >= 0.5 C. | Debounce Time | Cooling |
| 2 | Initial (Power On) | PT − TT <= 0.5 C. | Debounce Time | Warming |
| 3 | Initial (Power On) | \|PT − TT\| < 0.5 C. | Debounce Time | Maintaining |
| 4 | Cooling | PT − TT <= −0.5 C. | Debounce Time | Warming |
| 5 | Cooling | \|PT − TT\| < 0.5 C. | Debounce Time | Maintaining |
| 6 | Warming | PT − TT >= 0.5 C. | Debounce Time | Cooling |
| 7 | Warming | \|PT − TT\| < 0.5 C. | Debounce Time | Maintaining |
| 8 | Maintaining | PT changed/ TT unchanged | Debounce Time | No Change |
| 9 | Maintaining | TT changed/ PT − TT >= 0.5 C. | Debounce Time | Cooling |

TABLE 1-continued

Example State Machine for Temperature Management System

| | Start State | Patient/Target Temperature Condition | Duration | Next State |
|---|---|---|---|---|
| 10 | Maintaining | TT changed/ PT − TT <= −0.5 C. | Debounce Time | Warming |
| 11 | Maintaining | TT changed/ |PT − TT| < 0.5 C. | Debounce Time | Maintaining |

The above table includes example rules for transitioning between system states as well as an example rule in row 8 for when the system state may remain unchanged. For example, if the system is operating in a maintaining state and the target temperature is unchanged, but the patient temperature drifts outside the threshold of the maintaining state range, the system will remain in the maintaining state and no new tile is generated or displayed. In this example, once the system achieves the maintaining state, only a change of target temperature can result in an exit from that maintaining state. This example is one illustration of how the data represented in the sections or tiles is different from a graph. The patient could deviate significantly from the target, e.g. by 3 C, and then be brought back to target, but the tile would only show a single horizontal line representing the maintaining state.

If the patient (PT)/target temperature (TT) condition indicated in the table is not maintained for the specified duration then the system remains in the start state or existing state.

The following rules can indicate how the temperature management system 100 displays data on the user interface. Specifically, the sections or tiles 508*a-d*, 708*a-d*, 740*a-d*, etc. are drawn on the user interface as described below. Here, tiles 508*a*, 708*a*, 740*a*, etc. are described as position A, 508*b*, 708*b*, 740*b*, etc. are described as position B, 508*c*, 708*c*, 740*c*, etc. are described as position C, and 508*d*, 708*d*, 740*d*, etc. are described as position D. In some implementations, the treatment log tiles are populated with line segments starting at the left of the screen (e.g., 508*a*, 708*a*, 740*a*, etc.). New tiles are first added to the right of position A, then at position B, then at position C, then at position D. After 4 tiles are drawn and visible, tile contents are shifted left and new tile content is drawn at position D. Next, the current treatment tile is the active tile. In some implementations, the active tile is the rightmost visible tile. In some implementations, there is only one active tile. In some implementations, the tile contents of the active tile are rendered with a white treatment segment. In some implementations, inactive visible tiles correspond to previous treatment settings. In some implementations, the contents of inactive visible tiles are rendered in grey.

Examples of the treatment log entry tile content are now described. In some implementations, a temperature raising or warming state treatment log tile is rendered with an upward diagonal line segment. In some implementations, a tile representing a temperature lowering or cooling treatment state is rendered with a downward diagonal line segment. In some implementations, a tile representing a temperature raising or warming state or a tile representing a temperature lowering or cooling state does not have any temperature information rendered in it with the following exception: a tile representing temperature raising/warming or temperature lowering/cooling is rendered as the very first tile displays the presenting patient temperature at the beginning of the represented temperature raising/warming or temperature lowering/cooling state.

In some implementations, a tile representing a maintaining treatment state is rendered with a horizontal line. In some implementations, a tile representing a maintaining treatment state always displays the target temperature associated with that maintaining state. In some implementations, all tiles include a duration filled in at the tile bottom indicating the hours and minutes the system was in the state indicated by the tile. Inactive tiles include a total duration for that treatment in hours and minutes. The active tile includes ongoing duration information for the active treatment state. In some implementations, an active tile duration is updated once per minute.

Examples of treatment log tile drawing rules are now described. In some implementations, a temperature lowering/cooling tile is drawn when the patient temperature exceeds the target temperature by 0.5° C. or more at the time of treatment setting. This tile remains in place while that condition remains true. In some implementations, a tile representing temperature raising/warming treatment is drawn when the patient temperature is less than the target temperature by 0.5° C. or more at the time of treatment setting. This tile remains in place while that condition remains true. In some implementations, a tile representing a maintaining treatment state is drawn when the patient temperature crosses to within 0.5° C. of the target temperature during a treatment. In some implementations, once a tile representing a maintaining treatment state is drawn, no new tile representing a maintaining treatment state is normally drawn. Specific exceptions apply to this requirement based on user interaction with the system: In some implementations, if the target temperature is changed but the patient temperature is within 0.5° C. of the new target temperature, a new tile representing a maintaining treatment state is drawn with the newly selected target temperature indicated. If the target temperature is changed such that patient temperature exceeds the new target temperature by 0.5° C. or more, then a new tile representing a cooling state is drawn. In some implementations, if the target temperature is changed such that patient temperature is less than the new target temperature by 0.5° C. or more, then a new warming state tile is drawn. In some implementations, two tiles representing a cooling treatment state are not displayed adjacent to one another even if system operating conditions e.g., rate, target temperature or patient temperature, change and the new system treatment state is determined to be cooling. In some implementations, two tiles representing a warming treatment state are not displayed adjacent to one another even if system operating conditions, e.g., rate, target temperature or patient temperature change and the new system treatment state is determined to be warming.

The fever mode behavior of the temperature management system 100 is now described. The fever mode behavior follows the tile drawing rules listed in the previous section with the following exception: The fever mode does not display a warming state tile even if the target temperature exceeds the patient temperature by 0.5° C. or more. If that specific condition occurs, the fever mode displays a maintaining state tile with the target temperature as specified by the end-user.

In an example implementation, when a change is made to a target temperature or a new target temperature is input, a new section or tile of the visual representation of the treatment log is generated and displayed. In another example implementation, during treatment, if the patient's temperature comes to within a preprogramed threshold (e.g., 0.5 degrees) of the target temperature, a new section or tile of the visual representation of the treatment log is generated displaying a symbol that represents operation of the temperature management system to maintain the temperature of the body of the patient (e.g., a maintaining tile is generated that represents a maintaining state).

The stability of the temperature management system is now described. To avoid reporting of transient states owing to user tile errors or sudden transient temperature variation, the state machine has a filtering operation that allows state transition only after the transition conditions are stable for a fixed period (the debounce time, which can be e.g., about 10-40 seconds or 20-30 seconds). This filtering applies to both the target temperature and state transitions. For example, if the target temperature changes from 35.2 C to 35.7 C and back to 35.2 C in 1 second then that transition will not be registered, and the temperature management system 100 operates as if the target temperature never changed from 35.2 C since the target temperature was never stable at 35.7 C having not maintained that value for more than the debounce time. In another example, if the patient temperature were 37.0 C and the target temperature was 36.0 C then the temperature management system 100 is in a temperature lowering or cooling state. If the patient temperature dipped to 33.0 C for 1.5 seconds and then returned to 37.0 C the temperature management system 100 remains in the cooling state since the system 100 did not remain in the temperature raising or warming state for more than the debounce time.

Since the system is testing for stability of two variables (target temperature and state) that have dependencies on each other, the stability requirements are additive. Specifically, in the case when the temperature management system 100 is in a maintain state but the target temperature is changing, the changing target temperature is tested for stability to ensure that end-users are protected from entering a mistaken temperature value and causing the system 100 to enter an incorrect state as well as to ensure that if they remain in the maintaining state, a stable target temperature is indicated.

Figure 7E:
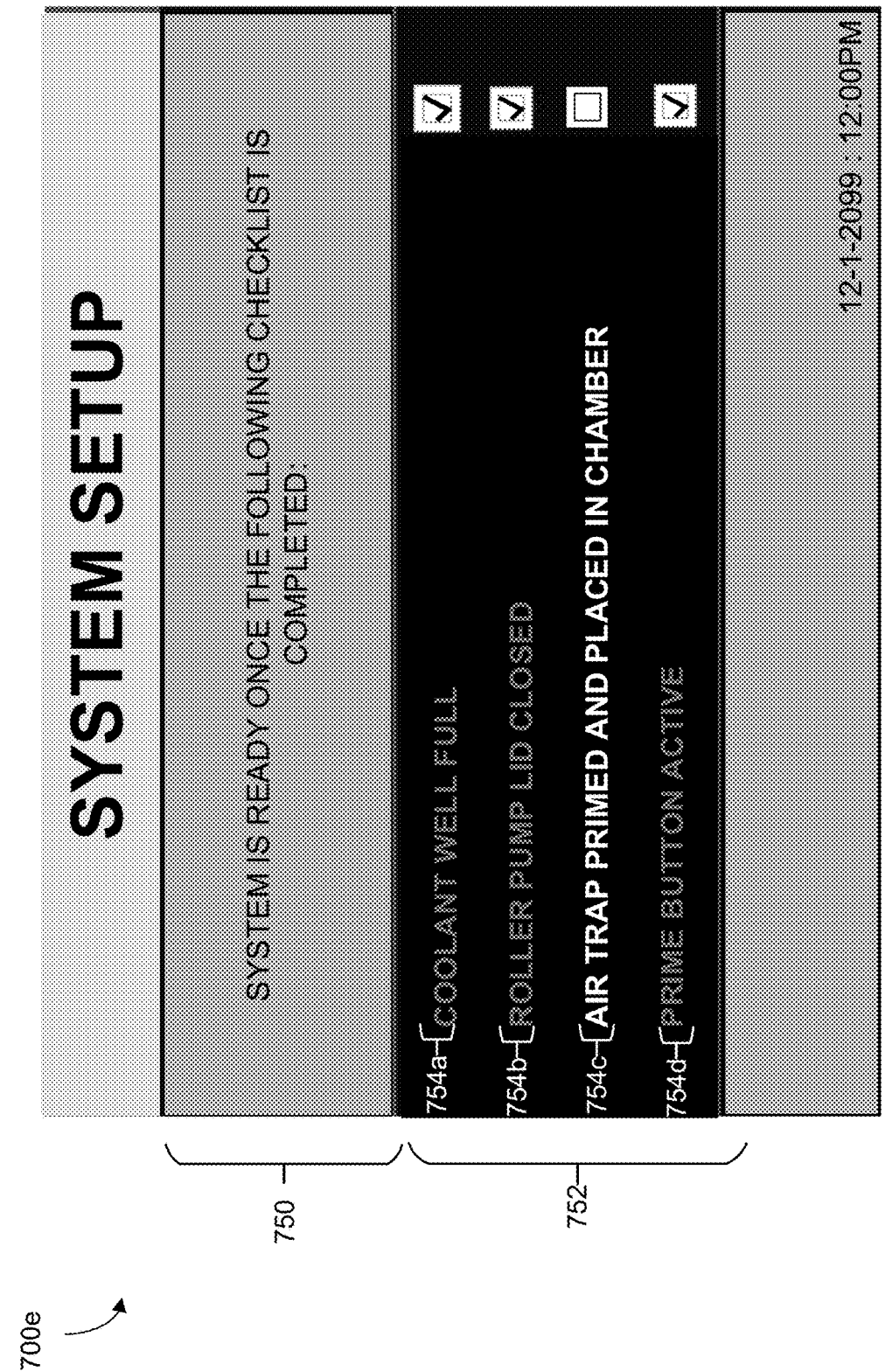
FIG. 7E is an example of a user interface showing a system setup screen of a temperature management system such as the systems of FIG. 1, FIG. 2, and FIG. 3.

FIG. 7E is an example of a user interface 700e showing data presented during system setup. For example, a system setup checklist is displayed in a single column having multiple rows. Section 752 includes instructions stating that the system is ready once the checklist is complete. Section 752 includes a list of items to be checked displayed in multiple roles. After each item is checked, a checkmark symbol is displayed next to the respective item indicating that the item has been checked.

Figure 8:
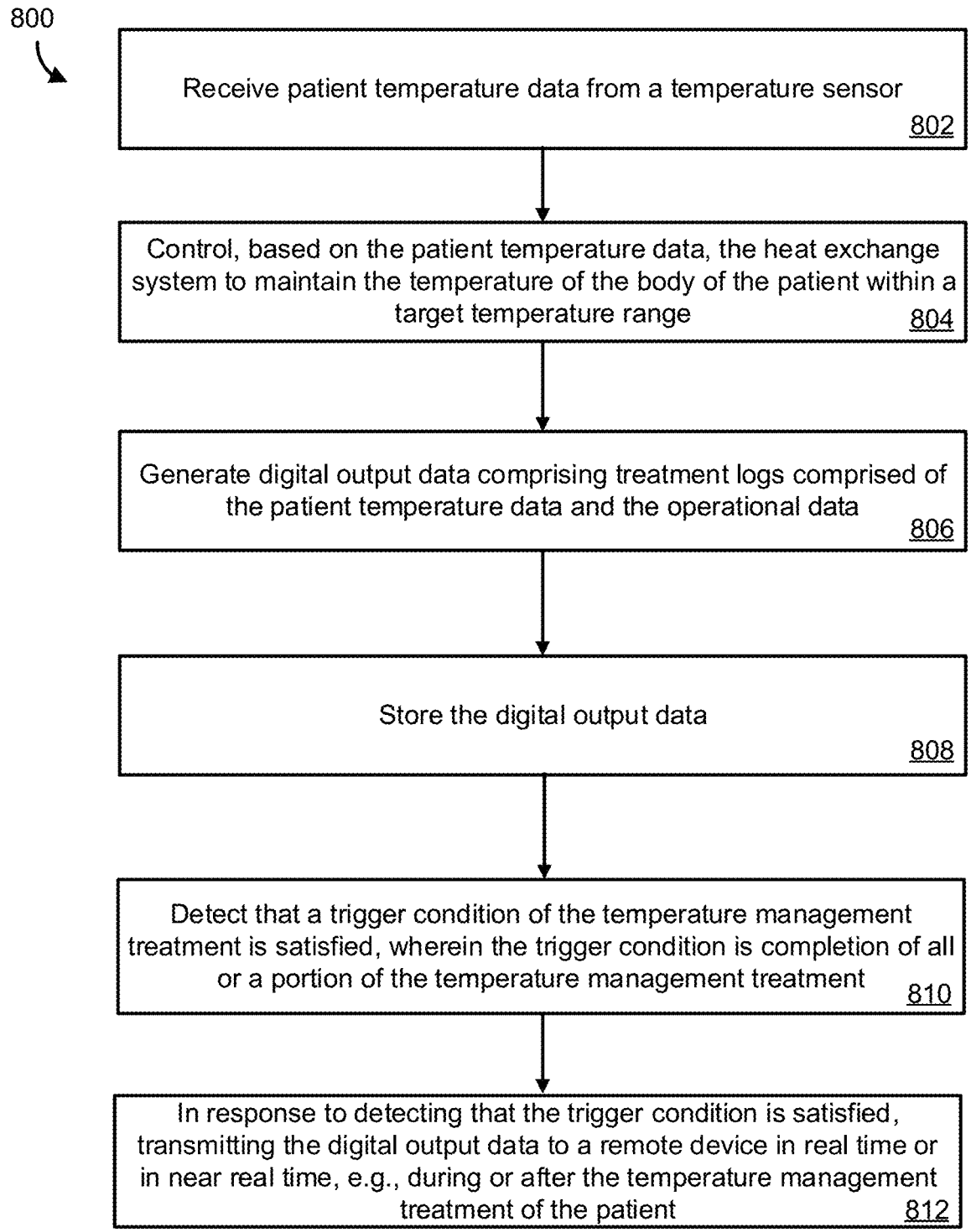
FIG. 8 shows a flow diagram including an example process for performing temperature management treatment for a patient and/or reporting, generating or displaying data from the temperature management treatment using a temperature management system such as the systems of FIG. 1, FIG. 2, and FIG. 3.

FIGS. 8-12 each show a flow diagram of an example process for treatment of a patient by the temperature management system (e.g., temperature management system 100 of FIGS. 1-3). FIG. 8 shows a process 800 for treatment of a patient by a temperature management system. The temperature management system includes a heat exchange device coupled to an extracorporeal control console. The temperature management system is configured to exchange heat with a body of a patient and to obtain operational data representing an operational status of the temperature management system during a temperature management treatment of the patient, as previously described. The temperature management system includes at least one sensor configured to measure patient temperature data indicative of a temperature of the body of the patient. The temperature management system includes a processor, a memory storing instructions, and associated circuitry communicatively coupled to the sensor. The processor executes the process 800. The processor is configured to receive (802) the patient temperature data from the sensor. The processor is configured to control (804), based on the patient temperature data, the temperature management system to maintain the temperature of the body of the patient within a target temperature range. The processor is configured to generate (806) digital output data comprising treatment logs comprised of the patient temperature data and the operational data. The process or is configured to store (808) the digital output data in a data store. The processor is configured to detect (810) that a trigger condition of the temperature management treatment is satisfied, wherein the trigger condition is completion of all or a portion of the temperature management treatment; and (812) in response to detecting that the trigger condition is satisfied, transmitting the digital output data to a remote device in real time or in near real time, e.g., during or after the temperature management treatment of the patient. In some implementations, the digital output data includes a predefined format that enables the digital output data to be streamed to a remote device. The temperature management system can include a transmitter configured to transmit the digital output data to the remote device. In some implementations, the predefined format is configured to enable the remote device to parse the digital output data for displaying the temperature data and/or the operational data upon receiving the digital output data. In some implementations, the process 800 includes streaming the digital output data over a WiFi communications, Bluetooth, cellular, or other wireless connection or link or USB. In some implementations, the process 800 includes transmitting the digital output data over a wired connection.

Figure 9:
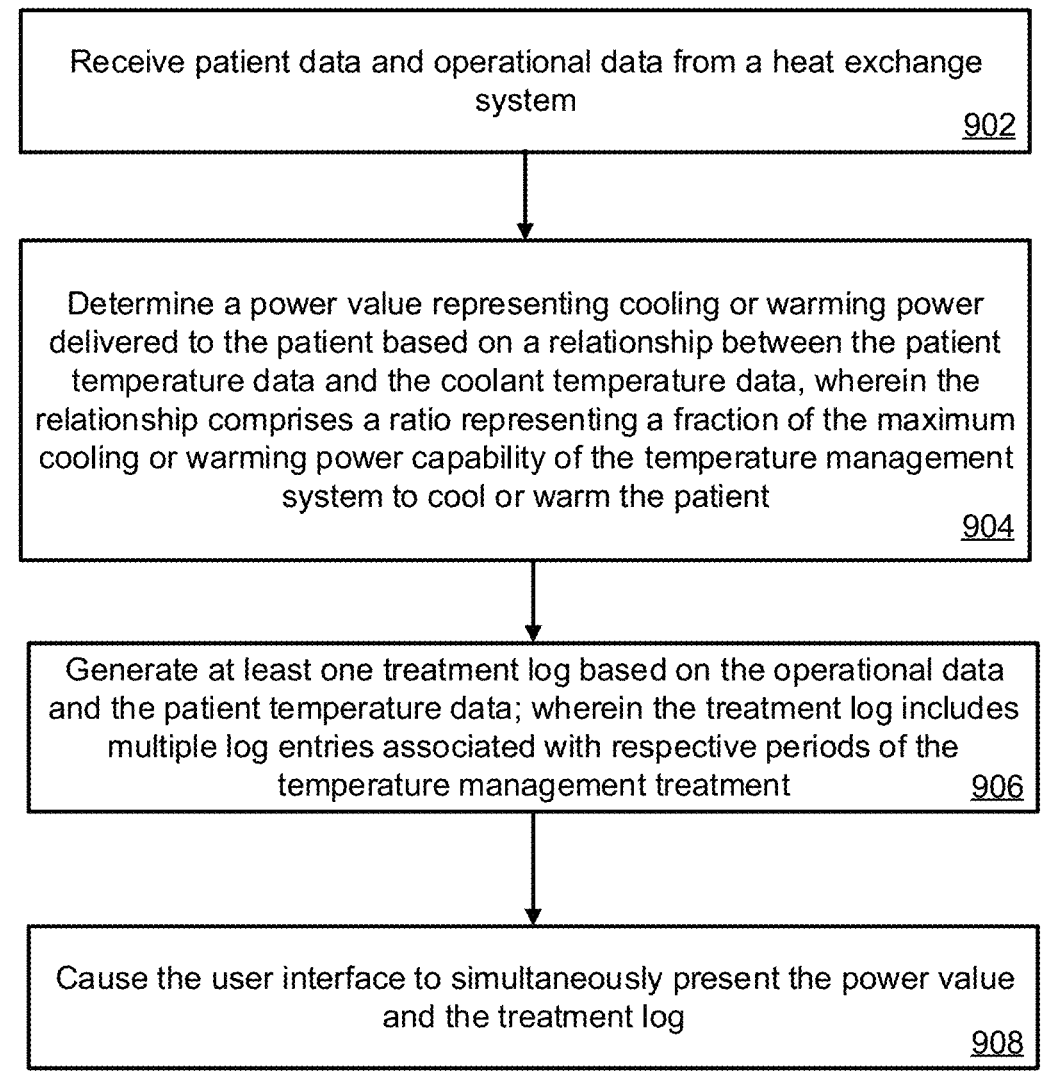
FIG. 9 shows a flow diagram including an example process for performing temperature management treatment for a patient and/or reporting, generating or displaying data from the temperature management treatment using a temperature management system such as the systems of FIG. 1, FIG. 2, and FIG. 3.

FIG. 9 shows a process 900 for treatment of a patient by a temperature management system. The temperature management system includes a heat exchange device coupled to an extracorporeal control console, the extracorporeal console configured to generate operational data. The operational data includes coolant temperature data representing a coolant temperature of the coolant during the temperature management treatment. The temperature management system includes one or more sensors coupled to the extracorporeal console and configured to generate patient temperature data indicative of a temperature of the body of the patient. The temperature management system includes a user interface that is coupled to the temperature management system. The temperature management system includes a processor, a memory storing instructions, and associated circuitry communicatively coupled to the temperature management system and the user interface. The processor is configured to execute the process 900. The process 900 includes receiving (902) the patient temperature data and the coolant temperature data from the temperature management system. The process 900 includes determining (904) a power value representing cooling or warming power delivered to the patient based on a relationship between the patient temperature data and the coolant temperature data, wherein the relationship comprises a ratio representing a fraction of the maximum cooling or warming power capability of the temperature management system to cool or warm the patient. The process 900 includes generating (906) at least one treatment log based on the operational data and the patient temperature data; wherein the treatment log includes multiple log entries associated with respective periods of the temperature management treatment. The process 900 includes causing (908) the user interface to simultaneously present the power value and the treatment log.

Figure 10:
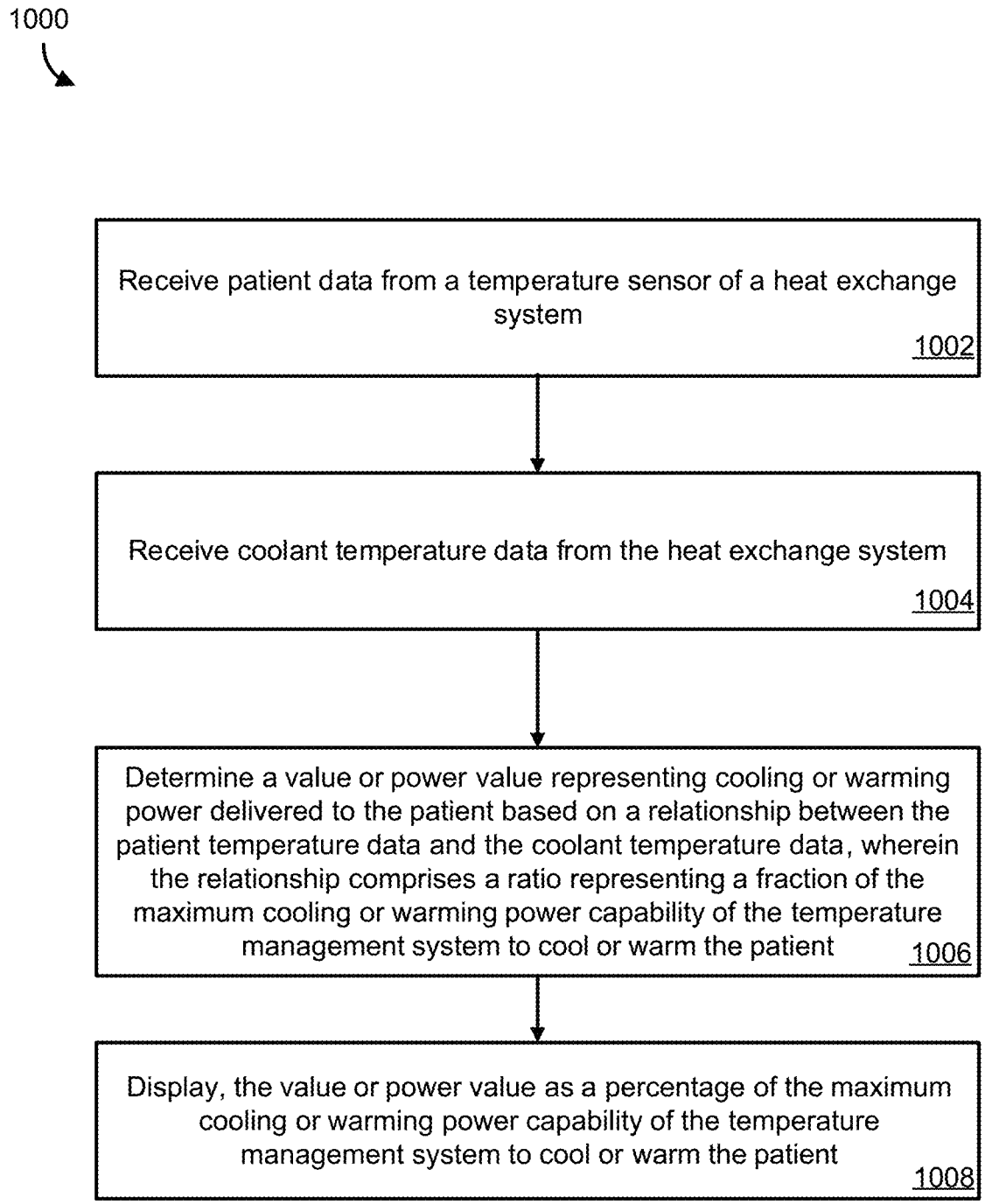
FIG. 10 shows a flow diagram including an example process for performing temperature management treatment for a patient and/or reporting, generating or displaying data from the temperature management treatment using a temperature management system such as the systems of FIG. 1, FIG. 2, and FIG. 3.

FIG. 10 shows a process 1000 for treatment of a patient by a temperature management system. The temperature management system includes a heat exchange device coupled to an extracorporeal control console. The temperature management system includes one or more sensors coupled to the extracorporeal control console and configured to generate patient temperature data indicative of a temperature of the body of the patient. The temperature management system includes a user interface that is coupled to the temperature management system. The temperature management system includes a processor, a memory storing instructions, and associated circuitry communicatively coupled to the temperature management system and the user interface. The processor is configured to execute the process 1000. The process 1000 includes receiving (1002) the patient temperature data from the sensor. The process 1000 includes receiving (1004) the coolant temperature data from the extracorporeal control console. The process 1000 includes determining (1006) a power value representing cooling or warming power delivered to the patient based on a relationship between the patient temperature data and the coolant temperature data, wherein the relationship comprises a ratio representing a fraction of the maximum cooling or warming power capability of the temperature management system to cool or warm the patient. The process 1000 includes generating and displaying (1008) the power value as a percentage of the maximum cooling or warming power capability of the temperature management system to cool or warm the patient.

Figure 11:
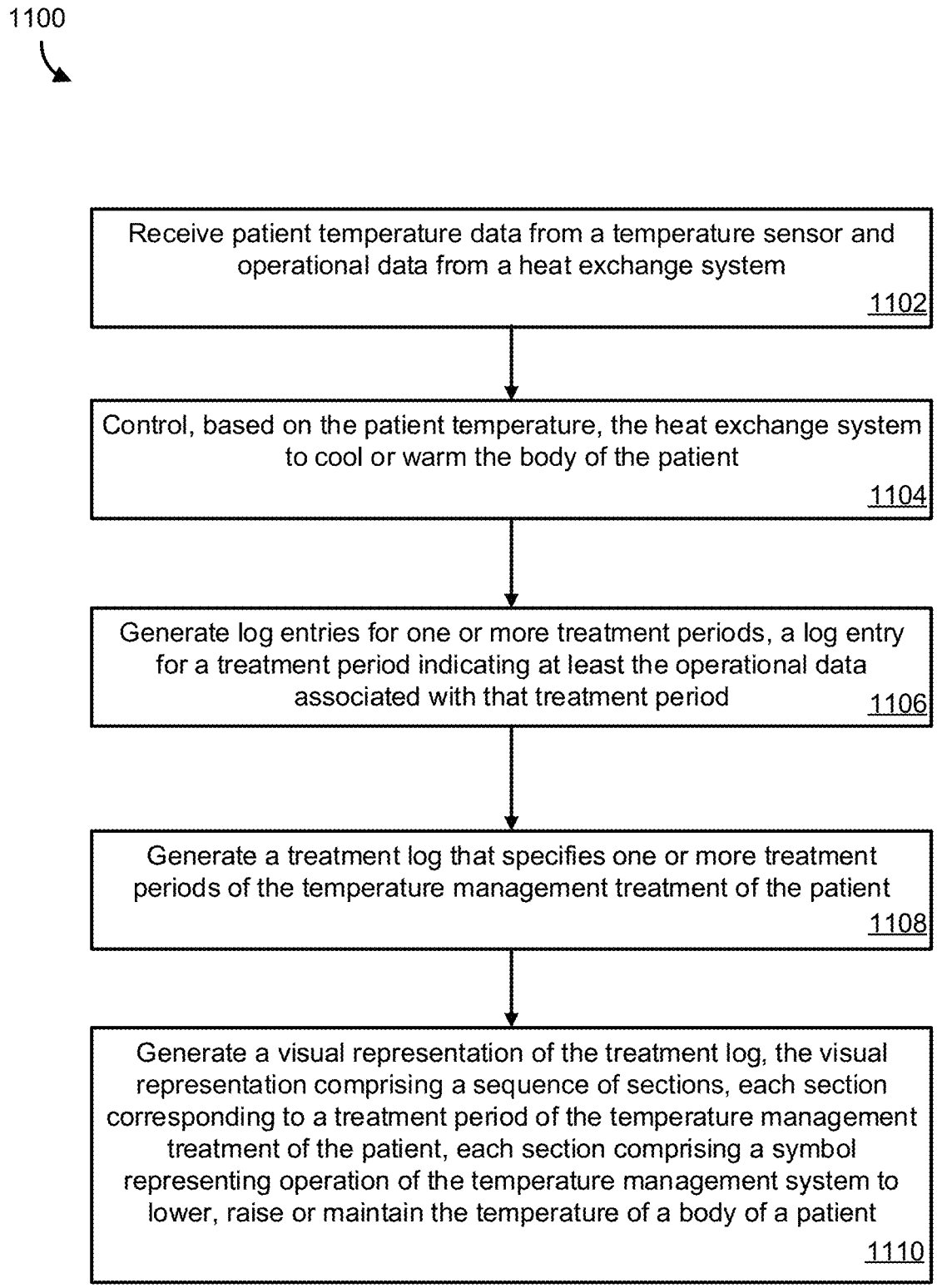
FIG. 11 shows a flow diagram including an example process for performing temperature management treatment for a patient and/or reporting, generating or displaying data from the temperature management treatment using a temperature management system such as the systems of FIG. 1, FIG. 2, and FIG. 3.
Figure 12:
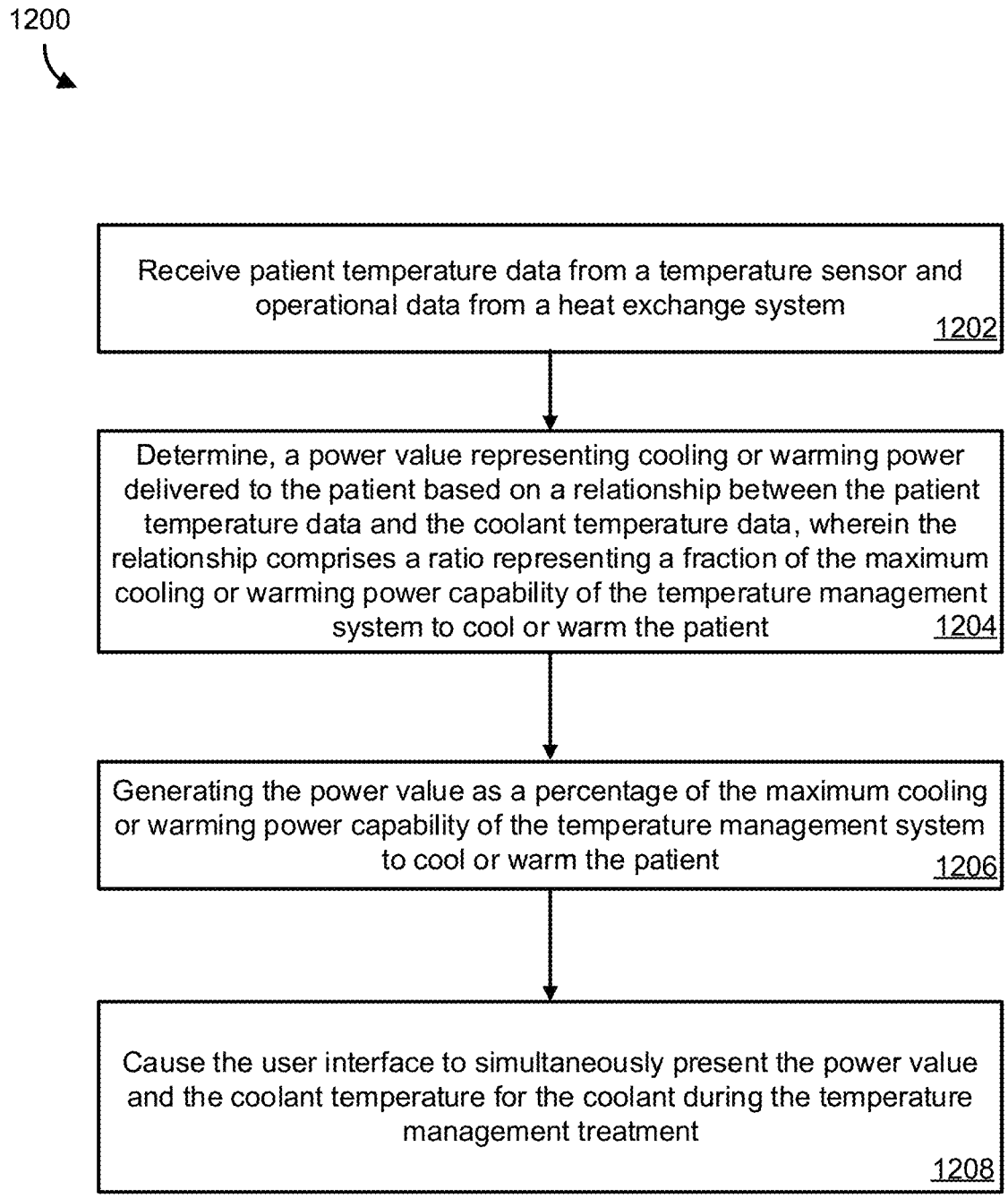
FIG. 12 shows a flow diagram including an example process for performing temperature management treatment for a patient and/or reporting, generating or displaying data from the temperature management treatment using a temperature management system such as the systems of FIG. 1, FIG. 2, and FIG. 3.

FIG. 11 shows a process 1100 for treatment of a patient by a temperature management system. The temperature management system includes a heat exchange device coupled to an extracorporeal control console. The temperature management system includes one or more sensors coupled to the extracorporeal control console and configured to generate patient temperature data indicative of a temperature of the body of the patient. The temperature management system includes a user interface that is coupled to the temperature management system. The temperature management system includes a processor, a memory storing instructions, and associated circuitry communicatively coupled to the temperature management system and the user interface. The processor is configured to execute the process 1100. The process 1100 includes receiving (1102) the patient temperature data from the sensor and the operational data from the temperature management system. The process 1100 includes controlling (1104), based on the patient temperature, the temperature management system to cool or warm the body of the patient. The process 1100 includes generating (1106) log entries for one or more treatment periods, a log entry for a treatment period indicating at least the operational data associated with that treatment period. The process 1100 includes generating (1108) a treatment log that specifies one or more treatment periods of the temperature management treatment of the patient. The process 1100 includes generating (1110) a visual representation of the treatment log, the visual representation comprising a sequence of sections, each section corresponding to a treatment period of the temperature management treatment of the patient, each section comprising a symbol representing operation of the temperature management system to lower, raise or maintain the temperature of a body of a patient, wherein each symbol is distinguished from each other symbol in the sequence of sections FIG. 12 shows a process 1200 for treatment of a patient by a temperature management system. The temperature management system includes a heat exchange device coupled to an extracorporeal control console. The temperature management system includes one or more sensors coupled to the extracorporeal control console and configured to generate patient temperature data indicative of a temperature of the body of the patient. The temperature management system includes a user interface that is coupled to the temperature management system. The temperature management system includes a processor, a memory storing instructions, and associated circuitry communicatively coupled to the temperature management system and the user interface. The processor is configured to execute the process 1200. The process 1200 includes receiving (1202) coolant temperature data and the patient temperature data from the temperature management system. The process 1200 includes determining (1204), a power value representing cooling or warming power delivered to the patient based on a relationship between the patient temperature data and the coolant temperature data, wherein the relationship comprises a ratio representing a fraction of the maximum cooling or warming power capability of the temperature management system to cool or warm the patient. The process 1200 includes generating (1206) the power value as a percentage of the maximum cooling or warming power capability of the temperature management system to cool or warm the patient. The process 1200 includes causing (1208) the user interface to simultaneously present the power value and the coolant temperature for the coolant during the temperature management treatment.

Some implementations of subject matter and operations described in this specification (e.g., processes 800, 900, 1000, 110, and 1200) can be implemented in digital electronic circuitry, or in computer software, firmware, or hardware, including the structures disclosed in this specification and their structural equivalents, or in combinations of one or more of them. For example, in some implementations, the processor of the temperature management system can be implemented using digital electronic circuitry, or in computer software, firmware, or hardware, or in combinations of one or more of them.

Some implementations described in this specification (e.g., the processor of the temperature management system, etc.) can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed for execution on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 13:
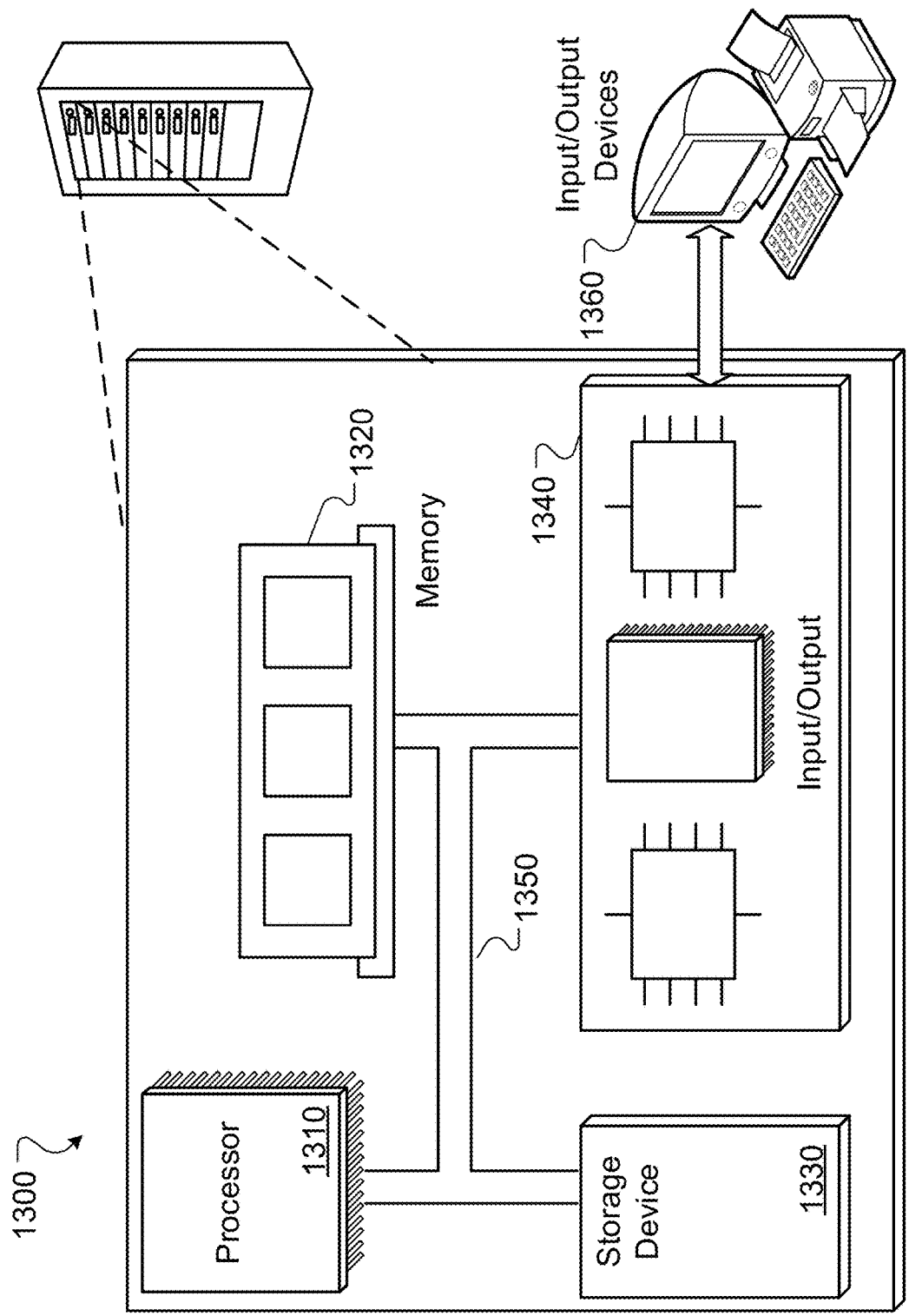
FIG. 13 is a diagram of an example computing system.

FIG. 13 shows an example computer system 1300 that includes a processor 13100, a memory 1320, a storage device 1330 and an input/output device 1340. Each of the components 13100, 1320, 1330 and 1340 can be interconnected, for example, by a system bus 1350. The processor 13100 is capable of processing instructions for execution within the system 1300. In some implementations, the processor 13100 is a single-threaded processor, a multi-threaded processor, or another type of processor. The processor 13100 is capable of processing instructions stored in the memory 1320 or on the storage device 1330. The memory 1320 and the storage device 1330 can store information within the system 1300.

The input/output device 1340 provides input/output operations for the system 1300. In some implementations, the input/output device 1340 can include one or more of a network interface device, e.g., an Ethernet card, a serial communication device, e.g., an RS-232 port, and/or a wireless interface device, e.g., an 802.11 card, a 3G wireless modem, a 4G wireless modem, a 5G wireless modem, etc. In some implementations, the input/output device can include driver devices configured to receive input data and send output data to other input/output devices, e.g., keyboard, printer and display devices 1360. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of embodiments have been described. For example, the detailed description and the accompanying drawings to which it refers are intended to describe some, but not necessarily all, examples or embodiments of the system. The described embodiments are to be considered in all respects only as illustrative and not restrictive. Nevertheless, various modifications may be made without departing from the scope of the data processing system described herein. Accordingly, other embodiments are within the scope of the following claims.

What is claimed is:

1. A temperature management system for controlling a temperature of a body of a patient, the system comprising:
    a heat exchange device configured to deliver a temperature management treatment to the patient;
    an extracorporeal control console coupled to the heat exchange device and configured to generate operational data representing operation of the temperature management system during the temperature management treatment;
    at least one sensor coupled to the extracorporeal control console and configured to generate a patient temperature data indicative of a temperature of the body of the patient;
    a processor, a memory storing instructions, and associated circuitry communicatively coupled to the sensor, wherein the processor is configured to:
        receive the patient temperature data from the sensor and the operational data from the extracorporeal control console;
        control, based on the patient temperature data, the temperature management system to cool or warm the body of the patient;
        generate log entries for one or more treatment periods, the log entries being populated with the operational data, a log entry of the log entries indicating at least the operational data representing operation of the extracorporeal control console during a respective treatment period of the temperature management treatment;
        generate a treatment log comprising the log entries, the treatment log specifying multiple treatment periods of the temperature management treatment of the patient; and
        generate a visual representation of the treatment log, the visual representation comprising a sequence of sections, each section having a respective log entry of the treatment log, wherein each section is separated in the visual representation from each other section and content of a section is rendered independently from each other section, wherein the content of the section is rendered when the respective log entry of that section is populated with the operational data representing the operation of the extracorporeal control console during the respective treatment period for that log entry, each section comprising:
            a symbol which visually represents an operational state of the temperature management system to lower, raise or maintain the temperature of a body of a patient; and
            a representation of a duration for the treatment period associated with the operational state of the temperature management system for the temperature management treatment of the patient.

2. The temperature management system of claim 1, wherein the log entry of the log entries includes operational data representing one or more of a cooling or warming rate applied during the treatment period, a target patient temperature value, a name of the treatment period, a time period associated with the treatment period, and a position of the treatment period relative to one or more other treatment periods for the temperature management treatment of the patient.

3. The temperature management system of claim 1, wherein the visual representation includes a representation of the log entries including the operational data and the patient temperature data associated with that treatment period.

4. The temperature management system of claim 1, wherein the visual representation of the log entries includes a list of the log entries.

5. The temperature management system of claim 1, wherein the visual representation of the log entries includes a sequence of symbols, each symbol of the sequence of symbols representing a corresponding log entry.

6. The temperature management system of claim 1, wherein each symbol of the sequence of sections includes a line segment that is separated from other symbols of the sequence of sections.

7. The temperature management system of claim 6, wherein a positioning of each line segment is determined based on one or more rules comprising:
    if the system is operating to raise a patient's temperature, a corresponding line segment is sloped and starts in a bottom-left corner of a corresponding section;
    if the system is operating to lower a patient's temperature, a corresponding line segment is sloped and starts in an upper-left corner of a corresponding section; and
    if the system is operating to maintain a patient's temperature, a corresponding line segment is horizontal and starts in a middle-left portion of a corresponding section.

8. The temperature management system of claim 6, wherein four consecutive line segments appear in adjacent sections, and wherein each subsequent line segment starts where a previous line ended in a Y axis or in a vertical direction in the section.

9. The temperature management system of claim 1, wherein each symbol represents the system operating in a manner to raise, lower or maintain the temperature of a body of a patient temperature.

10. The temperature management system of claim 1, wherein an alert associated with a log entry is generated, the alert indicating that a first treatment period has ended, and a second treatment period has commenced.

11. The temperature management system of claim 1, wherein the log entry for a treatment period indicates the operational data and the patient temperature data associated with that treatment period.

12. The temperature management system of claim 1, wherein the sequence of sections do not comprise a graph.

13. The temperature management system of claim 1, wherein the heat exchange device is a catheter or surface pad.

14. A temperature management system for controlling a temperature of a body of a patient, the system comprising:
    a heat exchange device configured to deliver a temperature management treatment to the patient;
    an extracorporeal control console coupled to the heat exchange device and configured to generate operational data representing operation of the temperature management system during the temperature management treatment;
    at least one sensor coupled to the extracorporeal control console and configured to generate a patient temperature data indicative of a temperature of the body of the patient;
    a processor, a memory storing instructions, and associated circuitry communicatively coupled to the sensor, wherein the processor is configured to:
        receive the patient temperature data and the operational data;

generate log entries for one or more treatment periods, the log entries being populated with the operational data, a log entry of the log entries indicating at least the operational data representing operation of the extracorporeal control console during a respective treatment period of the temperature management treatment and the patient temperature data for the treatment period;

generate at least one treatment log comprising the one or more log entries;

generate a visual representation of the treatment log comprising the one or more log entries, the visual representation comprising:

a sequence of sections, each section having a respective log entry of the treatment log, wherein each section is separated in the visual representation from each other section and content of a section is rendered independently from each other section, wherein the content of the section is rendered when the respective log entry of that section is populated with the operational data representing the operation of the extracorporeal control console during the respective treatment period for that log entry, each section comprising:

a symbol which visually represents an operational state of the temperature management system to lower, raise or maintain the temperature of a body of a patient; and a representation of a duration for a treatment period associated with the operational state of the temperature management system for the temperature management treatment of the patient.

15. The system of claim 14, wherein each symbol appears discontinuous from each other symbol.

16. The system of claim 14, wherein each symbol appears continuous with each other symbol, and wherein each symbol is distinguished using a color, pattern, or fill.

17. The system of claim 14, wherein each symbol appears at a relative height, within a corresponding section of the sequence of sections, to other symbols, wherein a relative height of a given symbol corresponds to a patient temperature or target temperature for the treatment period represented by that section.

18. The system of claim 14, wherein a section includes a text identifier indicating a system state corresponding to the treatment period of represented by that section.

19. The system of claim 14, wherein one or more sections of the sequence of sections include a numerical representation of a target patient temperature, an initial patient temperature, an ending patient temperature or any combination thereof for the treatment period of a section.

20. The temperature management system of claim 14, wherein the heat exchange device is a catheter or surface pad.

21. The temperature management system of claim 14, wherein the sequence of sections do not comprise a graph.

* * * * *